US006709838B1

(12) United States Patent
de Sauvage et al.

(10) Patent No.: US 6,709,838 B1
(45) Date of Patent: Mar. 23, 2004

(54) NUCLEIC ACID ENCODING PATCHED-2

(75) Inventors: Frederic de Sauvage, Foster City, CA (US); David A. Carpenter, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 51 days.

(21) Appl. No.: 09/060,939

(22) Filed: Apr. 15, 1998

(51) Int. Cl.$^7$ .......................... C12N 15/12; C07H 21/04

(52) U.S. Cl. .................. 435/69.1; 435/320.1; 435/358; 435/252.33; 435/254.21; 530/350; 536/23.5

(58) Field of Search .............................. 435/69.1, 252.3, 435/252.33, 254.2, 254.21; 536/23.1, 23.5; 530/350

(56) References Cited

U.S. PATENT DOCUMENTS

| | | | |
|---|---|---|---|
| 4,816,567 A | 3/1989 | Cabilly et al. ............ | 530/387.3 |
| 5,225,539 A | 7/1993 | Winter ..................... | 530/387.3 |
| 6,022,708 A | 2/2000 | de Sauvage et al. | |

FOREIGN PATENT DOCUMENTS

| | | |
|---|---|---|
| EP | 0 879 888 | 11/1998 |
| WO | WO 95/18856 | 7/1995 |
| WO | WO 96/11260 | 4/1996 |
| WO | WO 97/45541 | 12/1997 |
| WO | WO 99/29854 | 6/1999 |

OTHER PUBLICATIONS

Fujiwara et al., Human EST, Genebank Acession No. D60589, Genebank Record Date May 21, 1996, accessed Apr. 7, 1999, May 1996.*
Carpenter, D. et al., "Characterization of two patched receptors for the vertebrate hedgehog protein family" *Proc. Natl. Acad. Sci. USA* 95(23):13630–13634 (1998).
Takabatake, T. et al., "Hedgehog and patched gene expression in adult ocular tissues" *FEBS Letters* 410:485–489 (1997).
Zaphiropoulos, P.G. et al., "PTCH2, a novel human patched gene undergoing alternative splicing and up–regulated in basal cell carcinomas" *Cancer Research* 59:787–792 (1999).
Alcedo et al., "The Drosophila smoothened Gene Encodes a Seven–Pass Membrane Protein, a Putative Receptor for the Hedgehog Signal" *Cell* 86:221–232 (1996).
Apelqvist et al., "Sonic hedgehog directs specialised mesoderm differentiation in the intestine and pancreas" *Current Biology* 7(10):801–804 (Oct. 1, 1997).
Bellusci et al., "Involvement of Sonic hedgehog (Shh) in mouse embryonic lung growth and morphogenesis" *Development* 124(1):53–63 (Jan. 1997).

Bitgood et al., "Hedgehog and Bmp genes are coexpressed at many diverse sites of cell–cell interaction in the mouse embryo" *Developmental Biology* 172(1):126–138 (Nov. 1995).
Bitgood et al., "Sertoli Cell Signaling by Desert Hedgehog Regulates the Male Germline" *Current Biology* 6(3):298–304 (1996).
Chen and Struhl, "Dual roles for patched in sequestering and transducing Hedgehog" *Cell* 87(3):553–563 (Nov. 1, 1996).
de Jong et al., "Pathogenesis of adult testicular germ cell tumors. A cytogenetic model" *Cancer Genetics & Cytogenetics* 48(2):143–167 (Sep. 1990).
Echelard et al., "Sonic hedgehog, a member of a family of putative signaling molecules, is implicated in the regulation of CNS polarity" *Cell* 75:1417–1430 (1993).
Ericson et al., "Sonic hedgehog induces the differentiation of ventral forebrain neurons: a common signal for ventral patterning within the neural tube" *Cell* 81(5):747–756 (Jun. 2, 1995).
Fan et al., "Patterning of mammalian somites by surface ectoderm and notochord: evidence for sclerotome induction by a hedgehog homolog" *Cell* 79(7):1175–1186 (Dec. 30, 1994).
Gailani et al., "The role of the human homologue of Drosophila patched in sporadic basal cell carcinomas" *Nature Genetics* 14:78–81 (Sep. 1996).
Goodrich et al., "Conservation of the hedgehog/patched signaling pathway from flies to mice: induction of a mouse patched gene by Hedgehog" *Genes Dev.* 10(3):301–312 (1996).
Hahn et al., "Mutations of the Human Homolog of Drosophila Patched in the Nevoid Basal Cell Carcinoma Syndrome" *Cell* 85:841–851 (1996).
Hynes et al., "Control of cell pattern in the neural tube by the zinc finger transcription factor and oncogene Gli–1" *Neuron* 19(1):15–26 (Jul. 1997).
Johnson et al., "Ectopic expression of Sonic hedgehog alters dorsal–ventral patterning of somites" *Cell* 79:1165–1173 (1994).
Johnson et al., "Human Homolog of Patched, a Candidate Gene for the Basal Cell Nevus Syndrome" *Science* 272:1668–1671 (1996).
Jones et al., "Replacing the Complementarity–determining Regions in a Human Antibody with Those From a Mouse" *Nature* 321:522–525 (May 29, 1986).
Krauss et al., "A functionally conserved homolog of the Drosophila segment polarity gene hh is expressed in tissues with polarizing activity in zebrafish embryos" *Cell* 75:1431–1444 (1993).

(List continued on next page.)

Primary Examiner—Yvonne Eyler
Assistant Examiner—Eileen B O Hara
(74) Attorney, Agent, or Firm—Craig G. Svoboda

(57) ABSTRACT

The present invention relates to nucleotide sequences, including expressed sequence tags (ESTs), oligonucleotide probes, polypeptides, antibodies, vectors and host cells expressing, immunoadhesins, agonists and antagonists to patched-2.

23 Claims, 27 Drawing Sheets

OTHER PUBLICATIONS

Laufer et al., "Sonic hedgehog and Fgf–4 act through a signaling cascade and feedback loop to integrate growth and patterning of the developing limb bud" *Cell* 79(6):993–1003 (Dec. 16, 1994).

Marigo et al., "Biochemical evidence that patched is the Hedgehog receptor" *Nature* 384(6605):176–179 (Nov. 14, 1996).

Marigo et al., "Conservation in hedgehog signaling: Induction of a chicken patched homolog by Sonic hedgehog in the developing limb" *Development* 122:1225–1233 (1996).

Marti et al., "Requirement of 19K form of Sonic hedgehog for induction of distinct ventral cell types in CNS explants" *Nature* 375(6529):322–325 (May 25, 1995).

Morrison et al., "Chimeric Human Antibody Molecules: Mouse Antigen–binding Domains with Human Constant Region Domains" *Proc. Natl. Acad. Sci. USA* 81:6851–6855 (Nov. 1984).

Motoyama et al., "Ptch2, a second mouse Patched gene is co–expressed with Sonic hedgehog" *Nature Genetics* 18(2):104–106 (Feb. 1998).

Nakano et al., "A protein with several possible membrane–spanning domains encoded by the Drosophila segment polarity gene patched" *Nature* 341:508–513 (1989).

Nusslein–Volhard et al., "Mutations Affecting the Pattern of the Larval Cuticle in Drosophila Melanogaster" *Roux's Archives of Developmental Biology* 193(5):267–282 (1984).

Oro et al., "Basal cell carcinomas in mice overexpressing sonic hedgehog" *Science* 276(5313):817–821 (May 2, 1997).

Perrimon, N., "Hedgehog and Beyond" *Cell* 80:517–520 (1995).

Presta, L., "Antibody Engineering" *Curr. Op. Struct. Biol.* 2:593–596 (1992).

Rassoulzadegan et al., "Transmeiotic differentiation of male germ cells in culture" *Cell* 75(5):997–1006 (Dec. 3, 1993).

Riddle et al., "Sonic hedgehog mediates the polarizing activity of the ZPA" *Cell* 75:1401–1416 (1993).

Riechmann et al., "Reshaping Human Antibodies for Therapy" *Nature* 332:323–327 (Mar. 24, 1988).

Roberts et al., "Sonic hedgehog is an endodermal signal inducing Bmp–4 and Hox genes during induction and regionalization of the chick hindgut" *Development* 121:3163–3174 (1995).

Stone et al., "The tumour–suppressor gene patched encodes a candidate receptor for Sonic hedgehog" *Nature* 384(14):129–134 (Nov. 1996).

Summersgill et al., "Molecular cytogenetic analysis of adult testicular germ cell tumours and identification of regions of consensus copy number change" *British Journal of Cancer* 77(2):305–313 (1998).

van den Heuvel and Ingham, "Smoothened Encodes a Receptor–Like Serpentine Protein Required for Hedgehog Signalling" *Nature* 382:547–551 (1996).

Vortkamp et al., "Regulation of rate of cartilage differentiation by Indian hedgehog and PTH–related protein" *Science* 273:613–622 (1996).

Wallis, G., "Bone growth: Coordinating chondrocyte differentiation" *Current Biology* 6(12):1577–1580 (1996).

Wicking and Bale, "Molecular basis of the nevoid basal cell carcinoma syndrome" *Current Opinion in Pediatrics* 9:630–635 (1997).

Xie et al., "Activating Smoothened mutations in sporadic basal–cell carcinoma" *Nature* 391(6662):90–92 (Jan. 1, 1998).

Xie et al., "Mutations of the Patched gene in several types of sporadic extracutaneous tumors" *Cancer Research* 57(12):2369–2372 (Jun. 15, 1997).

\* cited by examiner

```
  1 GTTATTTCAG GCCATGGTGT TGCGCCGAAT TAATTCCGA  TCCAGACATG ATAAGATACA TTGATGAGTT TGGACAAACC ACAACTAGAA TGCAGTGAAA
    CAATAAAGTC CGGTACCACA ACGCGGCTTA ATTAAGGGCT AGGTCTGTAC TATTCTATGT AACTACTCAA ACCTGTTTGG TGTTGATCTT ACGTCACTTT
    (SEQ ID NO:1)

101 AAAATGCTTT ATTTGTGAAA TTTGTAACCA TATTGCTTTA TTTGTAAGCT CAATAAACAA GTTGGGCCAT GTTGGGCCAAG GGCGGCCAAG CTTCTGCAGG
    TTTTACGAAA TAAACACTTT AAACACTACG ATAACGAAAT AAACATTCGA GTTATTTGTT CAACCCGGTA CAACCCGGTT CCCGCCGGTT GAAGACGTC

201 TCGACTCTAG AGGATCCCCG GGGAATTCCG GCATGACTCG CTCAGAGAGC TGCCCCCGAG TTACACACCC CCAGCTGAA CCGCAGCACC
    AGCTGAGATC TCCTAGGGGC CCCTTAAGGC CGTACTGAGC GAGTCTCTCG ACGGGGGCTC AATGTGTGGG GGTCGAGCTT GGCGTCGTGG
                                                 M  T  R  S  P  P  L  R  E  L  P  P  S  Y  T  P  P  A  R  T  A  A  P
                                       insert starts here        (SEQ ID NO:2)

301 CCAGATCCTA GCTGGAGCC TGAAGGCTCC ACTCTGGCTT CGTGCTTACT TCCAGGGCCT GCTCTCTCTT CTGGGATGCG GGATCCAGAG ACATTGTGGC
    GGTCTAGGAT CGACCCTCGG ACTTCCGAGG TGAGACCGAA GCACGAATGA AGGTCCCGGA CGAGAGAGAA GACCCTACGC CCTAGGTCTC TGTAACACCG
 24  Q  I  L  A  G  S  L  K  A  P  L  W  L  R  A  Y  F  Q  G  L  L  F  S  L  G  C  G  I  Q  R  H  C  G

401 AAAGTGCTCT TTCTGGGACT GTTGGCCTTT GGGGCCCTGG CCGCATGGCT ATTATTGAGA CAAACTTGGA ACAGCTCTGG GTAGAAGTGG
    TTTCACGAGA AAGACCCTGA CAACCGGAAA CCCCGGGACC GGCGTACCGA TAATAACTCT GTTTGAACCT TGTCGAGACC CATCTTCACC
 57  K  V  L  F  L  G  L  L  A  F  G  A  L  A  L  R  M  A  I  I  E  T  N  L  E  Q  L  W  V  E  V  G

501 GCAGCCGGGT GAGCCAGGAG CTGCATTACA CCAAGGAGAA GCTGGGGGAG CCTCCACCTC CAGGCAGCCC GATGCTGATA CAGACCGCAC GCCAGGAGGG
    CGTCGGCCCA CTCGGTCCTC GACGTAATGT GGTTCCTCTT CGACCCCCTC GGAGGTGGAG GTCCGTCGGG CTACGACTAT GTCTGGCGTG CGGTCCTCCC
 91  S  R  V  S  Q  E  L  H  Y  T  K  E  K  L  G  E  A  A  Y  T  S  Q  M  L  I  Q  T  A  R  Q  E  G

601 AGAGAACATC CTCACACCCG AAGCACTTGG CCTCCACCTC CAGGCAGCCC TCACTGCCAA TAAAGTCCAA ATTTCAGTTT ATGGAAGTC CTGGGATTTG
    TCTCTTGTAG GAGTGTGGGC TTCGTGAACC GGAGGTGGAG GTCCGTCGGG AGTGACGGTT ATTTCAGGTT TAAAGTCAAA TACCCTTCAG GACCCTAAAC
124  E  N  I  L  T  P  E  A  L  G  L  H  L  Q  A  A  L  T  A  S  K  V  Q  I  S  V  Y  G  K  S  W  D  L

701 AACAAAATCT GCTACAAGTC AGGAGTTCCC CTTATTGAAA TGGAATGGAT TACCTCACCT ACTCACCTAC GCAAAGGCAC GCACTAGGAG TGGGGGAGC
    TTGTTTTAGA CGATGTTCAG TCCTCAAGGG GAATAACTTT ACCTTACCTA ATGGAGTGGA TGAGTGGATG CGTTTCCGTG GCACTAGGAG TGGGGGAGC
157  N  K  I  C  Y  K  S  G  V  P  L  I  E  N  G  M  I  E  W  M  I  E  K  L  F  P  C  V  I  L  T  P  L  D

801 ACTGCTTCTG GGAGGGAGCC AAACTCCAAG GGGCTCCGC CTACCTGCCC GGCCGGCCGG ATATCCAGTG GACCAACCTG GATCCAGAGC AGCTGCTGGA
    TGACGAAGAC CCTCCCTCGG TTTGAGGTTG CCCGAGGCG GATGGACGGG CCGGCCGGCC TATAGGTCAC CTGGTTGGAC CTAGGTCTCG TCGACGACCT
191  C  F  W  E  G  A  K  L  Q  G  G  S  A  Y  L  P  G  R  P  D  I  Q  W  T  N  L  D  P  E  Q  L  L  E
```

```
1801  GCTGCGAGCC TTCTCCCTAC AGGCGGCCAT AGTGGTTGGC TGCACCTTTG TAGCCGTGAT GCTTGTCTTC CCAGCCATCC TCAGCCTGGA CCTACGGGCG
      CGACGCTCGG AAGAGGGATG TCCGCCGGTA TCACCAACCG ACGTGGAAAC ATCGGCACTA CGAACAGAAG GGTCGGTAGG AGTCGGACCT GGATGCCGCC
524   L  R  A    F  S  L  Q    A  A  I    V  V  G    C  T  F  V    A  V  M    L  V  F    P  A  I  L    S  L  D.   L  R  R

1901  CGCCACTGCC AGCGCCTTGA TGTGCTCTGC TGCTTCCTCA GTCCCTGCTC TGCTCAGGTG ATTCAGATCC TGCCCCAGGA GCTGGGGGAC GGGACAGTAC
      GCGGTGACGG TCGCGGAACT ACACGAGACG ACGAAGGAGT CAGGGACGAG ACGAGTCCAC TAAGTCTAGG ACGGGGTCCT CGACCCCCTG CCCTGTCATG
557   R  H  C  Q    R  L  D    V  L  C    C  F  S  S    P  C  S    A  Q  V    I  Q  I  L    P  Q  E    L  G  D    G  T  V  P

2001  CAGTGGGCAT TGCCCACCTC ACTGGGGCTC TTCAAGCCTT TACCCACTGT GAAGCCAGCA GCCAGCCATG GGTCACCATC CTGCCCTCCC AAGCCCACCT
      GTCACCCGTA ACGGGTGGAG TGACGGGCGAG AAGTTCGGAA ATGGGTGACA CTTCGGTCGT CGGTCGTACA CCAGTCGTAG GACGGGAGGG TTCGGGTGGA
591   V  G  I    A  H  L    T  A  T  V    Q  A  F    T  H  C    E  A  S  S    Q  H  V    V  T  I    L  P  P  Q    A  H  L

2101  GGTGCCCCCA CCTTCTGACC CACTGGGCTC TGAGCTCTTC AGCCCCTGGA GGACCTTCTA GGCCAGGAGG GGACCTTTCA AGGAGACAAG GCAGAAGGCA
      CCACGGGGGT GGAAGACTGG GTGACCCGAG ACTCGAGAAG TCGGGGACCT CCTGGAAGAT CCGGTCCTCC CCTGGAAAGT TCCTCTGTTC CGTCTTCCGT
624   V  P  P    P  S  D  P    L  G  S    E  L  F    S  P  G  G    D  L  L    G  Q  E  E    E  T  R    Q  K  A

2201  GCCTGCAAGT CCCTGCCCTG CTATCAGTTT AATCTTGCCC ATTTCGCCCG TGCTTCCAGTC ACATGCCAAG GCCATCGTGC
      CGGACGTTCA GGGACGGGAC GATAGTCAAA TTAGAACGGG TAAAGCGGGC ACGAGGTCAG TGTACGGTTC CGGTAGCACG
657   A  C  K  S    L  P  C    A  R  W    N  L  A  H    F  A  R    Y  Q  F    A  P  L  L    L  Q  S    H  A  K    A  I  V  L

2301  TGGTGCTCTT CTGGGCCTAC AGCCACCTTG GTGCAAGACG GCCTGGCCCT GACGGATGTG GTGCCCTGGG GCACCCAAGGA
      ACCACGAGAA GACCCGGATG TCGGTGGAAC CACGTTCTGC CGGACCGGGA CTGCCTACAC CACGGGACCC CGTGGTTCCT
691   V  L  F    G  A  L    L  G  L  S    L  Y  G    A  T  L    V  Q  D  G    L  A  L    T  D  V    V  P  R  G    T  K  E

2401  GCATGCCTTC CTGAGCGCCC AGCTCAGTTA CTTCTCCCTG TACGAGGTGG CCAGGGCTGGC CCAGTTCCA ACGCGCCCTC
      CGTACGGAAG GACTCGCGGG TCGAGTCAAT GAAGAGGGAC ATGCTCCACC GGTCCCACTG GGTAAGGGT TGCGCGGGAG
724   H  A  F    L  S  A  Q    H  Q  R  F    S  S  L    K  A  V  L    Y  E  V  A    L  V  T    Q  G  G    F  D  Y  A    H  S  Q    R  A  L

2501  TTTGATCTGC ACCAGCGCTT CAGTTCCCTC AAGGCGGGTG TTCCGCCACG GCACCCCCAG GCACCCCGCA CCTGGCTGCA CTATTACCGC AACTGCTAC
      AAACTAGACG TGGTCGCGAA GTCAAGGGAG TTCCGCCCAC AAGGCGGTGC CGTGGGGGTC CGTGGGGCGT GGACCGACGT GATAATGGCG TTGACGATG
757   F  D  L  H    Q  R  F    S  S  L    K  A  V  L    P  P  P    A  T  Q    A  P  R  T    W  L  H    Y  Y  R    N  W  L  Q

2601  AGGGAATCCA GGCTGCCTTT GACCAGGACT GGGCTTCTGG GCCATCACC CGCCACTCGT CTCTGAGGAT GGGGCCCTGG GCCCGGGACC GGATGTTCGA
      TCCCTTAGGT CCGACGGAAA CTGGTCCTGA CCCGAAGACC CGCGTAGTGG GCGGTGAGCA GAGACTCCTA TGGCGTTACC CCCGGGACCT GGATGTTCGA
791   G  I  Q    A  A  F    D  Q  D  W    A  S  G    R  I  T    R  H  S  Y    R  N  G    S  E  D    G  A  L  A    Y  K  L
```

```
3601  GTACAAGGAA AGCCCAGAGA TCCTGAGTCC ACCAGCTCCA CAGGGAGGCG GGCTTAGGTG GGGGGCATCC TCCTCCCTGC CCCAGAGCTT TGCCAGAGTG
      CATGTTCCTT TCGGGTCTCT AGGACTCAGG TGGTCGAGGT GTCCCTCCGC CCGAATCCAC CCCCCGTAGG AGGAGGGACG GGGTCTCGAA ACGGTCTCAC
1124   Y  K  E   S  P  E  I   L  S  P    P  A  P    Q  G  G  G   L  R  W    G  A  S    S  L  P    Q  S  F    A  R  V

3701  ACTACCTCCA TGACCGTGGC CATCCACCCA CCCCCCCTGC CTGGTGCCTA CATCCATCCA GCCCCTGATG AGCCCCCTTG GTCCCCTGCT GCCACTAGCT
      TGATGGAGGT ACTGGCACCG GTAGGTGGGT GGGGGGGACG GACCACGGAT GTAGGTAGGT CGGGGACTAC TCGGGGAAC CAGGGGACGA CGGTGATCGA
1157   T  T  S  M   T  V  A    I  H  P    P  P  L  P   G  A  Y    I  H  P    A  P  D  E    P  P  W    S  P  A    A  T  S

3801  CTGGCAACCT CAGTTCCAGG GGACCAGGTC CAGCCACTGG GTGAAAGAGC AGCTGAAGCA CAGAGACCAT GTGTGGGGCG TGTGGGGTCA CTGGGAAGCA
      GACCGTTGGA GTCAAGGTCC CCTGGTCCAG GTCGGTGACC CACTTTCTCG TCGACTTCGT GTCTCTGGTA CACACCCCGC ACACCCCAGT GACCCTTCGT
1191   G  N  L   S  S  R    G  P  G  P    A  T  G  ←1203

3901  CTGGGTCTGG TGTTAGACGC AGGACGGACC CCTGGAGGGC CCTGCTGCTG CTGCATCCCC TCTCCCGACC CAGCTGTCAT GGGCCTCCCT GATATCGAAT
      GACCCAGACC ACAATCTGCG TCCTGCCTGG GGACCTCCCG GGACGACGAC GACGTAGGGG AGAGGGCTGG GTCGACAGTA CCCGGAGGGA CTATAGCTTA
                           ^T to C (silent)                                                pRK follows, this is the 5prime end of vector^

4001  TCAATCGATA GAACCGAGGT GCAGTTGGAC
      AGTTAGCTAT CTTGGCTCCA CGTCAACCTG
```

FIG. 1E

```
(SEQ ID NO: 3)                30        40        50        60        70
            905531    GCTGGGGTGCACGCCTACCNCAGCGGNTCCCCCTTCCTCTTCTGGGAACA
                      ::: ::  :     ****** *****  ******************  **
            hpatched  CTGGGGCTGTCCAGTTACCCCAACGGCTACCCCTTCCTCTTCTGGGAGCA
(SEQ ID NO: 4)          3010      3020      3030      3040      3050

80        90        100       110       120
            905531    GTATCTGGGCCTGCGGCGCTGCTTCCTGCTGGCCGTCTGCATCCTGCTGG
                      ***  * ***** **  * ***  * ******  * **  **  * ** ***
            hpatched  GTACATCGGCCTCCGCCACTGGCTGCTGCTGTTCATCAGCGTGGTGTTGG
                        3060      3070      3080      3090      3100

130       140       150       160       170
            905531    TGTGCACTTTCCTCGTCTGTGCTCTGCTGCTCCTNAACCCCTGGACGGCT
                      *****  ******** ** ***  *  * ** ******************
            hpatched  CCTGCACATTCCTCGTGTGCGCTGTCTTCCTTCTGAACCCCTGGACGGCC
                        3110      3120      3130      3140      3150

180       190       200       210       220
            905531    GGCCTNATAGTGCTGGTCCTGGCGATGATGACAGTGGAACTCTTTGGTAT
                      **  ****  *** ************ ****** ** ** ** ** ** **
            hpatched  GGGATCATTGTGATGGTCCTGGCGCTGATGACGGTCGAGCTGTTCGGCAT
                       3160       3170      3180      3190      3200

230       240       250
            905531    CATGGGTTTNCTGGGCATCAAGCTGAGT
                      *****   **  * ** ******* ***
            hpatched  GATGGGCCTCATCGGAATCAAGCTCAGT
                        3210      3220      3230

80        90        100       110       120
            905531    TCTGGGCCTGCGGCGCTGCTTCCTGCTGGCCGTCTGCATCCTGCTGGTGT
                      :::   :::    * **  *  ** *****    ****    *  ** ****
            hpatched  GCTGCTGTTCATCAGCGTGGTGTTGGCC---TGCACATTCCTCGTGT
                        3090      3100      3110      3120

130       140       150
            905531    GCACTTTCCTCGTCTGTGCTCTGCTGCT
                      ** ** ** **  *    :       :
            hpatched  GCGCTGTCTTCCTTCTGAACCCCTGGAC
                        3130      3140      3150
```

FIG. 2A

```
                              30         40         50         60         70
(SEQ ID NO:5) 1326258    GCTGGGGTGCACGCCTACCCCAGCGGCTCCCCCTTCCTCTTCTGGGAACA
                         ::: ::   :    ******  *****  ******************  **
              hpatched   CTGGGGCTGTCCAGTTACCCCAACGGCTACCCCTTCCTCTTCTGGGAGCA
                             3010      3020      3030      3040      3050

80         90        100        110        120
              1326258    GTATCTGGGCCTGCGGCGCTGCTTCCTGCTGGCCGTCTGCATCCTGCTGG
                         ***  *  *****  ** *  ***  *  ****** *  ** ** *  ** ***
              hpatched   GTACATCGGCCTCCGCCACTGGCTGCTGCTGTTCATCAGCGTGGTGTTGG
                             3060      3070      3080      3090      3100

130        140        150
              1326258     TGTGCACTTTCCTCNTCTGTGCTCT
                          *****  ********  **  ***  *
              hpatched    CCTGCACATTCCTCGTGTGCGCTGT
                             3110      3120      3130

90        100        110        120        130
              1326258    TCTGGGCCTGCGGCGCTGCTTCCTGCTGGCCGTCTGCATCCTGCTGGTGT
                         : : :    : : :      * ** *  ** *****   ****    * ** ****
              hpatched   GCTGCTGCTGTTCATCAGCGTGGTGTTGGCC---TGCACATTCCTCGTGT
                             3090      3100      3110           3120

140        150
              1326258    GCACTTTCCTCNTCTGTGCTCT
                         ** ** **  ****           :
              hpatched   GCGCTGTCTTCCTTCTGAACCC
                             3130      3140

10         20         30         40         50
              1326258         CCGGGCAGCATGCGCAGAGGCCGGCCAGGCTGGGGTGCACGCCTACCCCA
                              ******  *****    ** **  *  ***  *******    *           :
(SEQ ID NO:6) hpatched.RC     CCGGGCGGCATG--GCGAAGCGGACCACGCTGGGGGGTGGCTCAGGGGAG
                                  710        720        730        740        750
```

FIG. 2B (SEQ ID NO:4) PTCH    1 MASAGNAAEPQDRGGGSGCIGAPGRPAGGGRRRTGGLRRAAAPDRDYL
(SEQ ID NO:2) PTCH2   1 ...............................MTRSPPLREL·

PTCH   51 HRPSYCDAAFALEQISKGKATGRKAPLWLRAKFQRLLFKLGCYIQKNCGK
PTCH2  11 ·PPSYTPP··ARTAAPQILAGSLKAPLWLRAYFQGLLFSLGCGIQRHCGK

TM1
PTCH  101 FLYVGLLFGAFAVGLKAANLETNVEELWVEGGRVSRELNYTRQKIGEE
PTCH2  58 VLFIGLLAEGAIALGLRMA·IJEINLEQLWVEVGSRVSQELHYTKEKLGEE

PTCH  151 AMFNPQLMIQTPKEEGANVLTTEALLQHLDSALQASRVHVYMYNRQWKLE
PTCH2 108 AAYTSQMLLQTARQEGENILTIPEALGLHLQAALTASKVQVSLYGKSWDLN

PTCH  201 HLCYKSGELITETGYMDQIIEYLYPCLIITPLDCFWEGAKLQSGTAYLLG
PTCH2 158 KICYKSGVPLIENGMIEWMIEKLFPGVLTPLDCFWEGAKLQGGSAYLPG

PTCH  251 KPPLRWTNFDPLEFLEELKKINYQVDSWEEMLNKAEVGHGYMDRPCLNPA
PTCH2 208 RPDIQWINLDPEQLLEELGPFA·SLEGFREILLDKAQVGQAYVGRPCLHPD

PTCH  301 DPDCPATAPNKNSTKPLDMALVLNGGCHGLSRKYMHWQEELIVGGTVKNS
PTCH2 257 DLHCPPSAPNHHSRQAPNVAHELSGGCHGFSHKFMHWQEELLLGGMARDP

PTCH  351 TGKLVSAHALQTMFQLMTPKQMYEHFKGYEYVSH·INWNEDKAAAILEAW
PTCH2 307 QGELLRAEALQSTFLLMSPRQLYEHFRG·DYQTHDLGWSEEQASTVLQAW

PTCH  400 QRTYEVVHQSVAQNSTQKVLSFTTLDDILKSFSDVSVRVASQLLM
PTCH2 356 QRFVQLAQEALPENASQQIHAFSSTTLDDILHAFSEVSAARVVGGILLM
                                                    TM2

FIG. 3A

```
                                         TM3
PTCH  450  L A Y A C L T M L R W D C S K S Q G A V G L A G V L L V A L S V A A G L G L C S L L G S F N A A T
PTCH2 406  L A Y A C V T M L R W D C A Q S Q G S V G L A G V L L V A L L A H F T E A L P G · · T P L Q E R M G E C L Q R T G T S V M

TM4
PTCH  500  T Q V L P F L A L G V G V D D V F L L A H A F S E T G Q N K R I P F E D R T G E C L K R T G A S Y A
PTCH2 456  T Q V L P F L A L G I G V D D V F L L A H A F T E A L P G · · T P L Q E R M G E C L Q R T G T S V M

TM5
PTCH  550  L T S I S N V T A F F M A A L I P I P A L R A F S L Q A A V V V V F N F A M V L L F P A I L S M D
PTCH2 504  L T S I N N M A A L F M A A L V P I P A L R A F S L Q A A I Y V G C T E V A V M L V E P A I L S L D

PTCH  600  L Y R R E D R R L D I F C C F T S P C V S R V I Q V E P Q A Y T D T H D N T R Y S P P P P Y S S H S
PTCH2 554  L R R H C Q R L D V L C C F S S P C S A Q V I I L P Q E L G D G T · · · · · · · · · · V P V G

PTCH  650  F A H E T Q I T M Q S T V Q L R T E Y D P H T H V Y Y T A E P R S E I S V Q P V T V T Q D T L S C
PTCH2 593  I A H · · · · · L T A I V Q A F T H C E A S S Q H V V I L P P Q A H L V P P P · · · · S D P L G S

TM7
PTCH  700  Q S P E S T S S T R D L L S Q F S D S S L H · · C L E P P C T K W T L S S F A E K H Y A P F L L K P
PTCH2 634  E L F S P G G S T R D L L G E E E T R Q K A A C K S L P C A R W N L A H F A R Y Q F A P L L L Q S

PTCH  748  K A K V V V F L T L G L D G V S L Y G T T R V R D G L D L T D I V P R E T R E Y D F I A Q F K Y
PTCH2 684  H A K A I V L V I E G A L L E G L S L V G A I L V Q D G L A L T D V V P R G T K E H A F L S A Q L R Y

PTCH  798  F S F Y N M Y I V T Q K A · D Y P N I Q H L L Y D L H R S F S N V K Y M L E E N K Q L P K M W L H
PTCH2 734  F S L Y E V A L V T Q G G F D Y A H S Q R A L F D L H Q R F S S L K A V L P P P A T Q A P R T W L H
```

```
PTCH  1247  AGG PAHQVIVEATENPVFAHSTVVHPESRHHPPSNPRQQPHLDSGSLPPG
PTCH2 1182  PWS PA ATSSGNLSSRGPPATG

PTCH  1297  RQGQQPRRDPPREGLWPPLYRPRRDAFEISTEGHSGPSNRARWGPRGARS

PTCH  1347  HNPRNPASTAMGSSVPGYCQPITTVTASASVTVAVHPPVPGPGRNPRGG

PTCH  1397  LCPGYPETDHGLFEDPHVPFHVRCERRDSKVEVIELQDVECEERPRGSSS

PTCH  1447  N
```

FIG. 3D

|          | 10         | 20         | 30         | 40         | 50         |
|----------|------------|------------|------------|------------|------------|

```
              10         20         30         40         50
hPtch-2   MTRSPPLRELPPSYTPPARTAAPQILAGSLKAPLWLRAYFQGLLFSLGCG
           * *.  .*  **********. .**.******.*****************
mPatched2 MVRPLSLGELPPSYTPPARSSAPHILAGSLQAPLWLRAYFQGLLFSLGCR
(SEQ ID NO:7) 10         20         30         40         50

60         70         80         90        100
hPtch-2   IQRHCGKVLFLGLLAFGALALGLRMAIIETNLEQLWVEVGSRVSQELHYT
           **.**********.**********.*.***.******************
mPatched2 IQKHCGKVLFLGLVAFGALALGLRVAVIETDLEQLWVEVGSRVSQELHYT
              60         70         80         90        100

110        120        130        140        150
hPtch-2   KEKLGEEAAYTSQMLIQTARQEGENILTPEALGLHLQAALTASKVQVSLY
           *****************.*** *.******.******************
mPatched2 KEKLGEEAAYTSQMLIQTAHQEGGNVLTPEALDLHLQAALTASKVQVSLY
             110        120        130        140        150

160        170        180        190        200
hPtch-2   GKSWDLNKICYKSGVPLIENGMIEWMIEKLFPCVILTPLDCFWEGAKLQG
           *******************.*****.***********************
mPatched2 GKSWDLNKICYKSGVPLIENGMIERMIEKLFPCVILTPLDCFWEGAKLQG
             160        170        180        190        200

210        220        230        240        250
hPtch-2   GSAYLPGRPDIQWTNLDPEQLLEELGPFASLEGFRELLDKAQVGQAYVGR
           ******************.******************************
mPatched2 GSAYLPGRPDIQWTNLDPQQLLEELGPFASLEGFRELLDKAQVGQAYVGR
             210        220        230        240        250

260        270        280        290        300
hPtch-2   PCLHPDDLHCPPSAPNHHSRQAPNVAHELSGGCHGFSHKFMHWQEELLLG
           ***.*** *******.********.************************
mPatched2 PCLDPDDPHCPPSAPNRHSRQAPNVAQELSGGCHGFSHKFMHWQEELLLG
             260        270        280        290        300

310        320        330        340        350
hPtch-2   GMARDPQGELLRAEALQSTFLLMSPRQLYEHFRGDYQTHDIGWSEEQAST
           * ***  **.***************************************
mPatched2 GTARDLQGQLLRAEALQSTFLLMSPRQLYEHFRGDYQTHDIGWSEEQASM
             310        320        330        340        350
```

FIG. 8A

```
                 360        370        380        390        400
hPtch-2    VLQAWQRRFVQLAQEALPENASQQIHAFSSTTLDDILHAFSEVSAARVVG
           ****************** ******************.******..****
mPatched2  VLQAWQRRFVQLAQEALPANASQQIHAFSSTTLDDILRAFSEVSTTRVVG
                 360        370        380        390        400

410        420        430        440        450
hPtch-2    GYLLMLAYACVTMLRWDCAQSQGSVGLAGVLLVALAVASGLGLCALLGIT
           *******************.*****************************
mPatched2  GYLLMLAYACVTMLRWDCAQSQGAVGLAGVLLVALAVASGLGLCALLGIT
                 410        420        430        440        450

460        470        480        490        500
hPtch-2    FNAATTQVLPFLALGIGVDDVFLLAHAFTEALPGTPLQERMGECLQRTGT
           ********************.******** * *.*** ******. ***
mPatched2  FNAATTQVLPFLALGIGVDDIFLLAHAFTKAPPDTPLPERMGECLRSTGT
                 460        470        480        490        500

510        520        530        540        550
hPtch-2    SVVLTSINNMAAFLMAALVPIPALRAFSLQAAIVVGCTFVAVMLVFPAIL
           ** ***.*** **.***********************  *  ***** ***
mPatched2  SVALTSVNNMVAFFMAALVPIPALRAFSLQAAIVVGCNFAAVMLVFPAIL
                 510        520        530        540        550

560        570        580        590        600
hPtch-2    SLDLRRRHCQRLDVLCCFSSPCSAQVIQILPQELGDGTVPVGIAHLTATV
           ******* ******************.****** .**************
mPatched2  SLDLRRRHRQRLDVLCCFSSPCSAQVIQMLPQELGDRAVPVGIAHLTATV
                 560        570        580        590        600

610        620        630        640        650
hPtch-2    QAFTHCEASSQHVVTILPPQAHLVPPSDPLGSELFSPGGSTRDLLGQEE
           **********************..*.*********.**********.***
mPatched2  QAFTHCEASSQHVVTILPPQAHLLSPASDPLGSELYSPGGSTRDLLSQEE
                 610        620        630        640        650

660        670        680        690        700
hPtch-2    ETRQKAACKSLPCARWNLAHFARYQFAPLLLQSHAKAIVLVLFGALLGLS
           *  .***..*  **.* ***************..***.**..*******
mPatched2  GTGPQAACRPLLCAHWTLAHFARYQFAPLLLQTRAKALVLLFFGALLGLS
                 660        670        680        690        700
```

FIG. 8B

```
              710        720        730        740        750
hPtch-2   LYGATLVQDGLALTDVVPRGTKEHAFLSAQLRYFSLYEVALVTQGGFDYA
          *************************************************
mPatched2 LYGATLVQDGLALTDVVPRGTKEHAFLSAQLRYFSLYEVALVTQGGFDYA
              710        720        730        740        750

760        770        780        790        800
hPtch-2   HSQRALFDLHQRFSSLKAVLPPPATQAPRTWLHYYRNWLQGIQAAFDQDW
          ***************************************.*********
mPatched2 HSQRALFDLHQRFSSLKAVLPPPATQAPRTWLHYYRSWLQGIQAAFDQDW
              760        770        780        790        800

810        820        830        840        850
hPtch-2   ASGRITRHSYRNGSEDGALAYKLLIQTGDAQEPLDFSQLTTRKLVDREGL
          ****** ******************.****************.***
mPatched2 ASGRITCHSYRNGSEDGALAYKLLIQTGNAQEPLDFSQLTTRKLVDKEGL
              810        820        830        840        850

860        870        880        890        900
hPtch-2   IPPELFYMGLTVWVSSDPLGLAASQANFYPPPPEWLHDKYDTTGENLRIP
          *************************************************
mPatched2 IPPELFYMGLTVWVSSDPLGLAASQANFYPPPPEWLHDKYDTTGENLRIP
              860        870        880        890        900

910        920        930        940        950
hPtch-2   PAQPLEFAQFPFLLRGLQKTADFVEAIEGARAACAEAGQAGVHAYPSGSP
          .***********.*********************.**************
mPatched2 AAQPLEFAQFPFLLHGLQKTADFVEAIEGARAACTEAGQAGVHAYPSGSP
              910        920        930        940        950

960        970        980        990       1000
hPtch-2   FLFWEQYLGLRRCFLLAVCILLVCTFLVCALLLLNPWTAGLIVLVLAMMT
          ******************************.*******************
mPatched2 FLFWEQYLGLRRCFLLAVCILLVCTFLVCALLLLSPWTAGLIVLVLAMMT
              960        970        980        990       1000

1010       1020       1030       1040       1050
hPtch-2   VELFGIMGFLGIKLSAIPVVILVASVGIGVEFTVHVALGFLTTQGSRNLR
          **************************.**************..******
mPatched2 VELFGIMGFLGIKLSAIPVVILVASIGIGVEFTVHVALGFLTSHGSRNLR
              1010       1020       1030       1040       1050
```

FIG. 8C

```
              1060       1070       1080       1090       1100
hPtch-2   AAHALEHTFAPVTDGAISTLLGLLMLAGSHFDFIVRYFFAALTVLTLLGL
          ** ***.********.************.****.****  ********
mPatched2 AASALEQTFAPVTDGAVSTLLGLLMLAGSNFDFIIRYFFVVLTVLTLLGL
              1060       1070       1080       1090       1100

1110       1120       1130       1140       1150
hPtch-2   LHGLVLLPVLLSILGPPPEVIQMYKESPEILSPPAPQGGGLRWGASSSLP
          ****.**********.*.*.*****. *...*** ****. ...**
mPatched2 LHGLLLLPVLLSILGPPPQVVQVYKESPQTLNSAAPQRGGLRWDRPPTLP
              1110       1120       1130       1140       1150

1160       1170       1180       1190       1200
hPtch-2   QSFARVTTSMTVAIHPPPLPGAYIHPAPDEPPWSPAATSSGNLSSRGPGP
          ************.*********.***..**
mPatched2 QSFARVTTSMTVALHPPPLPGAYVHPASEEPT
              1160       1170       1180 hPtch-2   ATG
```

FIG. 8D

> Consensus Sequence of human patched 2 cDNA clone
> length: 4004 bp (SEQ ID NO:8)

```
  1 CCCACGCGTC CGGGAGAAGC TGGGGGAGGA GGCTGCATAC ACCTCTCAGA TGCTGATACA GACCGCACGC CAGGAGGGAG AGAACATCCT CACACCCGAA
    GGGTGCCGCAG GCCCTCTTCG ACCCCCCTCT CCGAGTATG TGGAGAGTCT ACGACTATGT CTGGCGTGCG GTCCTCCCTC TCTTGTAGGA GTGTGGGCTT
                                                          race 6                                           race 5'

101 GCACTTGGCC TCCACCTCCA GGCAGCCCTC ACTGCCAGTA AAGTCCAAGT ATCACTCTAT GGGAAGTCCT GGGATTTGAA CAAAATCTGC TACAAGTCAG
    CGTGAACCGG AGGTGGAGGT CCGTCGGGAG TGACGGTCAT TTCAGTTCA TAGTGAGATA CCCTTCAGGA CCCTAAACTT GTTTTAGACG ATGTTCAGTC

201 GAGTTCCCCT TATTGAAAAT GGAATGATTG AGCGGATGAT TGAGAAGCTG TTTCCGTGCG CCCCCCTCGA TGATCCTCAC CCCCCTCGAC TGCTTCTGGG AGGGAGCCAA
    CTCAAGGGGA ATAACTTTTA CCTTACTAAC TCGCCTACTA ACTCTTCGAC AAAGGCACGC GGGGGAGCTG ACTAGGAGTG ACGAAGACCC TCCCTCGGTT

301 ACTCCAAGCG GGCTCCGCCT ACCTGCCGCT CCCAATGTGG CTCACGAGCT GAGTGGGGGC TGCCATGGCT TCTCCCACAA ATTCATGCAC TGGCAGGAGG
    TGAGGTTCCC CCGAGCGGA GGGTTACACC ACGGTTACAC TCACCCCCG ACGGTACCGA CTCTACGAC ACGGTTACAC TAAGTACGTG ACCGTCCTCC

401 AATTGCTGCT GGGAGGCATG GCCAGAGAGA GCTGTGAGG GCAGAGGCCC CTTCTTGCTG ATGAGTCCCC GCCAGCTGTA
    TTAACGACGA CCCTCCGTAC CGGTCTCTCT CGACGACTCC CGTCTCCGGG AGTCTCTGTG GAAGAACGAC TACTCAGGGG CGGTCGACAT

501 CGAGCATTTC CGGGGTGACT ATCAGACACA TGACATTGGC TGGAGTGAGG AGCAGGCCAG CACAGTGCTA CACCCTGTTT TGTGCAGGTC
    GCTCGTAAAG GCCCCACTGA TAGTCTGTGT ACTGTAACCG ACCTCACTCC TCGTCCGGAT GTGTCACGAT CGGGACCGA CACGTCCAG

601 GGTATGGACA AGGACAGGGG GGTGCCCTGA GGCCATTCCC TCCTCCTGCC CCCTCCTATC CACCCCTGTT CTCCAGCTGG CCCAGGAGGC CCTGCCTGAG
    CCATACCTGT TCCTGTCCCC CCACGGGACT CCGGTAAGGG AGGAGACGG GGGAGGATAG GTGGGACAAA GAGGTCGACC GGGTCCTCCG GGACGGACTC

701 AAGCCTTCCC AGCAGATCCA TGCCTTTCTC TCCACCACCC TGGATGACAT CCTGCATGCG TTCTCTGAAG TCAGTGCTGC CCGTGTGGTG GGAGGCTATC
    TTGCGAAGGG TCGTCTAGGT ACGGAAGAGG AGGTGGTGGG ACCTACTGTA GGACGTACGC AAGAGACTTC AGTCACGACG GGCACACCAC CCTCCGATAG

801 TGCTCCATGGT GGTCTTGCA CCTGGCACCT TGCCCCCACC CCACTTCCAA CCAGTGCCCA CCCTGGGGAG TGCCCTTTCC CCCACACGCT
    ACGAGTACCA CCCAGAAGGG TCGTCTAGGT ACGGGAACGT ACGGGGGTGG GGTGAAGGTT GGTCACGGGT GGGACCCCTC GGGGACTCTG ACGGGAAAGG GGGTGTCGA
```

FIG. 10A

```
 901 GGCCTATGCC TGTGTGACCA TGCTGCGGTG GGACTGCGCC CAGTCCCAGG GTTCCGTGGG CCTTGCCGGG GTACTGCTGG TGGCCCTGCC GGTGGCCTCA
     CCGGATACGG ACACACTGGT ACGACGCCAC CCTGACGCGG GTCAGGGTCC CAAGGCACCC GGAACGGCCC CATGACGACC ACCGGGACCG CCACCGGAGT

1001 GGCCTTGGGC TCTGTGCCCT GCTCGGCATC ACCTTCAATG CTGCCACTAC CCAGGTACGC CAGGACTGCA GGGCAGACTC AGTGCCAGTC ACCAGGCTTC
     CCGGAACCCG AGACACGGGA CGAGCCGTAG TGGAAGTTAC GACGGTGATG GGTCCATGCG GTCCTGACGT CCCTGTGAGT TCACGGTCAG TGGTCCGAAG

1101 ACGGGTCCTC AGTGCCCGC TCCTCTGCCC CTCCAGGTGC TGCCCTTCTT GACTCTGGGA ATCGGCGTGG ATGACGTATT CCTGCTGGCG CATGCCTTCA
     TGCCCAGGAG TCGACGGGCG AGGAGACGGG AGGTCCACG ACGGAAGAA CTGAGACCCT TAGCCGCACC TACTGCATAA GGACGACCGC GTACGGAAGT

1201 CAGAGGCTCT GCCTGGCACC CCTCTCCAGG TGGGGCCTTG CTCATCTGAG GCAGTCCAGC TTACTGGTTA AGAGCCTCTT GGTTCAAGTG
     GTCTCCGAGA CGGACCGTGG GGAGAGTCC ACCCCGGAAC AGGGGTCCC GAGTAGACTC CGTCGAGTCG AATGACCAAT TCTCGGAGAA CCAAGTTCAC

1301 ACCTTGGGCT GCTAATGAAC CTCGGTGCCT CTTGTCCCCA TGTGTAAACA GGGGAAATAA TAGTGCTGTG TCCTAAGGGT TATTGTTTGG ATCAGTGAAG
     TGGAACCCGA CGATTACTTG GAGCCACGGA GAACAGGGGT ACACATTTGT CCCCTTTATT ATCACGACAC AGGATTCCCA ATAACAAACC TAGTCACTTC

1401 TAACTCAAGT TGAATGCTTA GAACAGCCCA TCATACGTAC ATAAATGCTA GCCACTGTGT TATGACTGCC CCACCTCTGC ACCCCAAGTT
     ATTGAGTTCA ACTTACGAAT CTTGTCGGGT AGTATGCATG TATTTACGAT CGGTGACACA ATACTGACGG GGTGGAGACG TGGGGTTCAA

1501 CCTGAGCCTC CCCTTCACTC CACTTTGACA CGGCCCCTCC CTTGTGACCT GAGGCAGGT CCCCACTCTG TCCTGGCAGG AGCGCATGGG CGAGTGTCTG
     GGACTCGGAG GGGAAGTGAG GTGAAACTGT GCCGGGGAGG GAACACTGGA CTCCGTCCA GGGGTGAGAC AGGACCGTCC TCGCGTACCC GCTCACAGAC

1601 CAGGCGACGG GCACCAGTGT TGTACTCACA TCCATCAACA GGGCCACTGC CAGCGCCTTG ATGTGCTCTG CTGCTTCTCC AGTACTGCC TGCGCCCCAG GCCTTCTCC
     GTCGCGTGCC CGTGGTCACA ACATGAGTGT AGGTAGTTGT GTCGCGGAAC GACGAGAGG TCCATGACGG AAGGTAGGG ACGCGACGCT CGGAAGAGGG

1701 TACAGCCTGG ACCTACGGCG GCGCCACTGC CAGCGCCTTG CTGCTTCTCC GACGAAGAGG TCCATGACGG TTCCATCCC AGGTGATTCA GATCCTGCCC
     ATGTCGGACC TGGATGCCGC CGCGGTGACG GTCGCGGAAC GACGAAGAGG AAGGTAGGG ACGCGACGCT CGGAAGAGGG ACGCGGGGTC GGGAAGGAG

1801 CGCCAGCCTG TCCCCTCACC AGCATTTCAA GGCACAGACC TGTCATCCAC TCTCTACCTC TTCCAGTCCC TGCTCTGCTC AGTTGATTCA GATCCTGCCC
     GCGGTCGGAC AGGGAGTGG TCGTAAGTT CCGTGTCTGG ACAGTAGGTG AGAGATGGAG AAGGTCAGG ACGAGACGAG TCAACTAAGT CTAGGACGGG

1901 CAGGAGCTGG GGGACGGGAC AGTACCAGTG GGCATTGCCC ACCTCACTGC CACAGTTCAA GCCTTTACCC ACTGTGAAGC CAGCAGCCAG CATGTGGTCA
     GTCCTCGACC CCCTGCCCTG TCATGGTCAC CCGTAACGGG TGGAGTGACG GTGTCAAGTT CGGAAATGGG TGACACTTCG GTCGTCGGTC GTACACCAGT

2001 CCATCCTGCC TCCCAAGCC CACCTGTGTC CCCCACCTTC GGCTCTGAGC TCTTCAGCCC TGGAGGGTCC ACACGGGACC TTCTAGGCCA
     GGTAGGACGG AGGGTTCGG GTGGACCACG GGGGTGGAAG CCGAGACTCG AGAAGTCGGG ACCTCCCAGG TGTGCCCTGG AAGATCCGGT
```

FIG. 10B

```
2101  GGAGGAGGAG ACAAGGCAGA AGGCAGCCTG CAAGTCCCTG CCCTGTGCCC GCTGGAATCT TGCCCATTTC GCCCGCTATC AGTTTGCCCC GTTGCTGCTC
      CCTCCTCCTC TGTTCCGTCT TCCGTCGGAC GTTCAGGGAC GGGACACGGG CGACCTTAGA ACGGGTAAAG CGGGCGATAG TCAAACGGGG CAACGACGAG

2201  CAGTCACATG CCAAGGCCAT CGTGCTGGTG CTCTTTGGTG CCTTTCTGGG CTGAGCCCTC TACGGAGCCA CCTTGGTGCA AGACGGCCTG GCCCTGACGG
      GTCAGTGTAC GGTTCCGGTA GCACGACCAC GAGAAACCAC GGACTCGGAG ATGCCTCGGT GGAACCACGT TCTGCCGGAC CGGGACTGCC

2301  ATGTGGTGCC TCGGGGCACC AAGGAGCATG CCTTCCTGAG CGCCCAGCTC AGGTACTTCT CCCTGTACGA GGTGGCCCTG GTGACCCAGG GTGGCTTTGA
      TACACCACGG AGCCCCGTGG TTCCTCGTAC GGAAGGACTC GCGGGTCGAG TCCATGAAGA GGGACATGCT CCACCGGGAC CACTGGGTCC CACCGAAACT

2401  CTACGCCCAC TCCCAACGCG CCCTCTTTGA TCTGCACCAG CCCTTCAGTT CCCTCAAGGC GGTGCTGCCC CCACCGGCCA CCCAGGCACC CCGCACCTGG
      GATGCGGGTG AGGGTTGCGC GGGAGAAACT AGACGTGGTC GGGAAGTCAA GGGAGTTCCG CCACGACGGG GGTGGCCGGT GGGTCCGTGG GGCGTGGACC

2501  CTGCACTATT ACCGCAACTG GCTACAGGGA ATCCAGGCTG CCTTTGACCA GGACTGGGCT TCTGGGCGCA CTCGTACCGC AATGGCTCTG
      GACGTGATAA TGGCGTTGAC CGATGTCCCT TAGGTCCGAC GGAAACTGGT CCTGACCCGA AGACCCGCGT AGTGGGCGGT GAGCATGGCG TTACGAGAC

2601  AGGATGGGGC CCTGGCCTAC AAGCTGCTCA TCCAGACTGG AGACGCCCAG GAGCCTCTGG ATTTCAGCCA GGTTGGGAGA GGGCTGGAGG GGTCCACTAG
      TCCTACCCCG GGACCGGATG TTCGACGAGT AGGTCTGACC TCTGCGGGTC CTCGGAGACC TAAAGTCGGT CCAACCCTCT CCCGACCTCC CCAGGTGATC

2701  TACAGGGGCT GCAGGCCTCC TGGGCCCAGG CCTTCAGCCC TCTCTGCCTC TGCAGCTGAC CACAAGGAAG CTGGTGGACA GAGAGGGACT GATTCCACCC
      ATGTCCCCGA CGTCCGGAGG ACCCGGGTCC GGAAGTCGGG AGAGACGGAG ACGTCGACTG GTGTTCCTTC GACCACCTGT CTCTCCCTGA CTAAGGTGGG

2801  GAGCTCTTCT ACATGGGGCT GACCGTGTGG GTGAGCAGTG TCTGGCAGCC ACCCCCTGGG ACTTCTACCC CCCACCTCCT GAATGGCTGC
      CTCGAGAAGA TGTACCCCGA CTGGCACACC CACTCGTCAC AGACCGTCGG TGGGGGACCC TGAAGATGGG GGGTGGAGGA CTTACCGACG

2901  ACGACAAATA CGACACCACG GGGAGAAACC TTCGCAGTGA GTCTTGGGGG GAGCTCGGCA AGAGCCTCAG CCTCGCCCAC ACAAGCCCTG AGCCTGAGGC
      TGCTGTTTAT GCTGTGGTGC CCCCTCTTGG AAGCGTCACT CAGAACCCCC CTCGAGCCGT TCTCGGAGTC GGAGCGGGTG TGTTCGGGAC TCGGACTCCG

3001  CCTGCCCACT CTGCCCCGTG CTCACCGCCC TGTCCCTCTC CCTCTTCTCC CTTCCCTCCC CCGCCCAGT CCCGCCCAGC CAGCCCTTGG AGTTTGCCCA
      GGACGGGTGA GACGGGGCAC GAGTGGCGGG ACAGGGAGAG GGAAGAGAGG GAAGGGAGGG GGCGGGTCA GGGCGGGTCG GTCGGGAACC TCAAACGGGT
```

FIG. 10C

```
3101 GTTCCCCTTC CTGCTGCGTG GCCTCCAGAA GACTGCAGAC TTTGTGGAGG CCATGAGGG GCCCGGGCA GCATGGCGCA GGCCCGGGCA GGCTGGGGTG
     CAAGGGGAAG GACGACGCAC CGGAGGTCTT CTGACGTCTG AAACACCTCC GGTAGCTCCC CGGGCCCCGT CGTACGCGTC TCCGGCCCGT CCGACCCCAC

3201 CACGCCTACC CCAGCGGCTC CCCCTTCCTC TTCTGGGAAC AGTATCTGGG CCTGCGGCGC TGCTTCCTGC ACCGGCAGAC GTAGGACGAC CACACGTGAA
     GTGCGGATGG GGTCGCCGAG AAGACCCTTG TCATAGACCC GGACGCCGCG ACGAAGGACG ACGGCAGAC GTAGGACGAC CACACGTGAA

3301 TCCTCGTCTG TGCTTCTGTG CTCCTCAACC CCTGGACCGC TGGCCTCATA GTGAGTGCTT GCAGGAGTGG GGACAGAGAC ACCCCACCCT TCCCTGCCA
     AGGAGCAGAC ACGAGACGAC GAGGAGTTGG GGACCTGCCG ACCGGAGTAT CACTCACGAA CGTGTCTCTG TGGGGTGGGA AGGGACGGGT

3401 GCCTGTCATC CCTCCTGCCA GGAGCCCTCT GTGAGCCCTG TCTCCCTCAG GTGCTGGTCC TGGCGATGAT GACAGTGGAA CTCTTTGGTA TCATGGGTTT
     CGGACAGTAG GGAGGACGGT CCTCGGGAGA CACTCGGGAC AGAGGGAGTC CACGACCAGG ACCGCTACTA CTGTCACCTT GAGAAACCAT AGTACCCAAA

3501 CCTGGGCATC AAGCTGAGTG GGTGATCCCT GTGGCCCTCG TAGGCATTGG CGTTGAGTTC ACAGTCCACG TGGCTCTGT GAGCACGGGC
     GGACCCGTAG TTCGACTCAC CCACTAGGGA CACCGGGAGAA ATCCGTAACC GCAACTCAAG TGTCAGGTGC ACCGAGACCA CTCGTGCCCG

3601 ACCCGGGGA GGGACCAATC AGTCGATTCA GTATTCAACA CATATTGTTC AAGCCCCTAC TATGTGCTAG AGAATTTGGG CTGGGTGGAC
     TGGGGCCCCT CCCTGGTTAG TCGACTAAGT CATAAGTTGT GTATACAAG TTCGGGGATG ATACACGATC CATGATAAAT TCTTAAACCC GACCCACCTG

3701 GTGGTGGCTC ATTCCTGTAA TCCCAGCACT TTGGGAGGCC GAGGCGGGTG GATCACCTGA GGTCGGGAGT CCTGGCCAAC ATGGTGAAAC
     CACCACCGAG TAAGGACATT AGGGTCGTGA AACCCTCCGG CTCCGCCCAC CTAGTGGACT CCAGCCCTCA AGCTTTGGTC GGACCGGTTG TACCACTTTG

3801 CCTGTCTTA CTAAAAATAC AAAAAATTAG CCAGGCGTGG TGGCACATGC CAGTAGTCCC AGCTACTTTG GAGGCTGAGG CAGAATTGCT TGAACCTGGG
     GGACAGAAAT GATTTTTATG TTTTTAATC GGTCCGCACC ACCGTGTACG GTCATCAGGG TCGATGAAAC CTCCGACTCC GTCTTAACGA ACTTGGACCC

3901 AGGCGAAGGT TGCAGTGAGC TGAGATCGTG CCATTGCACT CCAGCCTGGG CAACAAGAGT GCAACTCTCC GTCTCAAAAA AAAAAAAAAA AAGGGCGGCC
     TCCGCTTCCA ACGTCACTCG ACTCTAGCAC GGTAACGTGA GGTCGGACCC GTTGTTCTCA CGTTGAGAGG CAGAGTTTTT TTTTTTTT TTCCCGCCGG

4001 GCGA
     CGCT
```

FIG. 10D

Clone 16.1 human patched 2
> length: 2082 bp

> (SEQ ID NO:9)

```
  1 TTCCGGCATG ACTCGATCGC CGCCCCTCAG AGAGCTGCCC CCGAGTTACA CACCCCCAGC TGGAACCGCA GCACCCCAGA TCCTAGCTGG GAGCCTGAAG
    AAGGGCCTAC TGAGCTAGCG GCGGGGAGTC TCTCGACGGG GGCTCAATGT GTGGGGGTCG AGCTTGGCGT CAGAGACATT GTGGCAAAGT GCTCTTTCTG GGACTGTTGG

101 GCTCCACTCT GGCTTGTGC TTACTTCCAG CCTGCTCT TCTCTCTGGG ATGCGGGATC TACGCCCTAG AGAGACCC GTCTCTGTAA CACCCGTTCA CGAGAAAGAC CCTGACAACC
    CGAGGTGAGA CCGAAGCACG AATGAAGGTC CGGACGAGA AGAGAGACCC TACGCCCTAG AGAGACCC GTCTCTGTAA CACCCGTTCA CGAGAAAGAC CCTGACAACC

201 CCTTTGGGGC CCTGGCATTA GGTCTCCGCA TGGCCATTAT TGAGACAGC TTGGAACAGC TCTGGGTAGA AGTGGGCAGC CGGGTGAGCC AGGAGCTGCA
    GGAAACCCCG GGACCGTAAT CCAGAGGCGT ACCGGTAAT ACTCTGTTTG AACCTTGTCG AGACCCATCT TCACCCGTCG GCCCACTCGG TCCTCGACCT

301 TTACACCAAG GAGAAGCTGG GGGAGGAGGC TGCATACACC TCTCAGATGC TGATACAGAC CGCACGCCAG GAGGGAGAGA ACATCCTCAC ACCGAAGCA
    AATGTGGTTC CTCTTCGACC CCCTCCTCCG ACGTATGTGG AGAGTCTACG ACTATGTCTG GCGTGCGGTC CTCCCTCTCT TGTAGGAGTG TGGGCTTCGT

401 CTTGGCCTCC ACCTCCAAGC AGCCCTCACT GCCAGTAAAG TCCAAGTATC ACTCTATGGG AAGTCCTGGG ATTTGAACAA AATCTGCTAC AAGTCAGGAG
    GAACCGGAGG TGGAGGTCCG TCGGGAGTGA CGGTCATTTC AGGTTCATAG TGAGATACCC TTCAGGACCC TAAACTTGTT TTAGACGATG TTCAGTCCTC

501 TTCCCCTTAT TGAAAATGGA ATGATTGAGT CCTACTAACT CGTGCGTGTT CGGTCGTGA AAGTCCTGCG CCTCGACTGC TTCTGGAGG GAGCAAACT
    AAGGGAATA ACTTTTACCT TACTAACTCA GGCAGGACT CTTCGACAAA GCCACGCACT AGGAGTGGGG GGAGCTGACG AAGACCCTCC CTCGGTTGA

601 CCAAGGGGGC TCCGCTACC TGCCCGGCCG CCCGATATC CAGTGGACCA ACCTGGACTG AGAGCAGCTG CTGGAGGAGC TGGGTCCCTT TGCCTCCCTT
    GGTTCCCCCG AGGCGGATGG ACGGGCCGGC GGGCTATAG GTCACCTGGT TGGACCTGAC TCTCGTCGAC GACCTCCTCG ACCCAGGGAA ACGGAGGGAA

701 GAGGGCTTCC GGGAGCTGCT AGACAAGGCA CAGGTGGGCC AGGCCTACGT TGGCACCTCT GGGGCGGCC TGTCTGCACC CTGATGACCT CCACTGCCCA CCTAGTGCCC
    CTCCCGAAGG CCCTCGACGA TCTGTTCCGT GTCCACCCGG TCCGGATGCA CCCCGCCGGG ACAGACGTGG GACTACTGGA GGATCACGGG

801 CCAACCATCA CAGCAGGCAG GCTCCAATG TGGCTCACGA GCTGAGTGGG GGCTGCCATG CCGACGGTAC CAAATTCATG GCTTCTCCCA CACTGGCAGG AGGAATTGCT
    GGTTGGTAGT GTCGTCCGTC CGAGGGTTAC ACCGAGTGCT CGACTCACCC CCGACGGTAC CAAATTCATG GCTTCTCCCA CACTGGCAGG TCCTTAACGA

901 GCTGGGAGGC ATGGCCAGAG ACCCCAAGG AGAGCTGCTG AGGGCAGAGG CCCTGCAGAG CCCTGCAGAG CACCTTCTTG CTGATGAGTC CCCGCCAGCT GTACGAGCAT
    CGACCCTCCG TACCGGTCTC TGGGGTTCC TCTCGACGAC AGGGCAGAGG TCCCGTCTCC GGACGTCTC GTGGAAGAAC GACTACTCAG GGGCGGTCGA CATGCTCGTA
```

FIG. 11A

```
1001  TTCCGGGGTG ACTATCAGAC ACATGACATT GGCTGGAGTG AGGAGCAGGC CAGCACAGTG CTACAAGCCT GGCAGCGCGC CTTTGTGCAG CTGGCCCAGG
      AAGGCCCCAC TGATAGTCTG TGTACTGTAA CCGACCTCAC TCCTCGTCCG CGTCGTGTCAC GATGTTCGGA CCGTCGCCGC GAAACACGTC GACCGGGTCC

1101  AGGCCCTGCC TGAGAACGCT TCCCAGCAGA TCCATGCCTT CTCCTCCACC ACCCTGGATA ACATCCTGCA TGCGTTCTCT GAAGTCAGTG CTGCCCGTGT
      TCCGGGACGG ACTCTTGCGA AGGGTCGTCT AGGTACGGAA GAGGAGGTGG TGGGACCTAT TGTAGGACGT ACGCAAGAGA CTTCAGTCAC GACGGGCACA

1201  GGTGGGAGGC TATCTGCTCA TGCTGGCCTA ACCATGCTGC GGTGGGACTG CGCCCAGTCC CAGGGTTCCG TGGGCCTTGC CGGGTACTG
      CCACCCTCCG ATAGACGAGT ACGACCGGAT TGGTACGACG CCACCCTGAC GCGGGTCAGG GTCCCAAGGC ACCCGAAACG GCCCATGAC

1301  CTGGTGGCCC TGGGGTGGC CTCAGGCCTT CCCTGCTCGTG CATCACCTTC AATGCTGCCA CTACCCAGGT GCTGCCCTTC TTTGGCTCTGG
      GACCACCGGG ACCGCCACCG GAGTCCGGAA GGGACGAGAC GTAGTGGAAG TTACGACGGT GATGGGTCCA CGACGGGAAG AACCGAGACC

1401  GAATCGGCGT GGATGACGTA TTCCTGCTGG CGCATGCCTT CACAGAGGCT CCCCTCTGGCA GGAGCGCATG GGCGAGTGTC TGCAGCGCAC
      CTTAGCCGCA CCTACTGCAT AAGGACGACC GCGTACGGAA GTGTCTCCGA GGGGAGAGGT CCTGCGTAC CCGCTCACAG ACGTCGCGTG

1501  GGGCACCAGT GTCGTACTCA CATCCATCAA GCCTTCCTCA TGGCTGCCCT CGTTCCCATC CCTGCCTCTC GAGCCTTCTC CTTACAGCCA
      CCCGTGGTCA CAGCATGAGT GTAGGTAGTT GTTGTACCGG ACCGACGGGA GCAAGGGTAG GGACGCGACG CTCGGAAGAG GAATGTCGGT

1601  TCCTCAGCCT CGGCGCCACT GCCAGCGCCT CATTGCCCAC TGATGTGCTC TGCTGCTTCT CCAGTCCCTG GTGATTCAGA TCCTGCCCCA
      AGGAGTCGGA CCTGCGGTGA CGGTCGCGGA GTAACGGGTG ACTACACGAG ACGACGAAGA GGTCAGGGAC CACTAAGTCT AGGACGGGGT

1701  GGAGCTGGGG GACGGGACAG TACCAGTGGG CCACCACTGG CAGTTCAAGC CTCTGAGCTC TTCAGCCCTG GAGGGTCCAC ACGGGACCTT CTAGGCCAGG
      CCTCGACCCC CTGCCCTGTC ATGGTCACCC GGTGGTGACC GTCAAGTTCG GAGACTCGAG AAGTCGGGAC CTCCCAGGTG TGCCCTGGAA GATCCGGTCC

1801  ATCCTGCCTC CCCAAGCCCA CCTGGTGCCC AGTCCCCTGCC CTGTGCCCGC TGGAATCTTG CCCGGAATTC CTGCAGCCCG GGGATCCAC
      TAGGACGGAG GGGTTCGGGT GGACCACGGG TCAGGGGACGG GACACGGGCG ACCTTAGAAC GGGCCTTAAG GACGTCGGGC CCCTAGGTG

1901  AGGAGGAGAC AAGGCAGAAG GCAGCCTGCA AGTCCCCTGCA AAGGCAGAAG GCAGCCTGCA AGTCCCCTGCC CTGTGCCCGC TGGAATCTTG CCCGGAATTC
      TCCTCCTCTG TTCCGTCTTC CGTCGGACGT TCAGGGACGT TTCCGTCTTC CGTCGGACGT TCAGGGACGT GACACGGGCG ACCTTAGAAC GGGCCTTAAG

2001  TAGTTCTAGA GCGGCCGCCA CCGGGGTGGA GCTCCAGCTT TTGTTCCCTT TAGTGAGGGT TAATTGCGCG CTTGGGTATC TT
      ATCAAGATCT CGCCGGCGGT GGCCCCACCT CGAGGTCGAA AACAAGGGAA ATCACTCCCA ATTAACGCGC GAACCCATAG AA
```

FIG. 11B

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 4030 base pairs
      (B) TYPE: Nucleic Acid
      (C) STRANDEDNESS: Single
      (D) TOPOLOGY: Linear (xi) SEQUENCE DESCRIPTION: SEQ ID NO:1:

```
GTTATTTCAG GCCATGGTGT TGCGCCGAAT TAATTCCCGA TCCAGACATG          50

ATAAGATACA TTGATGAGTT TGGACAAACC ACAACTAGAA TGCAGTGAAA         100

AAAATGCTTT ATTTGTGAAA TTTGTGATGC TATTGCTTTA TTTGTAACCA         150

TTATAAGCTG CAATAAACAA GTTGGGCCAT GGCGGCCAAG CTTCTGCAGG         200

TCGACTCTAG AGGATCCCCG GGAATTCCG GCATGACTCG ATCGCCGCCC          250

CTCAGAGAGC TGCCCCCGAG TTACACACCC CCAGCTCGAA CCGCAGCACC         300

CCAGATCCTA GCTGGGAGCC TGAAGGCTCC ACTCTGGCTT CGTGCTTACT         350

TCCAGGGCCT GCTCTTCTCT CTGGGATGCG GGATCCAGAG ACATTGTGGC         400

AAAGTGCTCT TTCTGGGACT GTTGGCCTTT GGGGCCCTGG CATTAGGTCT         450

CCGCATGGCC ATTATTGAGA CAAACTTGGA ACAGCTCTGG GTAGAAGTGG         500

GCAGCCGGGT GAGCCAGGAG CTGCATTACA CCAAGGAGAA GCTGGGGGAG         550

GAGGCTGCAT ACACCTCTCA GATGCTGATA CAGACCGCAC GCCAGGAGGG         600

AGAGAACATC CTCACACCCG AAGCACTTGG CCTCCACCTC CAGGCAGCCC         650

TCACTGCCAG TAAAGTCCAA GTATCACTCT ATGGGAAGTC CTGGGATTTG         700

AACAAAATCT GCTACAAGTC AGGAGTTCCC CTTATTGAAA ATGGAATGAT         750

TGAGTGGATG ATTGAGAAGC TGTTTCCGTG CGTGATCCTC ACCCCCCTCG         800

ACTGCTTCTG GGAGGGAGCC AAACTCCAAG GGGGCTCCGC CTACCTGCCC         850

GGCCGCCCGG ATATCCAGTG GACCAACCTG GATCCAGAGC AGCTGCTGGA         900

GGAGCTGGGT CCCTTTGCCT CCCTTGAGGG CTTCCGGGAG CTGCTAGACA         950

AGGCACAGGT GGGCCAGGCC TACGTGGGGC GGCCCTGTCT GCACCCTGAT        1000

GACCTCCACT GCCCACCTAG TGCCCCCAAC CATCACAGCA GGCAGGCTCC        1050

CAATGTGGCT CACGAGCTGA GTGGGGGCTG CCATGGCTTC TCCCACAAAT        1100

TCATGCACTG GCAGGAGGAA TTGCTGCTGG GAGGCATGGC CAGAGACCCC        1150

CAAGGAGAGC TGCTGAGGGC AGAGGCCCTG CAGAGCACCT TCTTGCTGAT        1200

GAGTCCCCGC CAGCTGTACG AGCATTTCCG GGGTGACTAT CAGACACATG        1250

ACATTGGCTG GAGTGAGGAG CAGGCCAGCA CAGTGCTACA AGCCTGGCAG        1300

CGGCGCTTTG TGCAGCTGGC CCAGGAGGCC CTGCCTGAGA ACGCTTCCCA        1350

GCAGATCCAT GCCTTCTCCT CCACCACCCT GGATGACATC CTGCATGCGT        1400

TCTCTGAAGT CAGTGCTGCC CGTGTGGTGG GAGGCTATCT GCTCATGCTG        1450

GCCTATGCCT GTGTGACCAT GCTGCGGTGG GACTGCGCCC AGTCCCAGGG        1500

TTCCGTGGGC CTTGCCGGGG TACTGCTGGT GGCCCTGGCG GTGGCCTCAG        1550
```

-continued

```
GCCTTGGGCT CTGTGCCCTG CTCGGCATCA CCTTCAATGC TGCCACTACC      1600
CAGGTGCTGC CTTTCTTGGC TCTGGGAATC GGCGTGGATG ACGTATTCCT      1650
GCTGGCGCAT GCCTTCACAG AGGCTCTGCC TGGCACCCCT CTCCAGGAGC      1700
GCATGGGCGA GTGTCTGCAG CGCACGGGCA CCAGTGTCGT ACTCACATCC      1750
ATCAACAACA TGGCCGCCTT CCTCATGGCT GCCCTCGTTC CCATCCCTGC      1800
GCTGCGAGCC TTCTCCCTAC AGGCGGCCAT AGTGGTTGGC TGCACCTTTG      1850
TAGCCGTGAT GCTTGTCTTC CCAGCCATCC TCAGCCTGGA CCTACGGCGG      1900
CGCCACTGCC AGCGCCTTGA TGTGCTCTGC TGCTTCTCCA GTCCCTGCTC      1950
TGCTCAGGTG ATTCAGATCC TGCCCCAGGA GCTGGGGGAC GGGACAGTAC      2000
CAGTGGGCAT TGCCCACCTC ACTGCCACAG TTCAAGCCTT TACCCACTGT      2050
GAAGCCAGCA GCCAGCATGT GGTCACCATC CTGCCTCCCC AAGCCCACCT      2100
GGTGCCCCCA CCTTCTGACC CACTGGGCTC TGAGCTCTTC AGCCCTGGAG      2150
GGTCCACACG GGACCTTCTA GGCCAGGAGG AGGAGACAAG GCAGAAGGCA      2200
GCCTGCAAGT CCCTGCCCTG TGCCCGCTGG AATCTTGCCC ATTTCGCCCG      2250
CTATCAGTTT GCCCCGTTGC TGCTCCAGTC ACATGCCAAG GCCATCGTGC      2300
TGGTGCTCTT TGGTGCTCTT CTGGGCCTGA GCCTCTACGG AGCCACCTTG      2350
GTGCAAGACG GCCTGGCCCT GACGGATGTG GTGCCTCGGG GCACCAAGGA      2400
GCATGCCTTC CTGAGCGCCC AGCTCAGGTA CTTCTCCCTG TACGAGGTGG      2450
CCCTGGTGAC CCAGGGTGGC TTTGACTACG CCCATTCCCA ACGCGCCCTC      2500
TTTGATCTGC ACCAGCGCTT CAGTTCCCTC AAGGCGGTGC TGCCCCCACC      2550
GGCCACCCAG GCACCCCGCA CCTGGCTGCA CTATTACCGC AACTGGCTAC      2600
AGGGAATCCA GGCTGCCTTT GACCAGGACT GGGCTTCTGG GCGCATCACC      2650
CGCCACTCGT ACCGCAATGG CTCTGAGGAT GGGGCCCTGG CCTACAAGCT      2700
GCTCATCCAG ACTGGAGACG CCCAGGAGCC TCTGGATTTC AGCCAGCTGA      2750
CCACAAGGAA GCTGGTGGAC AGAGAGGGAC TGATTCCACC CGAGCTCTTC      2800
TACATGGGGC TGACCGTGTG GGTGAGCAGT GACCCCCTGG GTCTGGCAGC      2850
CTCACAGGCC AACTTCTACC CCCCACCTCC TGAATGGCTG CACGACAAAT      2900
ACGACACCAC GGGGGAGAAC CTTCGCATCC CGCCAGCTCA GCCCTTGGAG      2950
TTTGCCCAGT TCCCCTTCCT GCTGCGTGGC CTCCAGAAGA CTGCAGACTT      3000
TGTGGAGGCC ATCGAGGGGG CCCGGGCAGC ATGCGCAGAG GCCGGCCAGG      3050
CTGGGGTGCA CGCCTACCCC AGCGGCTCCC CCTTCCTCTT CTGGGAACAG      3100
TATCTGGGCC TGCGGCGCTG CTTCCTGCTG GCCGTCTGCA TCCTGCTGGT      3150
GTGCACTTTC CTCGTCTGTG CTCTGCTGCT CCTCAACCCC TGGACGGCTG      3200
GCCTCATAGT GCTGGTCCTG GCGATGATGA CAGTGGAACT CTTTGGTATC      3250
ATGGGTTTCC TGGGCATCAA GCTGAGTGCC ATCCCCGTGG TGATCCTTGT      3300
GGCCTCTGTA GGCATTGGCG TTGAGTTCAC AGTCCACGTG GCTCTGGGCT      3350
TCCTGACCAC CCAGGGCAGC CGGAACCTGC GGGCCGCCCA TGCCCTTGAG      3400
CACACATTTG CCCCCGTGAC CGATGGGGCC ATCTCCACAT TGCTGGGTCT      3450
GCTCATGCTT GCTGGTTCCC ACTTTGACTT CATTGTAAGG TACTTCTTTG      3500
```

| | |
|---|---|
| CGGCGCTGAC AGTGCTCACG CTCCTGGGCC TCCTCCATGG ACTCGTGCTG | 3550 |
| CTGCCTGTGC TGCTGTCCAT CCTGGGCCCG CCGCCAGAGG TGATACAGAT | 3600 |
| GTACAAGGAA AGCCCAGAGA TCCTGAGTCC ACCAGCTCCA CAGGGAGGCG | 3650 |
| GGCTTAGGTG GGGGGCATCC TCCTCCCTGC CCAGAGCTT TGCCAGAGTG | 3700 |
| ACTACCTCCA TGACCGTGGC CATCCACCCA CCCCCCCTGC CTGGTGCCTA | 3750 |
| CATCCATCCA GCCCCTGATG AGCCCCCTTG GTCCCCTGCT GCCACTAGCT | 3800 |
| CTGGCAACCT CAGTTCCAGG GGACCAGGTC CAGCCACTGG GTGAAAGAGC | 3850 |
| AGCTGAAGCA CAGAGACCAT GTGTGGGCG TGTGGGGTCA CTGGGAAGCA | 3900 |
| CTGGGTCTGG TGTTAGACGC AGGACGGACC CCTGGAGGGC CCTGCTGCTG | 3950 |
| CTGCATCCCC TCTCCCGACC CAGCTGTCAT GGGCCTCCCT GATATCGAAT | 4000 |
| TCAATCGATA GAACCGAGGT GCAGTTGGAC | 4030 |

(2) INFORMATION FOR SEQ ID NO:2:

(i) SEQUENCE CHARACTERISTICS:
        (A) LENGTH: 1203 amino acids
        (B) TYPE: Amino Acid
        (D) TOPOLOGY: Linear (xi) SEQUENCE DESCRIPTION: SEQ ID NO:2:

```
Met Thr Arg Ser Pro Pro Leu Arg Glu Leu Pro Pro Ser Tyr Thr
 1               5                  10                  15

Pro Pro Ala Arg Thr Ala Ala Pro Gln Ile Leu Ala Gly Ser Leu
                20                  25                  30

Lys Ala Pro Leu Trp Leu Arg Ala Tyr Phe Gln Gly Leu Leu Phe
                35                  40                  45

Ser Leu Gly Cys Gly Ile Gln Arg His Cys Gly Lys Val Leu Phe
                50                  55                  60

Leu Gly Leu Leu Ala Phe Gly Ala Leu Ala Leu Gly Leu Arg Met
                65                  70                  75

Ala Ile Ile Glu Thr Asn Leu Glu Gln Leu Trp Val Glu Val Gly
                80                  85                  90

Ser Arg Val Ser Gln Glu Leu His Tyr Thr Lys Glu Lys Leu Gly
                95                  100                 105

Glu Glu Ala Ala Tyr Thr Ser Gln Met Leu Ile Gln Thr Ala Arg
                110                 115                 120

Gln Glu Gly Glu Asn Ile Leu Thr Pro Glu Ala Leu Gly Leu His
                125                 130                 135

Leu Gln Ala Ala Leu Thr Ala Ser Lys Val Gln Val Ser Leu Tyr
                140                 145                 150

Gly Lys Ser Trp Asp Leu Asn Lys Ile Cys Tyr Lys Ser Gly Val
                155                 160                 165

Pro Leu Ile Glu Asn Gly Met Ile Glu Trp Met Ile Glu Lys Leu
                170                 175                 180

Phe Pro Cys Val Ile Leu Thr Pro Leu Asp Cys Phe Trp Glu Gly
                185                 190                 195

Ala Lys Leu Gln Gly Gly Ser Ala Tyr Leu Pro Gly Arg Pro Asp
                200                 205                 210

Ile Gln Trp Thr Asn Leu Asp Pro Glu Gln Leu Leu Glu Glu Leu
                215                 220                 225

Gly Pro Phe Ala Ser Leu Glu Gly Phe Arg Glu Leu Leu Asp Lys
                230                 235                 240
```

-continued

```
Ala Gln Val Gly Gln Ala Tyr Val Gly Arg Pro Cys Leu His Pro
            245                 250                 255

Asp Asp Leu His Cys Pro Pro Ser Ala Pro Asn His His Ser Arg
            260                 265                 270

Gln Ala Pro Asn Val Ala His Glu Leu Ser Gly Gly Cys His Gly
            275                 280                 285

Phe Ser His Lys Phe Met His Trp Gln Glu Leu Leu Leu Leu Gly
            290                 295                 300

Gly Met Ala Arg Asp Pro Gln Gly Glu Leu Leu Arg Ala Glu Ala
            305                 310                 315

Leu Gln Ser Thr Phe Leu Leu Met Ser Pro Arg Gln Leu Tyr Glu
            320                 325                 330

His Phe Arg Gly Asp Tyr Gln Thr His Asp Ile Gly Trp Ser Glu
            335                 340                 345

Glu Gln Ala Ser Thr Val Leu Gln Ala Trp Gln Arg Arg Phe Val
            350                 355                 360

Gln Leu Ala Gln Glu Ala Leu Pro Glu Asn Ala Ser Gln Gln Ile
            365                 370                 375

His Ala Phe Ser Ser Thr Thr Leu Asp Asp Ile Leu His Ala Phe
            380                 385                 390

Ser Glu Val Ser Ala Ala Arg Val Val Gly Gly Tyr Leu Leu Met
            395                 400                 405

Leu Ala Tyr Ala Cys Val Thr Met Leu Arg Trp Asp Cys Ala Gln
            410                 415                 420

Ser Gln Gly Ser Val Gly Leu Ala Gly Val Leu Leu Val Ala Leu
            425                 430                 435

Ala Val Ala Ser Gly Leu Gly Leu Cys Ala Leu Leu Gly Ile Thr
            440                 445                 450

Phe Asn Ala Ala Thr Thr Gln Val Leu Pro Phe Leu Ala Leu Gly
            455                 460                 465

Ile Gly Val Asp Asp Val Phe Leu Leu Ala His Ala Phe Thr Glu
            470                 475                 480

Ala Leu Pro Gly Thr Pro Leu Gln Glu Arg Met Gly Glu Cys Leu
            485                 490                 495

Gln Arg Thr Gly Thr Ser Val Val Leu Thr Ser Ile Asn Asn Met
            500                 505                 510

Ala Ala Phe Leu Met Ala Ala Leu Val Pro Ile Pro Ala Leu Arg
            515                 520                 525

Ala Phe Ser Leu Gln Ala Ala Ile Val Val Gly Cys Thr Phe Val
            530                 535                 540

Ala Val Met Leu Val Phe Pro Ala Ile Leu Ser Leu Asp Leu Arg
            545                 550                 555

Arg Arg His Cys Gln Arg Leu Asp Val Leu Cys Cys Phe Ser Ser
            560                 565                 570

Pro Cys Ser Ala Gln Val Ile Gln Ile Leu Pro Gln Glu Leu Gly
            575                 580                 585

Asp Gly Thr Val Pro Val Gly Ile Ala His Leu Thr Ala Thr Val
            590                 595                 600

Gln Ala Phe Thr His Cys Glu Ala Ser Ser Gln His Val Val Thr
            605                 610                 615

Ile Leu Pro Pro Gln Ala His Leu Val Pro Pro Ser Asp Pro
            620                 625                 630
```

-continued

```
Leu Gly Ser Glu Leu Phe Ser Pro Gly Gly Ser Thr Arg Asp Leu
            635                 640                 645

Leu Gly Gln Glu Glu Glu Thr Arg Gln Lys Ala Ala Cys Lys Ser
            650                 655                 660

Leu Pro Cys Ala Arg Trp Asn Leu Ala His Phe Ala Arg Tyr Gln
            665                 670                 675

Phe Ala Pro Leu Leu Gln Ser His Ala Lys Ala Ile Val Leu
            680                 685                 690

Val Leu Phe Gly Ala Leu Leu Gly Leu Ser Leu Tyr Gly Ala Thr
            695                 700                 705

Leu Val Gln Asp Gly Leu Ala Leu Thr Asp Val Val Pro Arg Gly
            710                 715                 720

Thr Lys Glu His Ala Phe Leu Ser Ala Gln Leu Arg Tyr Phe Ser
            725                 730                 735

Leu Tyr Glu Val Ala Leu Val Thr Gln Gly Gly Phe Asp Tyr Ala
            740                 745                 750

His Ser Gln Arg Ala Leu Phe Asp Leu His Gln Arg Phe Ser Ser
            755                 760                 765

Leu Lys Ala Val Leu Pro Pro Ala Thr Gln Ala Pro Arg Thr
            770                 775                 780

Trp Leu His Tyr Tyr Arg Asn Trp Leu Gln Gly Ile Gln Ala Ala
            785                 790                 795

Phe Asp Gln Asp Trp Ala Ser Gly Arg Ile Thr Arg His Ser Tyr
            800                 805                 810

Arg Asn Gly Ser Glu Asp Gly Ala Leu Ala Tyr Lys Leu Leu Ile
            815                 820                 825

Gln Thr Gly Asp Ala Gln Glu Pro Leu Asp Phe Ser Gln Leu Thr
            830                 835                 840

Thr Arg Lys Leu Val Asp Arg Glu Gly Leu Ile Pro Pro Glu Leu
            845                 850                 855

Phe Tyr Met Gly Leu Thr Val Trp Val Ser Ser Asp Pro Leu Gly
            860                 865                 870

Leu Ala Ala Ser Gln Ala Asn Phe Tyr Pro Pro Pro Glu Trp
            875                 880                 885

Leu His Asp Lys Tyr Asp Thr Thr Gly Glu Asn Leu Arg Ile Pro
            890                 895                 900

Pro Ala Gln Pro Leu Glu Phe Ala Gln Phe Pro Phe Leu Leu Arg
            905                 910                 915

Gly Leu Gln Lys Thr Ala Asp Phe Val Glu Ala Ile Glu Gly Ala
            920                 925                 930

Arg Ala Ala Cys Ala Glu Ala Gly Gln Ala Gly Val His Ala Tyr
            935                 940                 945

Pro Ser Gly Ser Pro Phe Leu Phe Trp Glu Gln Tyr Leu Gly Leu
            950                 955                 960

Arg Arg Cys Phe Leu Leu Ala Val Cys Ile Leu Leu Val Cys Thr
            965                 970                 975

Phe Leu Val Cys Ala Leu Leu Leu Asn Pro Trp Thr Ala Gly
            980                 985                 990

Leu Ile Val Leu Val Leu Ala Met Met Thr Val Glu Leu Phe Gly
            995                 1000                1005

Ile Met Gly Phe Leu Gly Ile Lys Leu Ser Ala Ile Pro Val Val
            1010                1015                1020

Ile Leu Val Ala Ser Val Gly Ile Gly Val Glu Phe Thr Val His
```

```
                    1025                1030                1035

Val Ala Leu Gly Phe Leu Thr Thr Gln Gly Ser Arg Asn Leu Arg
                    1040                1045                1050

Ala Ala His Ala Leu Glu His Thr Phe Ala Pro Val Thr Asp Gly
                    1055                1060                1065

Ala Ile Ser Thr Leu Leu Gly Leu Leu Met Leu Ala Gly Ser His
                    1070                1075                1080

Phe Asp Phe Ile Val Arg Tyr Phe Phe Ala Ala Leu Thr Val Leu
                    1085                1090                1095

Thr Leu Leu Gly Leu Leu His Gly Leu Val Leu Leu Pro Val Leu
                    1100                1105                1110

Leu Ser Ile Leu Gly Pro Pro Glu Val Ile Gln Met Tyr Lys
                    1115                1120                1125

Glu Ser Pro Glu Ile Leu Ser Pro Pro Ala Pro Gln Gly Gly Gly
                    1130                1135                1140

Leu Arg Trp Gly Ala Ser Ser Ser Leu Pro Gln Ser Phe Ala Arg
                    1145                1150                1155

Val Thr Thr Ser Met Thr Val Ala Ile His Pro Pro Pro Leu Pro
                    1160                1165                1170

Gly Ala Tyr Ile His Pro Ala Pro Asp Glu Pro Pro Trp Ser Pro
                    1175                1180                1185

Ala Ala Thr Ser Ser Gly Asn Leu Ser Ser Arg Gly Pro Gly Pro
                    1190                1195                1200

Ala Thr Gly
    1203

(2) INFORMATION FOR SEQ ID NO:3:

(i) SEQUENCE CHARACTERISTICS:
        (A) LENGTH: 228 base pairs
        (B) TYPE: Nucleic Acid
        (C) STRANDEDNESS: Single
        (D) TOPOLOGY: Linear (xi) SEQUENCE DESCRIPTION: SEQ ID NO:3:

GCTGGGGTGC ACGCCTACCN CAGCGGNTCC CCCTTCCTCT TCTGGGAACA           50

GTATCTGGGC CTGCGGCGCT GCTTCCTGCT GGCCGTCTGC ATCCTGCTGG          100

TGTGCACTTT CCTCGTCTGT GCTCTGCTGC TCCTNAACCC CTGGACGGCT          150

GGCCTNATAG TGCTGGTCCT GGCGATGATG ACAGTGGAAC TCTTTGGTAT          200

CATGGGTTTN CTGGGCATCA AGCTGAGT                                  228

(2) INFORMATION FOR SEQ ID NO:4:

(i) SEQUENCE CHARACTERISTICS:
        (A) LENGTH: 76 amino acids
        (B) TYPE: Amino Acid
        (D) TOPOLOGY: Linear (xi) SEQUENCE DESCRIPTION: SEQ ID NO:4:

Leu Gly Leu Ser Ser Tyr Pro Asn Gly Tyr Pro Phe Leu Phe Trp
  1               5                  10                  15

Glu Gln Tyr Ile Gly Leu Arg His Trp Leu Leu Phe Ile Ser
                 20                  25                  30

Val Val Leu Ala Cys Thr Phe Leu Val Cys Ala Val Phe Leu Leu
                 35                  40                  45

Asn Pro Trp Thr Ala Gly Ile Ile Val Met Val Leu Ala Leu Met
```

```
                   50                  55                  60
Thr Val Glu Leu Phe Gly Met Met Gly Leu Ile Gly Ile Lys Leu
                   65                  70                  75

Ser
 76

(2) INFORMATION FOR SEQ ID NO:5:

(i) SEQUENCE CHARACTERISTICS:
        (A) LENGTH: 125 base pairs
        (B) TYPE: Nucleic Acid
        (C) STRANDEDNESS: Single
        (D) TOPOLOGY: Linear (xi) SEQUENCE DESCRIPTION: SEQ ID NO:5:

GCTGGGGTGC ACGCCTACCC CAGCGGCTCC CCCTTCCTCT TCTGGGAACA              50

GTATCTGGGC CTGCGGCGCT GCTTCCTGCT GGCCGTCTGC ATCCTGCTGG             100

TGTGCACTTT CCTCNTCTGT GCTCT                                         125

(2) INFORMATION FOR SEQ ID NO:6:

(i) SEQUENCE CHARACTERISTICS:
        (A) LENGTH: 50 base pairs
        (B) TYPE: Nucleic Acid
        (C) STRANDEDNESS: Single
        (D) TOPOLOGY: Linear (xi) SEQUENCE DESCRIPTION: SEQ ID NO:6:

CCGGGCGGCA TGNNGCGAAG CGGACCACGC TGGGGGGTGG CTCAGGGGAG              50

(2) INFORMATION FOR SEQ ID NO:7:

(i) SEQUENCE CHARACTERISTICS:
        (A) LENGTH: 1182 amino acids
        (B) TYPE: Amino Acid
        (D) TOPOLOGY: Linear (xi) SEQUENCE DESCRIPTION: SEQ ID NO:7:

Met Val Arg Pro Leu Ser Leu Gly Glu Leu Pro Pro Ser Tyr Thr
 1                   5                  10                  15

Pro Pro Ala Arg Ser Ser Ala Pro His Ile Leu Ala Gly Ser Leu
                    20                  25                  30

Gln Ala Pro Leu Trp Leu Arg Ala Tyr Phe Gln Gly Leu Leu Phe
                    35                  40                  45

Ser Leu Gly Cys Arg Ile Gln Lys His Cys Gly Lys Val Leu Phe
                    50                  55                  60

Leu Gly Leu Val Ala Phe Gly Ala Leu Ala Leu Gly Leu Arg Val
                    65                  70                  75

Ala Val Ile Glu Thr Asp Leu Glu Gln Leu Trp Val Glu Val Gly
                    80                  85                  90

Ser Arg Val Ser Gln Glu Leu His Tyr Thr Lys Glu Lys Leu Gly
                    95                 100                 105

Glu Glu Ala Ala Tyr Thr Ser Gln Met Leu Ile Gln Thr Ala His
                   110                 115                 120

Gln Glu Gly Gly Asn Val Leu Thr Pro Glu Ala Leu Asp Leu His
                   125                 130                 135

Leu Gln Ala Ala Leu Thr Ala Ser Lys Val Gln Val Ser Leu Tyr
                   140                 145                 150

Gly Lys Ser Trp Asp Leu Asn Lys Ile Cys Tyr Lys Ser Gly Val
```

```
                        155                 160                 165
Pro Leu Ile Glu Asn Gly Met Ile Glu Arg Met Ile Glu Lys Leu
                170                 175                 180
Phe Pro Cys Val Ile Leu Thr Pro Leu Asp Cys Phe Trp Glu Gly
                185                 190                 195
Ala Lys Leu Gln Gly Gly Ser Ala Tyr Leu Pro Gly Arg Pro Asp
                200                 205                 210
Ile Gln Trp Thr Asn Leu Asp Pro Gln Gln Leu Leu Glu Glu Leu
                215                 220                 225
Gly Pro Phe Ala Ser Leu Glu Gly Phe Arg Glu Leu Leu Asp Lys
                230                 235                 240
Ala Gln Val Gly Gln Ala Tyr Val Gly Arg Pro Cys Leu Asp Pro
                245                 250                 255
Asp Asp Pro His Cys Pro Pro Ser Ala Pro Asn Arg His Ser Arg
                260                 265                 270
Gln Ala Pro Asn Val Ala Gln Glu Leu Ser Gly Gly Cys His Gly
                275                 280                 285
Phe Ser His Lys Phe Met His Trp Gln Glu Glu Leu Leu Leu Gly
                290                 295                 300
Gly Thr Ala Arg Asp Leu Gln Gly Gln Leu Leu Arg Ala Glu Ala
                305                 310                 315
Leu Gln Ser Thr Phe Leu Leu Met Ser Pro Arg Gln Leu Tyr Glu
                320                 325                 330
His Phe Arg Gly Asp Tyr Gln Thr His Asp Ile Gly Trp Ser Glu
                335                 340                 345
Glu Gln Ala Ser Met Val Leu Gln Ala Trp Gln Arg Arg Phe Val
                350                 355                 360
Gln Leu Ala Gln Glu Ala Leu Pro Ala Asn Ala Ser Gln Gln Ile
                365                 370                 375
His Ala Phe Ser Ser Thr Thr Leu Asp Asp Ile Leu Arg Ala Phe
                380                 385                 390
Ser Glu Val Ser Thr Thr Arg Val Val Gly Gly Tyr Leu Leu Met
                395                 400                 405
Leu Ala Tyr Ala Cys Val Thr Met Leu Arg Trp Asp Cys Ala Gln
                410                 415                 420
Ser Gln Gly Ala Val Gly Leu Ala Gly Val Leu Leu Val Ala Leu
                425                 430                 435
Ala Val Ala Ser Gly Leu Gly Leu Cys Ala Leu Leu Gly Ile Thr
                440                 445                 450
Phe Asn Ala Ala Thr Thr Gln Val Leu Pro Phe Leu Ala Leu Gly
                455                 460                 465
Ile Gly Val Asp Asp Ile Phe Leu Leu Ala His Ala Phe Thr Lys
                470                 475                 480
Ala Pro Pro Asp Thr Pro Leu Pro Glu Arg Met Gly Glu Cys Leu
                485                 490                 495
Arg Ser Thr Gly Thr Ser Val Ala Leu Thr Ser Val Asn Asn Met
                500                 505                 510
Val Ala Phe Phe Met Ala Ala Leu Val Pro Ile Pro Ala Leu Arg
                515                 520                 525
Ala Phe Ser Leu Gln Ala Ala Ile Val Val Gly Cys Asn Phe Ala
                530                 535                 540
Ala Val Met Leu Val Phe Pro Ala Ile Leu Ser Leu Asp Leu Arg
                545                 550                 555
```

-continued

```
Arg Arg His Arg Gln Arg Leu Asp Val Leu Cys Cys Phe Ser Ser
            560                 565                 570

Pro Cys Ser Ala Gln Val Ile Gln Met Leu Pro Gln Glu Leu Gly
            575                 580                 585

Asp Arg Ala Val Pro Val Gly Ile Ala His Leu Thr Ala Thr Val
            590                 595                 600

Gln Ala Phe Thr His Cys Glu Ala Ser Ser Gln His Val Val Thr
            605                 610                 615

Ile Leu Pro Pro Gln Ala His Leu Leu Ser Pro Ala Ser Asp Pro
            620                 625                 630

Leu Gly Ser Glu Leu Tyr Ser Pro Gly Gly Ser Thr Arg Asp Leu
            635                 640                 645

Leu Ser Gln Glu Glu Gly Thr Gly Pro Gln Ala Ala Cys Arg Pro
            650                 655                 660

Leu Leu Cys Ala His Trp Thr Leu Ala His Phe Ala Arg Tyr Gln
            665                 670                 675

Phe Ala Pro Leu Leu Gln Thr Arg Ala Lys Ala Leu Val Leu
            680                 685                 690

Leu Phe Phe Gly Ala Leu Leu Gly Leu Ser Leu Tyr Gly Ala Thr
            695                 700                 705

Leu Val Gln Asp Gly Leu Ala Leu Thr Asp Val Pro Arg Gly
            710                 715                 720

Thr Lys Glu His Ala Phe Leu Ser Ala Gln Leu Arg Tyr Phe Ser
            725                 730                 735

Leu Tyr Glu Val Ala Leu Val Thr Gln Gly Gly Phe Asp Tyr Ala
            740                 745                 750

His Ser Gln Arg Ala Leu Phe Asp Leu His Gln Arg Phe Ser Ser
            755                 760                 765

Leu Lys Ala Val Leu Pro Pro Ala Thr Gln Ala Pro Arg Thr
            770                 775                 780

Trp Leu His Tyr Tyr Arg Ser Trp Leu Gln Gly Ile Gln Ala Ala
            785                 790                 795

Phe Asp Gln Asp Trp Ala Ser Gly Arg Ile Thr Cys His Ser Tyr
            800                 805                 810

Arg Asn Gly Ser Glu Asp Gly Ala Leu Ala Tyr Lys Leu Leu Ile
            815                 820                 825

Gln Thr Gly Asn Ala Gln Glu Pro Leu Asp Phe Ser Gln Leu Thr
            830                 835                 840

Thr Arg Lys Leu Val Asp Lys Glu Gly Leu Ile Pro Pro Glu Leu
            845                 850                 855

Phe Tyr Met Gly Leu Thr Val Trp Val Ser Ser Asp Pro Leu Gly
            860                 865                 870

Leu Ala Ala Ser Gln Ala Asn Phe Tyr Pro Pro Pro Glu Trp
            875                 880                 885

Leu His Asp Lys Tyr Asp Thr Thr Gly Glu Asn Leu Arg Ile Pro
            890                 895                 900

Ala Ala Gln Pro Leu Glu Phe Ala Gln Phe Pro Phe Leu Leu His
            905                 910                 915

Gly Leu Gln Lys Thr Ala Asp Phe Val Glu Ala Ile Glu Gly Ala
            920                 925                 930

Arg Ala Ala Cys Thr Glu Ala Gly Gln Ala Gly Val His Ala Tyr
            935                 940                 945
```

```
Pro Ser Gly Ser Pro Phe Leu Phe Trp Glu Gln Tyr Leu Gly Leu
            950                 955                 960

Arg Arg Cys Phe Leu Leu Ala Val Cys Ile Leu Leu Val Cys Thr
            965                 970                 975

Phe Leu Val Cys Ala Leu Leu Leu Ser Pro Trp Thr Ala Gly
            980                 985                 990

Leu Ile Val Leu Val Leu Ala Met Met Thr Val Glu Leu Phe Gly
            995                 1000                1005

Ile Met Gly Phe Leu Gly Ile Lys Leu Ser Ala Ile Pro Val Val
            1010                1015                1020

Ile Leu Val Ala Ser Ile Gly Ile Gly Val Glu Phe Thr Val His
            1025                1030                1035

Val Ala Leu Gly Phe Leu Thr Ser His Gly Ser Arg Asn Leu Arg
            1040                1045                1050

Ala Ala Ser Ala Leu Glu Gln Thr Phe Ala Pro Val Thr Asp Gly
            1055                1060                1065

Ala Val Ser Thr Leu Leu Gly Leu Leu Met Leu Ala Gly Ser Asn
            1070                1075                1080

Phe Asp Phe Ile Ile Arg Tyr Phe Phe Val Val Leu Thr Val Leu
            1085                1090                1095

Thr Leu Leu Gly Leu Leu His Gly Leu Leu Leu Pro Val Leu
            1100                1105                1110

Leu Ser Ile Leu Gly Pro Pro Pro Gln Val Val Gln Val Tyr Lys
            1115                1120                1125

Glu Ser Pro Gln Thr Leu Asn Ser Ala Ala Pro Gln Arg Gly Gly
            1130                1135                1140

Leu Arg Trp Asp Arg Pro Pro Thr Leu Pro Gln Ser Phe Ala Arg
            1145                1150                1155

Val Thr Thr Ser Met Thr Val Ala Leu His Pro Pro Pro Leu Pro
            1160                1165                1170

Gly Ala Tyr Val His Pro Ala Ser Glu Glu Pro Thr
            1175                1180    1182

(2) INFORMATION FOR SEQ ID NO:8:

(i) SEQUENCE CHARACTERISTICS:
        (A) LENGTH: 4004 base pairs
        (B) TYPE: Nucleic Acid
        (C) STRANDEDNESS: Double
        (D) TOPOLOGY: Linear (xi) SEQUENCE DESCRIPTION: SEQ ID NO:8:

CCCACGCGTC CGGGAGAAGC TGGGGGAGGA GGCTGCATAC ACCTCTCAGA          50

TGCTGATACA GACCGCACGC CAGGAGGGAG AGAACATCCT CACACCCGAA         100

GCACTTGGCC TCCACCTCCA GGCAGCCCTC ACTGCCAGTA AAGTCCAAGT         150

ATCACTCTAT GGGAAGTCCT GGGATTTGAA CAAAATCTGC TACAAGTCAG         200

GAGTTCCCCT TATTGAAAAT GGAATGATTG AGCGGATGAT TGAGAAGCTG         250

TTTCCGTGCG TGATCCTCAC CCCCCTCGAC TGCTTCTGGG AGGGAGCCAA         300

ACTCCAAGGG GGCTCCGCCT ACCTGCCGCT CCCAATGTGG CTCACGAGCT         350

GAGTGGGGGC TGCCATGGCT TCTCCCACAA ATTCATGCAC TGGCAGGAGG         400

AATTGCTGCT GGGAGGCATG GCCAGAGACC CCCAAGGAGA GCTGCTGAGG         450

GCAGAGGCCC TGCAGAGCAC CTTCTTGCTG ATGAGTCCCC GCCAGCTGTA         500
```

-continued

| | |
|---|---|
| CGAGCATTTC CGGGGTGACT ATCAGACACA TGACATTGGC TGGAGTGAGG | 550 |
| AGCAGGCCAG CACAGTGCTA CAAGCCTGGC AGCGGCGCTT TGTGCAGGTC | 600 |
| GGTATGGACA AGGACAGGGG GGTGCCCTGA GGCCATTCCC TCCTCCTGCC | 650 |
| CCCTCCTATC CACCCTGTTT CTCCAGCTGG CCCAGGAGGC CCTGCCTGAG | 700 |
| AACGCTTCCC AGCAGATCCA TGCCTTCTCC TCCACCACCC TGGATGACAT | 750 |
| CCTGCATGCG TTCTCTGAAG TCAGTGCTGC CCGTGTGGTG GGAGGCTATC | 800 |
| TGCTCATGGT GGGTCTTGCA CCTGGCACCT TGCCCCCACC CCACCTCCAA | 850 |
| CCAGTGCCCA CCCTGGGGAG CCCCTGAGAC TGCCCTTTCC CCCCACAGCT | 900 |
| GGCCTATGCC TGTGTGACCA TGCTGCGGTG GGACTGCGCC CAGTCCCAGG | 950 |
| GTTCCGTGGG CCTTGCCGGG GTACTGCTGG TGGCCCTGGC GGTGGCCTCA | 1000 |
| GGCCTTGGGC TCTGTGCCCT GCTCGGCATC ACCTTCAATG CTGCCACTAC | 1050 |
| CCAGGTACGC CAGGACTGCA GGGCAGACTC AGTGCCAGTC ACCAGGCTTC | 1100 |
| ACGGGTCCTC AGCTGCCCGC TCCTCTGCCC CTCCAGGTGC TGCCCTTCTT | 1150 |
| GACTCTGGGA ATCGGCGTGG ATGACGTATT CCTGCTGGCG CATGCCTTCA | 1200 |
| CAGAGGCTCT GCCTGGCACC CCTCTCCAGG TGGGGCCTTG TCCCCCAGGG | 1250 |
| CTCATCTGAG GCAGCTCAGC TTACTGGTTA AGAGCCTCTT GGTTCAAGTG | 1300 |
| ACCTTGGGCT GCTAATGAAC CTCGGTGCCT CTTGTCCCCA TGTGTAAACA | 1350 |
| GGGGAAATAA TAGTGCTGTG TCCTAAGGGT TATTGTTTGG ATCAGTGAAG | 1400 |
| TAACTCAAGT TGAATGCTTA GAACAGCCCA TCATACGTAC ATGGTACCCA | 1450 |
| ATAAATGCTA GCCACTGTGT TATGACTGCC CCACCTCTGC ACCCCAAGTT | 1500 |
| CCTGAGCCTC CCCTTCACTC CACTTTGACA CGGCCCCTCC CTTGTGACCT | 1550 |
| GAGGGCAGGT CCCCACTCTG TCCTGGCAGG AGCGCATGGG CGAGTGTCTG | 1600 |
| CAGCGCACGG GCACCAGTGT TGTACTCACA TCCATCAACA ACATGGCCGC | 1650 |
| CTTCCTCATG GCTGCCCTCG TTCCCATCCC TGCGCTGCGA GCCTTCTCCC | 1700 |
| TACAGCCTGG ACCTACGGCG GCGCCACTGC CAGCGCCTTG ATGTGCTCTG | 1750 |
| CTGCTTCTCC AGGTACTGCC TGCGCCCCAG CCCCTTCCTC CCGTGACCCA | 1800 |
| CGCCAGCCTG TCCCCTCACC AGCATTTCAA GGCACAGACC TGTCATCCAC | 1850 |
| TCTCTACCTC TTCCAGTCCC TGCTCTGCTC AGGTGATTCA GATCCTGCCC | 1900 |
| CAGGAGCTGG GGACGGGAC AGTACCAGTG GCATTGCCC ACCTCACTGC | 1950 |
| CACAGTTCAA GCCTTTACCC ACTGTGAAGC CAGCAGCCAG CATGTGGTCA | 2000 |
| CCATCCTGCC TCCCCAAGCC CACCTGGTGC CCCCACCTTC TGACCCACTG | 2050 |
| GGCTCTGAGC TCTTCAGCCC TGGAGGGTCC ACACGGGACC TTCTAGGCCA | 2100 |
| GGAGGAGGAG ACAAGGCAGA AGGCAGCCTG CAAGTCCCTG CCCTGTGCCC | 2150 |
| GCTGGAATCT TGCCCATTTC GCCCGCTATC AGTTTGCCCC GTTGCTGCTC | 2200 |
| CAGTCACATG CCAAGGCCAT CGTGCTGGTG CTCTTTGGTG CTCTTCTGGG | 2250 |
| CCTGAGCCTC TACGGAGCCA CCTTGGTGCA AGACGGCCTG GCCCTGACGG | 2300 |
| ATGTGGTGCC TCGGGCACC AAGGAGCATG CCTTCCTGAG CGCCCAGCTC | 2350 |
| AGGTACTTCT CCCTGTACGA GGTGGCCCTG GTGACCCAGG GTGGCTTTGA | 2400 |
| CTACGCCCAC TCCCAACGCG CCCTCTTTGA TCTGCACCAG CGCTTCAGTT | 2450 |
| CCCTCAAGGC GGTGCTGCCC CCACCGGCCA CCCAGGCACC CCGCACCTGG | 2500 |

| | |
|---|---|
| CTGCACTATT ACCGCAACTG GCTACAGGGA ATCCAGGCTG CCTTTGACCA | 2550 |
| GGACTGGGCT TCTGGGCGCA TCACCCGCCA CTCGTACCGC AATGGCTCTG | 2600 |
| AGGATGGGGC CCTGGCCTAC AAGCTGCTCA TCCAGACTGG AGACGCCCAG | 2650 |
| GAGCCTCTGG ATTTCAGCCA GGTTGGGAGA GGGCTGGAGG GGTCCACTAG | 2700 |
| TACAGGGGCT GCAGGCCTCC TGGGCCCAGG CCTTCAGCCC TCTCTGCCTC | 2750 |
| TGCAGCTGAC CACAAGGAAG CTGGTGGACA GAGAGGGACT GATTCCACCC | 2800 |
| GAGCTCTTCT ACATGGGGCT GACCGTGTGG GTGAGCAGTG ACCCCCTGGG | 2850 |
| TCTGGCAGCC TCACAGGCCA ACTTCTACCC CCCACCTCCT GAATGGCTGC | 2900 |
| ACGACAAATA CGACACCACG GGGGAGAACC TTCGCAGTGA GTCTTGGGGG | 2950 |
| GAGCTCGGCA AGAGCCTCAG CCTCGCCCAC ACAAGCCCTG AGCCTGAGGC | 3000 |
| CCTGCCCACT CTGCCCCGTG CTCACCGCCC TGTCCCTCTC CCTCTTCTCC | 3050 |
| CTTCCCCTCC CCTCCACAGT CCCGCCAGCT CAGCCCTTGG AGTTTGCCCA | 3100 |
| GTTCCCCTTC CTGCTGCGTG GCCTCCAGAA GACTGCAGAC TTTGTGGAGG | 3150 |
| CCATCGAGGG GGCCCGGGCA GCATGCGCAG AGGCCGGCCA GGCTGGGGTG | 3200 |
| CACGCCTACC CCAGCGGCTC CCCCTTCCTC TTCTGGGAAC AGTATCTGGG | 3250 |
| CCTGCGGCGC TGCTTCCTGC TGGCCGTCTG CATCCTGCTG GTGTGCACTT | 3300 |
| TCCTCGTCTG TGCTCTGCTG CTCCTCAACC CCTGGACGGC TGGCCTCATA | 3350 |
| GTGAGTGCTT GCAGGAGTGG GGACAGAGAC ACCCCACCCT TCCCTGCCCA | 3400 |
| GCCTGTCATC CCTCCTGCCA GGAGCCCTCT GTGAGCCCTG TCTCCCTCAG | 3450 |
| GTGCTGGTCC TGGCGATGAT GACAGTGGAA CTCTTTGGTA TCATGGGTTT | 3500 |
| CCTGGGCATC AAGCTGAGTG CCATCCCCGT GGTGATCCTT GTGGCCTCTG | 3550 |
| TAGGCATTGG CGTTGAGTTC ACAGTCCACG TGGCTCTGGT GAGCACGGGC | 3600 |
| ACCCCGGGGA GGGACCAATC AGCTGATTCA GTATTCAACA CATATTGTTC | 3650 |
| AAGCCCCTAC TATGTGCTAG GTACTATTTA AGAATTTGGG CTGGGTGGAC | 3700 |
| GTGGTGGCTC ATTCCTGTAA TCCCAGCACT TTGGGAGGCC GAGGCGGGTG | 3750 |
| GATCACCTGA GGTCGGGAGT TCGAAACCAG CCTGGCCAAC ATGGTGAAAC | 3800 |
| CCTGTCTTTA CTAAAAATAC AAAAAATTAG CCAGGCGTGG TGGCACATGC | 3850 |
| CAGTAGTCCC AGCTACTTTG GAGGCTGAGG CAGAATTGCT TGAACCTGGG | 3900 |
| AGGCGAAGGT TGCAGTGAGC TGAGATCGTG CCATTGCACT CCAGCCTGGG | 3950 |
| CAACAAGAGT GCAACTCTCC GTCTCAAAAA AAAAAAAAA AAGGGCGGCC | 4000 |
| GCGA | 4004 |

(2) INFORMATION FOR SEQ ID NO:9:

(i) SEQUENCE CHARACTERISTICS:
  (A) LENGTH: 2082 base pairs
  (B) TYPE: Nucleic Acid
  (C) STRANDEDNESS: Double
  (D) TOPOLOGY: Linear (xi) SEQUENCE DESCRIPTION: SEQ ID NO:9:

| | |
|---|---|
| TTCCGGCATG ACTCGATCGC CGCCCCTCAG AGAGCTGCCC CCGAGTTACA | 50 |
| CACCCCCAGC TCGAACCGCA GCACCCCAGA TCCTAGCTGG GAGCCTGAAG | 100 |
| GCTCCACTCT GGCTTCGTGC TTACTTCCAG GGCCTGCTCT TCTCTCTGGG | 150 |

```
ATGCGGGATC CAGAGACATT GTGGCAAAGT GCTCTTTCTG GGACTGTTGG          200

CCTTTGGGGC CCTGGCATTA GGTCTCCGCA TGGCCATTAT TGAGACAAAC          250

TTGGAACAGC TCTGGGTAGA AGTGGGCAGC CGGGTGAGCC AGGAGCTGCA          300

TTACACCAAG GAGAAGCTGG GGGAGGAGGC TGCATACACC TCTCAGATGC          350

TGATACAGAC CGCACGCCAG GAGGGAGAGA ACATCCTCAC ACCCGAAGCA          400

CTTGGCCTCC ACCTCCAGGC AGCCCTCACT GCCAGTAAAG TCCAAGTATC          450

ACTCTATGGG AAGTCCTGGG ATTTGAACAA AATCTGCTAC AAGTCAGGAG          500

TTCCCCTTAT TGAAAATGGA ATGATTGAGT GGATGATTGA GAAGCTGTTT          550

CCGTGCGTGA TCCTCACCCC CCTCGACTGC TTCTGGGAGG GAGCCAAACT          600

CCAAGGGGGC TCCGCCTACC TGCCCGGCCG CCCGGATATC CAGTGGACCA          650

ACCTGGATCC AGAGCAGCTG CTGGAGGAGC TGGGTCCCTT TGCCTCCCTT          700

GAGGGCTTCC GGGAGCTGCT AGACAAGGCA CAGGTGGGCC AGGCCTACGT          750

GGGGCGGCCC TGTCTGCACC CTGATGACCT CCACTGCCCA CCTAGTGCCC          800

CCAACCATCA CAGCAGGCAG GCTCCCAATG TGGCTCACGA GCTGAGTGGG          850

GGCTGCCATG GCTTCTCCCA CAAATTCATG CACTGGCAGG AGGAATTGCT          900

GCTGGGAGGC ATGGCCAGAG ACCCCAAGG AGAGCTGCTG AGGGCAGAGG           950

CCCTGCAGAG CACCTTCTTG CTGATGAGTC CCGCCAGCT GTACGAGCAT          1000

TTCCGGGGTG ACTATCAGAC ACATGACATT GGCTGGAGTG AGGAGCAGGC          1050

CAGCACAGTG CTACAAGCCT GGCAGCGGCG CTTTGTGCAG CTGGCCCAGG          1100

AGGCCCTGCC TGAGAACGCT TCCCAGCAGA TCCATGCCTT CTCCTCCACC          1150

ACCCTGGATA ACATCCTGCA TGCGTTCTCT GAAGTCAGTG CTGCCCGTGT          1200

GGTGGGAGGC TATCTGCTCA TGCTGGCCTA TGCCTGTGTG ACCATGCTGC          1250

GGTGGGACTG CGCCCAGTCC CAGGGTTCCG TGGGCCTTGC CGGGGTACTG          1300

CTGGTGGCCC TGGCGGTGGC CTCAGGCCTT GGGCTCTGTG CCCTGCTCGG          1350

CATCACCTTC AATGCTGCCA CTACCCAGGT GCTGCCCTTC TTGGCTCTGG          1400

GAATCGGCGT GGATGACGTA TTCCTGCTGG CGCATGCCTT CACAGAGGCT          1450

CTGCCTGGCA CCCCTCTCCA GGAGCGCATG GGCGAGTGTC TGCAGCGCAC          1500

GGGCACCAGT GTCGTACTCA CATCCATCAA CAACATGGCC GCCTTCCTCA          1550

TGGCTGCCCT CGTTCCCATC CCTGCGCTGC GAGCCTTCTC CTTACAGCCA          1600

TCCTCAGCCT GGACCTACGG CGGCGCCACT GCCAGCGCCT TGATGTGCTC          1650

TGCTGCTTCT CCAGTCCCTG CTCTGCTCAG GTGATTCAGA TCCTGCCCCA          1700

GGAGCTGGGG GACGGGACAG TACCAGTGGG CATTGCCCAC CTCACTGCCA          1750

CAGTTCAAGC CTTTACCCAC TGTGAAGCCA GCAGCCAGCA TGTGGTCACC          1800

ATCCTGCCTC CCCAAGCCCA CCTGGTGCCC CCACCTTCTG ACCCACTGGG          1850

CTCTGAGCTC TTCAGCCCTG GAGGGTCCAC ACGGGACCTT CTAGGCCAGG          1900

AGGAGGAGAC AAGGCAGAAG GCAGCCTGCA AGTCCCTGCC CTGTGCCCGC          1950

TGGAATCTTG CCCATTTCGC CCCGGAATTC CTGCAGCCCG GGGATCCAC           2000

TAGTTCTAGA GCGGCCGCCA CCGCGGTGGA GCTCCAGCTT TGTTCCCTT           2050

TAGTGAGGGT TAATTGCGCG CTTGGGTATC TT                            2082
```

(2) INFORMATION FOR SEQ ID NO:10:

(i) SEQUENCE CHARACTERISTICS:
        (A) LENGTH: 1315 amino acids
        (B) TYPE: Amino Acid
        (D) TOPOLOGY: Linear (xi) SEQUENCE DESCRIPTION: SEQ ID NO:10:

```
Met Glu Lys Tyr His Val Leu Glu Met Ile Gly Glu Gly Ser Phe
 1               5                  10                  15

Gly Arg Val Tyr Lys Gly Arg Arg Lys Tyr Ser Ala Gln Val Val
                20                  25                  30

Ala Leu Lys Phe Ile Pro Lys Leu Gly Arg Ser Glu Lys Glu Leu
                35                  40                  45

Arg Asn Leu Gln Arg Glu Ile Glu Ile Met Arg Gly Leu Arg His
                50                  55                  60

Pro Asn Ile Val His Met Leu Asp Ser Phe Glu Thr Asp Lys Glu
                65                  70                  75

Val Val Val Val Thr Asp Tyr Ala Glu Gly Glu Leu Phe Gln Ile
                80                  85                  90

Leu Glu Asp Asp Gly Lys Leu Pro Glu Asp Gln Val Gln Ala Ile
                95                 100                 105

Ala Ala Gln Leu Val Ser Ala Leu Tyr Tyr Leu His Ser His Arg
               110                 115                 120

Ile Leu His Arg Asp Met Lys Pro Gln Asn Ile Leu Leu Ala Lys
               125                 130                 135

Gly Gly Gly Ile Lys Leu Cys Asp Phe Gly Phe Ala Arg Ala Met
               140                 145                 150

Ser Thr Asn Thr Met Val Leu Thr Ser Ile Lys Gly Thr Pro Leu
               155                 160                 165

Tyr Met Ser Pro Glu Leu Val Glu Glu Arg Pro Tyr Asp His Thr
               170                 175                 180

Ala Asp Leu Trp Ser Val Gly Cys Ile Leu Tyr Glu Leu Ala Val
               185                 190                 195

Gly Thr Pro Pro Phe Tyr Ala Thr Ser Ile Phe Gln Leu Val Ser
               200                 205                 210

Leu Ile Leu Lys Asp Pro Val Arg Trp Pro Ser Thr Ile Ser Pro
               215                 220                 225

Cys Phe Lys Asn Phe Leu Gln Gly Leu Leu Thr Lys Asp Pro Arg
               230                 235                 240

Gln Arg Leu Ser Trp Pro Asp Leu Leu Tyr His Pro Phe Ile Ala
               245                 250                 255

Gly His Val Thr Ile Ile Thr Glu Pro Ala Gly Pro Asp Leu Gly
               260                 265                 270

Thr Pro Phe Thr Ser Arg Leu Pro Pro Glu Leu Gln Val Leu Lys
               275                 280                 285

Asp Glu Gln Ala His Arg Leu Ala Pro Lys Gly Asn Gln Ser Arg
               290                 295                 300

Ile Leu Thr Gln Ala Tyr Lys Arg Met Ala Glu Glu Ala Met Gln
               305                 310                 315

Lys Lys His Gln Asn Thr Gly Pro Ala Leu Glu Gln Glu Asp Lys
               320                 325                 330

Thr Ser Lys Val Ala Pro Gly Thr Ala Pro Leu Pro Arg Leu Gly
               335                 340                 345
```

-continued

```
Ala Thr Pro Gln Glu Ser Ser Leu Leu Ala Gly Ile Leu Ala Ser
            350                 355                 360

Glu Leu Lys Ser Ser Trp Ala Lys Ser Gly Thr Gly Glu Val Pro
            365                 370                 375

Ser Ala Pro Arg Glu Asn Arg Thr Thr Pro Asp Cys Glu Arg Ala
            380                 385                 390

Phe Pro Glu Glu Arg Pro Glu Val Leu Gly Gln Arg Ser Thr Asp
            395                 400                 405

Val Val Asp Leu Glu Asn Glu Glu Pro Asp Ser Asp Asn Glu Trp
            410                 415                 420

Gln His Leu Leu Glu Thr Thr Glu Pro Val Pro Ile Gln Leu Lys
            425                 430                 435

Ala Pro Leu Thr Leu Leu Cys Asn Pro Asp Phe Cys Gln Arg Ile
            440                 445                 450

Gln Ser Gln Leu His Glu Ala Gly Gly Gln Ile Leu Lys Gly Ile
            455                 460                 465

Leu Glu Gly Ala Ser His Ile Leu Pro Ala Phe Arg Val Leu Ser
            470                 475                 480

Ser Leu Leu Ser Ser Cys Ser Asp Ser Val Ala Leu Tyr Ser Phe
            485                 490                 495

Cys Arg Glu Ala Gly Leu Pro Gly Leu Leu Ser Leu Leu Arg
            500                 505                 510

His Ser Gln Glu Ser Asn Ser Leu Gln Gln Gln Ser Trp Tyr Gly
            515                 520                 525

Thr Phe Leu Gln Asp Leu Met Ala Val Ile Gln Ala Tyr Phe Ala
            530                 535                 540

Cys Thr Phe Asn Leu Glu Arg Ser Gln Thr Ser Asp Ser Leu Gln
            545                 550                 555

Val Phe Gln Glu Ala Ala Asn Leu Phe Leu Asp Leu Leu Gly Lys
            560                 565                 570

Leu Leu Ala Gln Pro Asp Asp Ser Glu Gln Thr Leu Arg Arg Asp
            575                 580                 585

Ser Leu Met Cys Phe Thr Val Leu Cys Glu Ala Met Asp Gly Asn
            590                 595                 600

Ser Arg Ala Ile Ser Lys Ala Phe Tyr Ser Ser Leu Leu Thr Thr
            605                 610                 615

Gln Gln Val Val Leu Asp Gly Leu Leu His Gly Leu Thr Val Pro
            620                 625                 630

Gln Leu Pro Val His Thr Pro Gln Gly Ala Pro Gln Val Ser Gln
            635                 640                 645

Pro Leu Arg Glu Gln Ser Glu Asp Ile Pro Gly Ala Ile Ser Ser
            650                 655                 660

Ala Leu Ala Ala Ile Cys Thr Ala Pro Val Gly Leu Pro Asp Cys
            665                 670                 675

Trp Asp Ala Lys Glu Gln Val Cys Trp His Leu Ala Asn Gln Leu
            680                 685                 690

Thr Glu Asp Ser Ser Gln Leu Arg Pro Ser Leu Ile Ser Gly Leu
            695                 700                 705

Gln His Pro Ile Leu Cys Leu His Leu Leu Lys Val Leu Tyr Ser
            710                 715                 720

Cys Cys Leu Val Ser Glu Gly Leu Cys Arg Leu Leu Gly Gln Glu
            725                 730                 735

Pro Leu Ala Leu Glu Ser Leu Phe Met Leu Ile Gln Gly Lys Val
```

-continued

```
                    740                 745                 750
Lys Val Val Asp Trp Glu Glu Ser Thr Glu Val Thr Leu Tyr Phe
                755                 760                 765
Leu Ser Leu Leu Val Phe Arg Leu Gln Asn Leu Pro Cys Gly Met
                770                 775                 780
Glu Lys Leu Gly Ser Asp Val Ala Thr Leu Phe Thr His Ser His
                785                 790                 795
Val Val Ser Leu Val Ser Ala Ala Cys Leu Leu Gly Gln Leu
                800                 805                 810
Gly Gln Gln Gly Val Thr Phe Asp Leu Gln Pro Met Glu Trp Met
                815                 820                 825
Ala Ala Ala Thr His Ala Leu Ser Ala Pro Ala Glu Val Arg Leu
                830                 835                 840
Thr Pro Pro Gly Ser Cys Gly Phe Tyr Asp Gly Leu Leu Ile Leu
                845                 850                 855
Leu Leu Gln Leu Leu Thr Glu Gln Gly Lys Ala Ser Leu Ile Arg
                860                 865                 870
Asp Met Ser Ser Ser Glu Met Trp Thr Val Leu Trp His Arg Phe
                875                 880                 885
Ser Met Val Leu Arg Leu Pro Glu Glu Ala Ser Ala Gln Glu Gly
                890                 895                 900
Glu Leu Ser Leu Ser Ser Pro Pro Ser Glu Pro Asp Trp Thr
                905                 910                 915
Leu Ile Ser Pro Gln Gly Met Ala Ala Leu Leu Ser Leu Ala Met
                920                 925                 930
Ala Thr Phe Thr Gln Glu Pro Gln Leu Cys Leu Ser Cys Leu Ser
                935                 940                 945
Gln His Gly Ser Ile Leu Met Ser Ile Leu Lys His Leu Leu Cys
                950                 955                 960
Pro Ser Phe Leu Asn Gln Leu Arg Gln Ala Pro His Gly Ser Glu
                965                 970                 975
Phe Leu Pro Val Val Val Leu Ser Val Cys Gln Leu Leu Cys Phe
                980                 985                 990
Pro Phe Ala Leu Asp Met Asp Ala Asp Leu Leu Ile Val Val Leu
                995                 1000                1005
Ala Asp Leu Arg Asp Ser Glu Val Ala Ala His Leu Leu Gln Val
                1010                1015                1020
Cys Cys Tyr His Leu Pro Leu Met Gln Val Glu Leu Pro Ile Ser
                1025                1030                1035
Leu Leu Thr Arg Leu Ala Leu Met Asp Pro Thr Ser Leu Asn Gln
                1040                1045                1050
Phe Val Asn Thr Val Ser Ala Ser Pro Arg Thr Ile Val Ser Phe
                1055                1060                1065
Leu Ser Val Ala Leu Leu Ser Asp Gln Pro Leu Leu Thr Ser Asp
                1070                1075                1080
Leu Leu Ser Leu Leu Ala His Thr Ala Arg Val Leu Ser Pro Ser
                1085                1090                1095
His Leu Ser Phe Ile Gln Glu Leu Leu Ala Gly Ser Asp Glu Ser
                1100                1105                1110
Tyr Arg Pro Leu Arg Ser Leu Leu Gly His Pro Glu Asn Ser Val
                1115                1120                1125
Arg Ala His Thr Tyr Arg Leu Leu Gly His Leu Leu Gln His Ser
                1130                1135                1140
```

Met Ala Leu Arg Gly Ala Leu Gln Ser Gln Ser Gly Leu Leu Ser
            1145                1150                1155

Leu Leu Leu Leu Gly Leu Gly Asp Lys Asp Pro Val Val Arg Cys
            1160                1165                1170

Ser Ala Ser Phe Ala Val Gly Asn Ala Ala Tyr Gln Ala Gly Pro
            1175                1180                1185

Leu Gly Pro Ala Leu Ala Ala Ala Val Pro Ser Met Thr Gln Leu
            1190                1195                1200

Leu Gly Asp Pro Gln Ala Gly Ile Arg Arg Asn Val Ala Ser Ala
            1205                1210                1215

Leu Gly Asn Leu Gly Pro Glu Gly Leu Gly Glu Glu Leu Leu Gln
            1220                1225                1230

Cys Glu Val Pro Gln Arg Leu Leu Glu Met Ala Cys Gly Asp Pro
            1235                1240                1245

Gln Pro Asn Val Lys Glu Ala Ala Leu Ile Ala Leu Arg Ser Leu
            1250                1255                1260

Gln Gln Glu Pro Gly Ile His Gln Val Leu Val Ser Leu Gly Ala
            1265                1270                1275

Ser Glu Lys Leu Ser Leu Leu Ser Leu Gly Asn Gln Ser Leu Pro
            1280                1285                1290

His Ser Ser Pro Arg Pro Ala Ser Ala Lys His Cys Arg Lys Leu
            1295                1300                1305

Ile His Leu Leu Arg Pro Ala His Ser Met
            1310                1315

(2) INFORMATION FOR SEQ ID NO:11:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO:11:

CTATGAAATT AACCCTCACT AAAGGGAGCT CCCGTGAGTC CCTATGTG                48

(2) INFORMATION FOR SEQ ID NO:12:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO:12:

GGATTCTAAT ACGACTCACT ATAGGGCCCC TAAACTCCGC TGCTCCAC                48

(2) INFORMATION FOR SEQ ID NO:13:

(i) SEQUENCE CHARACTERISTICS:
        (A) LENGTH: 396 amino acids
        (B) TYPE: Amino Acid
        (D) TOPOLOGY: Linear (xi) SEQUENCE DESCRIPTION: SEQ ID NO:13:

Met Ala Leu Pro Ala Ser Leu Leu Pro Leu Cys Cys Leu Ala Leu
 1               5                  10                  15

Leu Ala Leu Ser Ala Gln Ser Cys Gly Pro Gly Arg Gly Pro Val
            20                  25                  30

```
Gly Arg Arg Arg Tyr Val Arg Lys Gln Leu Val Pro Leu Leu Tyr
                 35                  40                  45

Lys Gln Phe Val Pro Ser Met Pro Glu Arg Thr Leu Gly Ala Ser
                 50                  55                  60

Gly Pro Ala Glu Gly Arg Val Thr Arg Gly Ser Glu Arg Phe Arg
                 65                  70                  75

Asp Leu Val Pro Asn Tyr Asn Pro Asp Ile Ile Phe Lys Asp Glu
                 80                  85                  90

Glu Asn Ser Gly Ala Asp Arg Leu Met Thr Glu Arg Cys Lys Glu
                 95                 100                 105

Arg Val Asn Ala Leu Ala Ile Ala Val Met Asn Met Trp Pro Gly
                110                 115                 120

Val Arg Leu Arg Val Thr Glu Gly Trp Asp Glu Asp Gly His His
                125                 130                 135

Ala Gln Asp Ser Leu His Tyr Glu Gly Arg Ala Leu Asp Ile Thr
                140                 145                 150

Thr Ser Asp Arg Asp Arg Asn Lys Tyr Gly Leu Leu Ala Arg Leu
                155                 160                 165

Ala Val Glu Ala Gly Phe Asp Trp Val Tyr Tyr Glu Ser Arg Asn
                170                 175                 180

His Ile His Val Ser Val Lys Ala Asp Asn Ser Leu Ala Val Arg
                185                 190                 195

Ala Gly Gly Cys Phe Pro Gly Asn Ala Thr Val Arg Leu Arg Ser
                200                 205                 210

Gly Glu Arg Lys Gly Leu Arg Glu Leu His Arg Gly Asp Trp Val
                215                 220                 225

Leu Ala Ala Asp Ala Ala Gly Arg Val Val Pro Thr Pro Val Leu
                230                 235                 240

Leu Phe Leu Asp Arg Asp Leu Gln Arg Arg Ala Ser Phe Val Ala
                245                 250                 255

Val Glu Thr Glu Arg Pro Pro Arg Lys Leu Leu Leu Thr Pro Trp
                260                 265                 270

His Leu Val Phe Ala Ala Arg Gly Pro Ala Pro Ala Pro Gly Asp
                275                 280                 285

Phe Ala Pro Val Phe Ala Arg Arg Leu Arg Ala Gly Asp Ser Val
                290                 295                 300

Leu Ala Pro Gly Gly Asp Ala Leu Gln Pro Ala Arg Val Ala Arg
                305                 310                 315

Val Ala Arg Glu Glu Ala Val Gly Val Phe Ala Pro Leu Thr Ala
                320                 325                 330

His Gly Thr Leu Leu Val Asn Asp Val Leu Ala Ser Cys Tyr Ala
                335                 340                 345

Val Leu Glu Ser His Gln Trp Ala His Arg Ala Phe Ala Pro Leu
                350                 355                 360

Arg Leu Leu His Ala Leu Gly Ala Leu Leu Pro Gly Gly Ala Val
                365                 370                 375

Gln Pro Thr Gly Met His Trp Tyr Ser Arg Leu Leu Tyr Arg Leu
                380                 385                 390

Ala Glu Glu Leu Met Gly
                395 396
```

(2) INFORMATION FOR SEQ ID NO:14:

(i) SEQUENCE CHARACTERISTICS:

(A) LENGTH: 437 amino acids
(B) TYPE: Amino Acid
(D) TOPOLOGY: Linear (xi) SEQUENCE DESCRIPTION: SEQ ID NO:14:

```
Met Leu Leu Leu Leu Ala Arg Cys Phe Leu Val Ile Leu Ala Ser
 1               5                  10                  15

Ser Leu Leu Val Cys Pro Gly Leu Ala Cys Gly Pro Gly Arg Gly
                20                  25                  30

Phe Gly Lys Arg His Pro Lys Lys Leu Thr Pro Leu Ala Tyr
                35                  40                  45

Lys Gln Phe Ile Pro Asn Val Ala Glu Lys Thr Leu Gly Ala Ser
                50                  55                  60

Gly Arg Tyr Glu Gly Lys Ile Thr Arg Asn Ser Glu Arg Phe Lys
                65                  70                  75

Glu Leu Thr Pro Asn Tyr Asn Pro Asp Ile Ile Phe Lys Asp Glu
                80                  85                  90

Glu Asn Thr Gly Ala Asp Arg Leu Met Thr Gln Arg Cys Lys Asp
                95                 100                 105

Lys Leu Asn Ala Leu Ala Ile Ser Val Met Asn Gln Trp Pro Gly
               110                 115                 120

Val Arg Leu Arg Val Thr Glu Gly Trp Asp Glu Asp Gly His His
               125                 130                 135

Ser Glu Glu Ser Leu His Tyr Glu Gly Arg Ala Val Asp Ile Thr
               140                 145                 150

Thr Ser Asp Arg Asp Arg Ser Lys Tyr Gly Met Leu Ala Arg Leu
               155                 160                 165

Ala Val Glu Ala Gly Phe Asp Trp Val Tyr Tyr Glu Ser Lys Ala
               170                 175                 180

His Ile His Cys Ser Val Lys Ala Glu Asn Ser Val Ala Ala Lys
               185                 190                 195

Ser Gly Gly Cys Phe Pro Gly Ser Ala Thr Val His Leu Glu Gln
               200                 205                 210

Gly Gly Thr Lys Leu Val Lys Asp Leu Arg Pro Gly Asp Arg Val
               215                 220                 225

Leu Ala Ala Asp Asp Gln Gly Arg Leu Leu Tyr Ser Asp Phe Leu
               230                 235                 240

Thr Phe Leu Asp Arg Asp Glu Gly Ala Lys Lys Val Phe Tyr Val
               245                 250                 255

Ile Glu Thr Leu Glu Pro Arg Glu Arg Leu Leu Leu Thr Ala Ala
               260                 265                 270

His Leu Leu Phe Val Ala Pro His Asn Asp Ser Gly Pro Thr Pro
               275                 280                 285

Gly Pro Ser Ala Leu Phe Ala Ser Arg Val Arg Pro Gly Gln Arg
               290                 295                 300

Val Tyr Val Val Ala Glu Arg Gly Gly Asp Arg Arg Leu Leu Pro
               305                 310                 315

Ala Ala Val His Ser Val Thr Leu Arg Glu Glu Ala Gly Ala
               320                 325                 330

Tyr Ala Pro Leu Thr Ala His Gly Thr Ile Leu Ile Asn Arg Val
               335                 340                 345

Leu Ala Ser Cys Tyr Ala Val Ile Glu Glu His Ser Trp Ala His
               350                 355                 360

Arg Ala Phe Ala Pro Phe Arg Leu Ala His Ala Leu Leu Ala Ala
```

```
                        365                 370                 375
Leu Ala Pro Ala Arg Thr Asp Gly Gly Gly Gly Ser Ile Pro
                380                 385                 390

Ala Ala Gln Ser Ala Thr Glu Ala Arg Gly Ala Glu Pro Thr Ala
                395                 400                 405

Gly Ile His Trp Tyr Ser Gln Leu Leu Tyr His Ile Gly Thr Trp
                410                 415                 420

Leu Leu Asp Ser Glu Thr Met His Pro Leu Gly Met Ala Val Lys
                425                 430                 435

Ala Ser
    437

(2) INFORMATION FOR SEQ ID NO:15:

(i) SEQUENCE CHARACTERISTICS:
        (A) LENGTH: 803 amino acids
        (B) TYPE: Amino Acid
        (D) TOPOLOGY: Linear (xi) SEQUENCE DESCRIPTION: SEQ ID NO:15:

Met Ala Ala Gly Arg Pro Val Arg Gly Pro Glu Leu Ala Pro Arg
  1               5                  10                  15

Arg Leu Leu Gln Leu Leu Leu Val Leu Leu Gly Gly Arg Gly
                 20                  25                  30

Arg Gly Ala Ala Leu Ser Gly Asn Val Thr Gly Pro Gly Pro Arg
                 35                  40                  45

Ser Ala Gly Gly Ser Ala Arg Arg Asn Ala Pro Val Thr Ser Pro
                 50                  55                  60

Pro Pro Pro Leu Leu Ser His Cys Gly Arg Ala Ala His Cys Glu
                 65                  70                  75

Pro Leu Arg Tyr Asn Val Cys Leu Gly Ser Ala Leu Pro Tyr Gly
                 80                  85                  90

Ala Thr Thr Thr Leu Leu Ala Gly Asp Ser Asp Ser Gln Glu Glu
                 95                 100                 105

Ala His Ser Lys Leu Val Leu Trp Ser Gly Leu Arg Asn Ala Pro
                110                 115                 120

Arg Cys Trp Ala Val Ile Gln Pro Leu Leu Cys Ala Val Tyr Met
                125                 130                 135

Pro Lys Cys Glu Asn Asp Arg Val Glu Leu Pro Ser Arg Thr Leu
                140                 145                 150

Cys Gln Ala Thr Arg Gly Pro Cys Ala Ile Val Glu Arg Glu Arg
                155                 160                 165

Gly Trp Pro Asp Phe Leu Arg Cys Thr Pro Asp His Phe Pro Glu
                170                 175                 180

Gly Cys Pro Asn Glu Val Gln Asn Ile Lys Phe Asn Ser Ser Gly
                185                 190                 195

Gln Cys Glu Ala Pro Leu Val Arg Thr Asp Asn Pro Lys Ser Trp
                200                 205                 210

Tyr Glu Asp Val Glu Gly Cys Gly Ile Gln Cys Gln Asn Pro Leu
                215                 220                 225

Phe Thr Glu Ala Glu His Gln Asp Met His Ser Tyr Ile Ala Ala
                230                 235                 240

Phe Gly Ala Val Thr Gly Leu Cys Thr Leu Phe Thr Leu Ala Thr
                245                 250                 255

Phe Val Ala Asp Trp Arg Asn Ser Asn Arg Tyr Pro Ala Val Ile
```

-continued

```
                260                 265                 270
Leu Phe Tyr Val Asn Ala Cys Phe Val Gly Ser Ile Gly Trp
                275                 280                 285
Leu Ala Gln Phe Met Asp Gly Ala Arg Arg Glu Ile Val Cys Arg
            290                 295                 300
Ala Asp Gly Thr Met Arg Phe Gly Glu Pro Thr Ser Ser Glu Thr
            305                 310                 315
Leu Ser Cys Val Ile Ile Phe Val Ile Tyr Tyr Ala Leu Met
                320                 325                 330
Ala Gly Val Val Trp Phe Val Val Leu Thr Tyr Ala Trp His Thr
            335                 340                 345
Ser Phe Lys Ala Leu Gly Thr Thr Tyr Gln Pro Leu Ser Gly Lys
            350                 355                 360
Thr Ser Tyr Phe His Leu Leu Thr Trp Ser Leu Pro Phe Val Leu
            365                 370                 375
Thr Val Ala Ile Leu Ala Val Ala Gln Val Asp Gly Asp Ser Val
            380                 385                 390
Ser Gly Ile Cys Phe Val Gly Tyr Lys Asn Tyr Arg Tyr Arg Ala
            395                 400                 405
Gly Phe Val Leu Ala Pro Ile Gly Leu Val Leu Ile Val Gly Gly
            410                 415                 420
Tyr Phe Leu Ile Arg Gly Val Met Thr Leu Phe Ser Ile Lys Ser
            425                 430                 435
Asn His Pro Gly Leu Leu Ser Glu Lys Ala Ala Ser Lys Ile Asn
            440                 445                 450
Glu Thr Met Leu Arg Leu Gly Ile Phe Gly Phe Leu Ala Phe Gly
            455                 460                 465
Phe Val Leu Ile Thr Phe Ser Cys His Phe Tyr Asp Phe Phe Asn
            470                 475                 480
Gln Ala Glu Trp Glu Arg Ser Phe Arg Asp Tyr Val Leu Cys Gln
            485                 490                 495
Ala Asn Val Thr Ile Gly Leu Pro Thr Lys Lys Pro Ile Pro Asp
            500                 505                 510
Cys Glu Ile Lys Asn Arg Pro Ser Leu Leu Val Glu Lys Ile Asn
            515                 520                 525
Leu Phe Ala Met Phe Gly Thr Gly Ile Ala Met Ser Thr Trp Val
            530                 535                 540
Trp Thr Lys Ala Thr Leu Leu Ile Trp Arg Arg Thr Trp Cys Arg
            545                 550                 555
Leu Thr Gly His Ser Asp Asp Glu Pro Lys Arg Ile Lys Lys Ser
            560                 565                 570
Lys Met Ile Ala Lys Ala Phe Ser Lys Arg Arg Glu Leu Leu Gln
            575                 580                 585
Asn Pro Gly Gln Glu Leu Ser Phe Ser Met His Thr Val Ser His
            590                 595                 600
Asp Gly Pro Val Ala Gly Leu Ala Phe Glu Leu Asn Glu Pro Ser
            605                 610                 615
Ala Asp Val Ser Ser Ala Trp Ala Gln His Val Thr Lys Met Val
            620                 625                 630
Ala Arg Arg Gly Ala Ile Leu Pro Gln Asp Val Ser Val Thr Pro
            635                 640                 645
Val Ala Thr Pro Val Pro Pro Glu Gln Ala Asn Leu Trp Leu
            650                 655                 660
```

```
Val Glu Ala Glu Ile Ser Pro Glu Leu Glu Lys Arg Leu Gly Arg
            665                 670                 675

Lys Lys Lys Arg Arg Lys Arg Lys Lys Glu Val Cys Pro Leu Gly
            680                 685                 690

Pro Ala Pro Glu Leu His His Ser Ala Pro Val Pro Ala Thr Ser
            695                 700                 705

Ala Val Pro Arg Leu Pro Gln Leu Pro Arg Gln Lys Cys Leu Val
            710                 715                 720

Ala Ala Asn Ala Trp Gly Thr Gly Glu Pro Cys Arg Gln Gly Ala
            725                 730                 735

Trp Thr Val Val Ser Asn Pro Phe Cys Pro Glu Pro Ser Pro His
            740                 745                 750

Gln Asp Pro Phe Leu Pro Gly Ala Ser Ala Pro Arg Val Trp Ala
            755                 760                 765

Gln Gly Arg Leu Gln Gly Leu Gly Ser Ile His Ser Arg Thr Asn
            770                 775                 780

Leu Met Glu Ala Glu Leu Leu Asp Ala Asp Ser Asp Phe Glu Gln
            785                 790                 795

Lys Leu Ile Ser Glu Glu Asp Leu
            800         803

(2) INFORMATION FOR SEQ ID NO:16:

(i) SEQUENCE CHARACTERISTICS:
        (A) LENGTH: 793 amino acids
        (B) TYPE: Amino Acid
        (D) TOPOLOGY: Linear (xi) SEQUENCE DESCRIPTION: SEQ ID NO:16:

Met Ala Ala Gly Arg Pro Val Arg Gly Pro Glu Leu Ala Pro Arg
  1             5                  10                  15

Arg Leu Leu Gln Leu Leu Leu Val Leu Leu Gly Gly Arg Gly
             20                  25                  30

Arg Gly Ala Ala Leu Ser Gly Asn Val Thr Gly Pro Gly Pro Arg
             35                  40                  45

Ser Ala Gly Gly Ser Ala Arg Arg Asn Ala Pro Val Thr Ser Pro
             50                  55                  60

Pro Pro Pro Leu Leu Ser His Cys Gly Arg Ala Ala His Cys Glu
             65                  70                  75

Pro Leu Arg Tyr Asn Val Cys Leu Gly Ser Ala Leu Pro Tyr Gly
             80                  85                  90

Ala Thr Thr Thr Leu Leu Ala Gly Asp Ser Asp Ser Gln Glu Glu
             95                 100                 105

Ala His Ser Lys Leu Val Leu Trp Ser Gly Leu Arg Asn Ala Pro
            110                 115                 120

Arg Cys Trp Ala Val Ile Gln Pro Leu Leu Cys Ala Val Tyr Met
            125                 130                 135

Pro Lys Cys Glu Asn Asp Arg Val Glu Leu Pro Ser Arg Thr Leu
            140                 145                 150

Cys Gln Ala Thr Arg Gly Pro Cys Ala Ile Val Glu Arg Glu Arg
            155                 160                 165

Gly Trp Pro Asp Phe Leu Arg Cys Thr Pro Asp His Phe Pro Glu
            170                 175                 180

Gly Cys Pro Asn Glu Val Gln Asn Ile Lys Phe Asn Ser Ser Gly
            185                 190                 195
```

-continued

```
Gln Cys Glu Ala Pro Leu Val Arg Thr Asp Asn Pro Lys Ser Trp
            200                 205                 210
Tyr Glu Asp Val Glu Gly Cys Gly Ile Gln Cys Gln Asn Pro Leu
            215                 220                 225
Phe Thr Glu Ala Glu His Gln Asp Met His Ser Tyr Ile Ala Ala
            230                 235                 240
Phe Gly Ala Val Thr Gly Leu Cys Thr Leu Phe Thr Leu Ala Thr
            245                 250                 255
Phe Val Ala Asp Trp Arg Asn Ser Asn Arg Tyr Pro Ala Val Ile
            260                 265                 270
Leu Phe Tyr Val Asn Ala Cys Phe Phe Val Gly Ser Ile Gly Trp
            275                 280                 285
Leu Ala Gln Phe Met Asp Gly Ala Arg Arg Glu Ile Val Cys Arg
            290                 295                 300
Ala Asp Gly Thr Met Arg Phe Gly Glu Pro Thr Ser Ser Glu Thr
            305                 310                 315
Leu Ser Cys Val Ile Ile Phe Val Ile Val Tyr Tyr Ala Leu Met
            320                 325                 330
Ala Gly Val Val Trp Phe Val Val Leu Thr Tyr Ala Trp His Thr
            335                 340                 345
Ser Phe Lys Ala Leu Gly Thr Thr Tyr Gln Pro Leu Ser Gly Lys
            350                 355                 360
Thr Ser Tyr Phe His Leu Leu Thr Trp Ser Leu Pro Phe Val Leu
            365                 370                 375
Thr Val Ala Ile Leu Ala Val Ala Gln Val Asp Gly Asp Ser Val
            380                 385                 390
Ser Gly Ile Cys Phe Val Gly Tyr Lys Asn Tyr Arg Tyr Arg Ala
            395                 400                 405
Gly Phe Val Leu Ala Pro Ile Gly Leu Val Leu Ile Val Gly Gly
            410                 415                 420
Tyr Phe Leu Ile Arg Gly Val Met Thr Leu Phe Ser Ile Lys Ser
            425                 430                 435
Asn His Pro Gly Leu Leu Ser Glu Lys Ala Ala Ser Lys Ile Asn
            440                 445                 450
Glu Thr Met Leu Arg Leu Gly Ile Phe Gly Phe Leu Ala Phe Gly
            455                 460                 465
Phe Val Leu Ile Thr Phe Ser Cys His Phe Tyr Asp Phe Phe Asn
            470                 475                 480
Gln Ala Glu Trp Glu Arg Ser Phe Arg Asp Tyr Val Leu Cys Gln
            485                 490                 495
Ala Asn Val Thr Ile Gly Leu Pro Thr Lys Lys Pro Ile Pro Asp
            500                 505                 510
Cys Glu Ile Lys Asn Arg Pro Ser Leu Leu Val Glu Lys Ile Asn
            515                 520                 525
Leu Phe Ala Met Phe Gly Thr Gly Ile Ala Met Ser Thr Leu Val
            530                 535                 540
Trp Thr Lys Ala Thr Leu Leu Ile Trp Arg Arg Thr Trp Cys Arg
            545                 550                 555
Leu Thr Gly His Ser Asp Asp Glu Pro Lys Arg Ile Lys Lys Ser
            560                 565                 570
Lys Met Ile Ala Lys Ala Phe Ser Lys Arg Arg Glu Leu Leu Gln
            575                 580                 585
```

```
Asn Pro Gly Gln Glu Leu Ser Phe Ser Met His Thr Val Ser His
            590                 595                 600

Asp Gly Pro Val Ala Gly Leu Ala Phe Glu Leu Asn Glu Pro Ser
            605                 610                 615

Ala Asp Val Ser Ser Ala Trp Ala Gln His Val Thr Lys Met Val
            620                 625                 630

Ala Arg Arg Gly Ala Ile Leu Pro Gln Asp Val Ser Val Thr Pro
            635                 640                 645

Val Ala Thr Pro Val Pro Pro Glu Glu Gln Ala Asn Leu Trp Leu
            650                 655                 660

Val Glu Ala Glu Ile Ser Pro Glu Leu Glu Lys Arg Leu Gly Arg
            665                 670                 675

Lys Lys Lys Arg Arg Lys Arg Lys Lys Glu Val Cys Pro Leu Gly
            680                 685                 690

Pro Ala Pro Glu Leu His His Ser Ala Pro Val Pro Ala Thr Ser
            695                 700                 705

Ala Val Pro Arg Leu Pro Gln Leu Pro Arg Gln Lys Cys Leu Val
            710                 715                 720

Ala Ala Asn Ala Trp Gly Thr Gly Glu Pro Cys Arg Gln Gly Ala
            725                 730                 735

Trp Thr Val Val Ser Asn Pro Phe Cys Pro Glu Pro Ser Pro His
            740                 745                 750

Gln Asp Pro Phe Leu Pro Gly Ala Ser Ala Pro Arg Val Trp Ala
            755                 760                 765

Gln Gly Arg Leu Gln Gly Leu Gly Ser Ile His Ser Arg Thr Asn
            770                 775                 780

Leu Met Glu Ala Glu Leu Leu Asp Ala Asp Ser Asp Phe
            785                 790         793

(2) INFORMATION FOR SEQ ID NO:17:

(i) SEQUENCE CHARACTERISTICS:
        (A) LENGTH: 793 amino acids
        (B) TYPE: Amino Acid
        (D) TOPOLOGY: Linear (xi) SEQUENCE DESCRIPTION: SEQ ID NO:17:

Met Ala Ala Gly Arg Pro Val Arg Gly Pro Glu Leu Ala Pro Arg
 1               5                  10                  15

Arg Leu Leu Gln Leu Leu Leu Val Leu Leu Gly Gly Arg Gly
            20                  25                  30

Arg Gly Ala Ala Leu Ser Gly Asn Val Thr Gly Pro Gly Pro Arg
            35                  40                  45

Ser Ala Gly Gly Ser Ala Arg Arg Asn Ala Pro Val Thr Ser Pro
            50                  55                  60

Pro Pro Pro Leu Leu Ser His Cys Gly Arg Ala Ala His Cys Glu
            65                  70                  75

Pro Leu Arg Tyr Asn Val Cys Leu Gly Ser Ala Leu Pro Tyr Gly
            80                  85                  90

Ala Thr Thr Thr Leu Leu Ala Gly Asp Ser Asp Ser Gln Glu Glu
            95                  100                 105

Ala His Ser Lys Leu Val Leu Trp Ser Gly Leu Arg Asn Ala Pro
            110                 115                 120

Arg Cys Trp Ala Val Ile Gln Pro Leu Leu Cys Ala Val Tyr Met
            125                 130                 135
```

```
Pro Lys Cys Glu Asn Asp Arg Val Glu Leu Pro Ser Arg Thr Leu
            140                 145                 150

Cys Gln Ala Thr Arg Gly Pro Cys Ala Ile Val Glu Arg Glu Arg
            155                 160                 165

Gly Trp Pro Asp Phe Leu Arg Cys Thr Pro Asp His Phe Pro Glu
            170                 175                 180

Gly Cys Pro Asn Glu Val Gln Asn Ile Lys Phe Asn Ser Ser Gly
            185                 190                 195

Gln Cys Glu Ala Pro Leu Val Arg Thr Asp Asn Pro Lys Ser Trp
            200                 205                 210

Tyr Glu Asp Val Glu Gly Cys Gly Ile Gln Cys Gln Asn Pro Leu
            215                 220                 225

Phe Thr Glu Ala Glu His Gln Asp Met His Ser Tyr Ile Ala Ala
            230                 235                 240

Phe Gly Ala Val Thr Gly Leu Cys Thr Leu Phe Thr Leu Ala Thr
            245                 250                 255

Phe Val Ala Asp Trp Arg Asn Ser Asn Arg Tyr Pro Ala Val Ile
            260                 265                 270

Leu Phe Tyr Val Asn Ala Cys Phe Phe Val Gly Ser Ile Gly Trp
            275                 280                 285

Leu Ala Gln Phe Met Asp Gly Ala Arg Arg Glu Ile Val Cys Arg
            290                 295                 300

Ala Asp Gly Thr Met Arg Phe Gly Glu Pro Thr Ser Ser Glu Thr
            305                 310                 315

Leu Ser Cys Val Ile Ile Phe Val Ile Val Tyr Tyr Ala Leu Met
            320                 325                 330

Ala Gly Val Val Trp Phe Val Val Leu Thr Tyr Ala Trp His Thr
            335                 340                 345

Ser Phe Lys Ala Leu Gly Thr Thr Tyr Gln Pro Leu Ser Gly Lys
            350                 355                 360

Thr Ser Tyr Phe His Leu Leu Thr Trp Ser Leu Pro Phe Val Leu
            365                 370                 375

Thr Val Ala Ile Leu Ala Val Ala Gln Val Asp Gly Asp Ser Val
            380                 385                 390

Ser Gly Ile Cys Phe Val Gly Tyr Lys Asn Tyr Arg Tyr Arg Ala
            395                 400                 405

Gly Phe Val Leu Ala Pro Ile Gly Leu Val Leu Ile Val Gly Gly
            410                 415                 420

Tyr Phe Leu Ile Arg Gly Val Met Thr Leu Phe Ser Ile Lys Ser
            425                 430                 435

Asn His Pro Gly Leu Leu Ser Glu Lys Ala Ala Ser Lys Ile Asn
            440                 445                 450

Glu Thr Met Leu Arg Leu Gly Ile Phe Gly Phe Leu Ala Phe Gly
            455                 460                 465

Phe Val Leu Ile Thr Phe Ser Cys His Phe Tyr Asp Phe Phe Asn
            470                 475                 480

Gln Ala Glu Trp Glu Arg Ser Phe Arg Asp Tyr Val Leu Cys Gln
            485                 490                 495

Ala Asn Val Thr Ile Gly Leu Pro Thr Lys Lys Pro Ile Pro Asp
            500                 505                 510

Cys Glu Ile Lys Asn Arg Pro Ser Leu Leu Val Glu Lys Ile Asn
            515                 520                 525

Leu Phe Ala Met Phe Gly Thr Gly Ile Ala Met Ser Thr Trp Val
```

```
                         530                 535                 540
Trp Thr Lys Ala Thr Leu Leu Ile Trp Arg Arg Thr Trp Cys Arg
                545                 550                 555
Leu Thr Gly His Ser Asp Asp Glu Pro Lys Arg Ile Lys Lys Ser
                560                 565                 570
Lys Met Ile Ala Lys Ala Phe Ser Lys Arg Arg Glu Leu Leu Gln
                575                 580                 585
Asn Pro Gly Gln Glu Leu Ser Phe Ser Met His Thr Val Ser His
                590                 595                 600
Asp Gly Pro Val Ala Gly Leu Ala Phe Glu Leu Asn Glu Pro Ser
                605                 610                 615
Ala Asp Val Ser Ser Ala Trp Ala Gln His Val Thr Lys Met Val
                620                 625                 630
Ala Arg Arg Gly Ala Ile Leu Pro Gln Asp Val Ser Val Thr Pro
                635                 640                 645
Val Ala Thr Pro Val Pro Pro Glu Glu Gln Ala Asn Leu Trp Leu
                650                 655                 660
Val Glu Ala Glu Ile Ser Pro Glu Leu Glu Lys Arg Leu Gly Arg
                665                 670                 675
Lys Lys Lys Arg Arg Lys Arg Lys Lys Glu Val Cys Pro Leu Gly
                680                 685                 690
Pro Ala Pro Glu Leu His His Ser Ala Pro Val Pro Ala Thr Ser
                695                 700                 705
Ala Val Pro Arg Leu Pro Gln Leu Pro Arg Gln Lys Cys Leu Val
                710                 715                 720
Ala Ala Asn Ala Trp Gly Thr Gly Glu Pro Cys Arg Gln Gly Ala
                725                 730                 735
Trp Thr Val Val Ser Asn Pro Phe Cys Pro Glu Pro Ser Pro His
                740                 745                 750
Gln Asp Pro Phe Leu Pro Gly Ala Ser Ala Pro Arg Val Trp Ala
                755                 760                 765
Gln Gly Arg Leu Gln Gly Leu Gly Ser Ile His Ser Arg Thr Asn
                770                 775                 780
Leu Met Glu Ala Glu Leu Leu Asp Ala Asp Ser Asp Phe
                785                 790             793

(2) INFORMATION FOR SEQ ID NO:18:

(i) SEQUENCE CHARACTERISTICS:
        (A) LENGTH: 228 base pairs
        (B) TYPE: Nucleic Acid
        (C) STRANDEDNESS: Single
        (D) TOPOLOGY: Linear (xi) SEQUENCE DESCRIPTION: SEQ ID NO:18:

CTGGGGCTGT CCAGTTACCC AACGGCTAC CCCTTCCTCT TCTGGGAGCA         50

GTACATCGGC CTCCGCCACT GGCTGCTGCT GTTCATCAGC GTGGTGTTGG        100

CCTGCACATT CCTCGTGTGC GCTGTCTTCC TTCTGAACCC CTGGACGGCC        150

GGGATCATTG TGATGGTCCT GGCGCTGATG ACGGTCGAGC TGTTCGGCAT        200

GATGGGCCTC ATCGGAATCA AGCTCAGT                                228

(2) INFORMATION FOR SEQ ID NO:19:

(i) SEQUENCE CHARACTERISTICS:
        (A) LENGTH: 18 base pairs
```

(B) TYPE: Nucleic Acid
            (C) STRANDEDNESS: Single
            (D) TOPOLOGY: Linear (xi) SEQUENCE DESCRIPTION: SEQ ID NO:19:

AGGCGGGGGA TCACAGCA                                                    18

(2) INFORMATION FOR SEQ ID NO:20:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:20:

ATACCAAAGA GTTCCACT                                                    18

(2) INFORMATION FOR SEQ ID NO:21:

(i) SEQUENCE CHARACTERISTICS:
            (A) LENGTH: 45 base pairs
            (B) TYPE: Nucleic Acid
            (C) STRANDEDNESS: Single
            (D) TOPOLOGY: Linear (xi) SEQUENCE DESCRIPTION: SEQ ID NO:21:

CTGCGGCGCT GCTTCCTGCT GGCCGTCTGC ATCCTGCTGG TGTGC                      45

(2) INFORMATION FOR SEQ ID NO:22:

(i) SEQUENCE CHARACTERISTICS:
            (A) LENGTH: 45 base pairs
            (B) TYPE: Nucleic Acid
            (C) STRANDEDNESS: Single
            (D) TOPOLOGY: Linear (xi) SEQUENCE DESCRIPTION: SEQ ID NO:22:

AGAGCACAGA CGAGGAAAGT GCACACCAGC AGGATGCAGA CGGCC                      45

(2) INFORMATION FOR SEQ ID NO:23:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (xi) SEQUENCE DESCRIPTION: SEQ ID NO:23:

ACTCCTGACT TGTAGCAGAT T                                                21

(2) INFORMATION FOR SEQ ID NO:24:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (xi) SEQUENCE DESCRIPTION: SEQ ID NO:24:

AGGCTGCATA CACCTCTCAG A                                                21

(2) INFORMATION FOR SEQ ID NO:25:

(i) SEQUENCE CHARACTERISTICS:
            (A) LENGTH: 18 base pairs
            (B) TYPE: Nucleic Acid (C) STRANDEDNESS: Single
        (D) TOPOLOGY: Linear (xi) SEQUENCE DESCRIPTION: SEQ ID NO:25:

GCTTAGGCCC GAGGAGAT                                                 18

(2) INFORMATION FOR SEQ ID NO:26:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO:26:

AACTCACAAC TTTCTCTCCA                                               20

(2) INFORMATION FOR SEQ ID NO:27:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO:27:

GGATTCTAAT ACGACTCACT ATAGGGCCCA ATGGCCTAAA CCGACTGC                48

(2) INFORMATION FOR SEQ ID NO:28:

(i) SEQUENCE CHARACTERISTICS:
        (A) LENGTH: 46 base pairs
        (B) TYPE: Nucleic Acid
        (C) STRANDEDNESS: Single
        (D) TOPOLOGY: Linear (xi) SEQUENCE DESCRIPTION: SEQ ID NO:28:

CTATGAAATT AACCCTCACT AAAGGGACCC ACGGCCTCTC CTCACA                  46

(2) INFORMATION FOR SEQ ID NO:29:

(i) SEQUENCE CHARACTERISTICS:
        (A) LENGTH: 449 amino acids
        (B) TYPE: Amino Acid
        (D) TOPOLOGY: Linear (xi) SEQUENCE DESCRIPTION: SEQ ID NO:29:

Met Glu Ser Pro Arg Ala Thr Gln Thr Pro Glu Ser Pro Lys Leu
 1               5                  10                  15

Ser Gln Pro Arg Ala His Leu Ser Ala His Gln Ala Pro Ser Pro
                20                  25                  30

Ala Ala Leu Pro Gly Tyr Pro Ala Met Ser Pro Ala Trp Leu Arg
                35                  40                  45

Pro Arg Leu Arg Phe Cys Leu Phe Leu Leu Leu Leu Leu Leu Val
                50                  55                  60

Pro Ala Ala Arg Gly Cys Gly Pro Gly Arg Val Val Gly Ser Arg
                65                  70                  75

Arg Arg Pro Pro Arg Lys Leu Val Pro Leu Ala Tyr Lys Gln Phe
                80                  85                  90

Ser Pro Asn Val Pro Glu Lys Thr Leu Gly Ala Ser Gly Arg Tyr
                95                  100                 105

Glu Gly Lys Ile Ala Arg Ser Ser Glu Arg Phe Lys Glu Leu Thr
                110                 115                 120

```
Pro Asn Tyr Asn Pro Asp Ile Ile Phe Lys Asp Glu Glu Asn Thr
            125                 130                 135

Gly Ala Asp Arg Leu Met Thr Gln Arg Cys Lys Asp Arg Leu Asn
            140                 145                 150

Ser Leu Ala Ile Ser Val Met Asn Gln Trp Pro Gly Val Lys Leu
            155                 160                 165

Arg Val Thr Glu Gly Trp Asp Glu Asp Gly His His Ser Glu Glu
            170                 175                 180

Ser Leu His Tyr Glu Gly Arg Ala Val Asp Ile Thr Thr Ser Asp
            185                 190                 195

Arg Asp Arg Asn Lys Tyr Gly Leu Leu Ala Arg Leu Ala Val Glu
            200                 205                 210

Ala Gly Phe Asp Trp Val Tyr Tyr Glu Ser Lys Ala His Val His
            215                 220                 225

Cys Ser Val Lys Ser Glu His Ser Ala Ala Lys Thr Gly Gly
            230                 235                 240

Cys Phe Pro Ala Gly Ala Gln Val Arg Leu Glu Asn Gly Glu Arg
            245                 250                 255

Val Ala Leu Ser Ala Val Lys Pro Gly Asp Arg Val Leu Ala Met
            260                 265                 270

Gly Glu Asp Gly Thr Pro Thr Phe Ser Asp Val Leu Ile Phe Leu
            275                 280                 285

Asp Arg Glu Pro Asn Arg Leu Arg Ala Phe Gln Val Ile Glu Thr
            290                 295                 300

Gln Asp Pro Pro Arg Arg Leu Ala Leu Thr Pro Ala His Leu Leu
            305                 310                 315

Phe Ile Ala Asp Asn His Thr Glu Pro Ala Ala His Phe Arg Ala
            320                 325                 330

Thr Phe Ala Ser His Val Gln Pro Gly Gln Tyr Val Leu Val Ser
            335                 340                 345

Gly Val Pro Gly Leu Gln Pro Ala Arg Val Ala Ala Val Ser Thr
            350                 355                 360

His Val Ala Leu Gly Ser Tyr Ala Pro Leu Thr Arg His Gly Thr
            365                 370                 375

Leu Val Val Glu Asp Val Val Ala Ser Cys Phe Ala Ala Val Ala
            380                 385                 390

Asp His His Leu Ala Gln Leu Ala Phe Trp Pro Leu Arg Leu Phe
            395                 400                 405

Pro Ser Leu Ala Trp Gly Ser Trp Thr Pro Ser Glu Gly Val His
            410                 415                 420

Trp Tyr Pro Gln Met Leu Tyr Arg Leu Gly Arg Leu Leu Glu
            425                 430                 435

Glu Ser Thr Phe His Pro Leu Gly Met Ser Gly Ala Gly Ser
            440                 445             449

(2) INFORMATION FOR SEQ ID NO:30:

(i) SEQUENCE CHARACTERISTICS:
        (A) LENGTH: 228 base pairs
        (B) TYPE: Nucleic Acid
        (C) STRANDEDNESS: Single
        (D) TOPOLOGY: Linear (xi) SEQUENCE DESCRIPTION: SEQ ID NO:30:

CTGGGGCTGT CCAGTTACCC CAACGGCTAC CCCTTCCTCT TCTGGGAGCA            50
```

-continued

```
GTACATCGGC CTCCGCCACT GGCTGCTGCT GTTCATCAGC GTGGTGTTGG          100

CCTGCACATT CCTCGTGTGC GCTGTCTTCC TTCTGAACCC CTGGACGGCC          150

GGGATCATTG TGATGGTCCT GGCGCTGATG ACGGTCGAGC TGTTCGGCAT          200

GATGGGCCTC ATCGGAATCA AGCTCAGT                                  228

(2) INFORMATION FOR SEQ ID NO:31:

(i) SEQUENCE CHARACTERISTICS:
        (A) LENGTH: 32 base pairs
        (B) TYPE: Nucleic Acid
        (C) STRANDEDNESS: Single
        (D) TOPOLOGY: Linear (xi) SEQUENCE DESCRIPTION: SEQ ID NO:31:

TCGACAAGCA GGGAACACCC AAGTAGAAGC TC                              32

(2) INFORMATION FOR SEQ ID NO:32:

(i) SEQUENCE CHARACTERISTICS:
        (A) LENGTH: 32 base pairs
        (B) TYPE: Nucleic Acid
        (C) STRANDEDNESS: Single
        (D) TOPOLOGY: Linear (xi) SEQUENCE DESCRIPTION: SEQ ID NO:32:

TCGACAAGCA GGGAAGTGGG AAGTAGAAGC TC                              32
```

NUCLEIC ACID ENCODING PATCHED-2

FIELD OF THE INVENTION

The present invention relates generally to signaling molecules, specifically to signaling and mediator molecules in the hedgehog (hh) cascade which are involved in cell proliferation and differentiation.

BACKGROUND OF THE INVENTION

Development of multicellular organisms depends, at least in part, on mechanisms which specify, direct or maintain positional information to pattern cells, tissues, or organs. Various secreted signaling molecules, such as members of the transforming growth factor-beta (TGF-β), Wnt, fibroblast growth factors and hedgehog families have been associated with patterning activity of different cells and structures in Drosophila as well as in vertebrates. Perrimon, *Cell*: 80: 517–520 (1995).

Segment polarity genes were first discovered in Drosophila, which when mutated caused a change in the pattern of structures of the body segments. These changes affected the pattern along the head to tail axis. Hedgehog (Hh) was first identified as a segment-polarity gene by a genetic screen in *Drosophila melanogaster*, Nusslein-Volhard et al., *Roux. Arch. Dev. Biol.* 193: 267–282 (1984), that plays a wide variety of developmental functions. Perrimon, supra. Although only one Drosophila Hh gene has been identified, three mammalian Hh homologues have been isolated: Sonic Hh (Shh), Desert Hh (Dhh) and Indian Hh (Ihh), Echelard et al., *Cell* 75: 1417–30 (1993); Riddle et al, *Cell* 75: 1401–16 (1993). Shh is expressed at high level in the notochord and floor plate of developing vertebrate embryos, and acts to establish cell fate in the developing limb, somites and neural tube. In vitro explant assays as well as ectopic expression of Shh in transgenic animals show that SHh plays a key role in neural tube patterning, Echelard et al. (1993), supra.; Ericson et al., *Cell* 81: 747–56 (1995); Marti et al., *Nature* 375: 322–5 (1995); Roelink et al. (1995), supra; Hynes et al., *Neuron* 19: 15–26 (1997). Hh also plays a role in the development of limbs (Krauss et al., *Cell* 75: 1431–44 (1993); Laufer et al., *Cell* 79, 993–1003 (1994)), somites (Fan and Tessier-Lavigne, *Cell* 79, 1175–86 (1994); Johnson et al., *Cell* 79: 1165–73 (1994)), lungs (Bellusci et al., *Develop.* 124: 53–63 (1997) and skin (Oro et al., *Science* 276: 817–21 (1997). Likewise, Ihh and Dhh are involved in bone, gut and germinal cell development, Apelqvist et al., *Curr. Biol.* 7: 801–4 (1997); Bellusci et al., *Development* 124: 53–63 (1997); Bitgood et al., *Curr. Biol.* 6: 298–304 (1996); Roberts et al., *Development* 121: 3163–74 (1995). Specifically, Ihh has been implicated in chondrocyte development [Vortkamp, A. et al., *Science* 273: 613–22 (1996)] while Dhh plays a key role in testis development. Bitgood et al., supra. With the exception of the gut, in which both Ihh and Shh are expressed, the expression patterns of the hedgehog family members do not overlap. Bitgood et al., supra.

At the cell surface, Hh function appears to be mediated by a multicomponent receptor complex involving patched (ptch) and smoothened (smo), two multi-transmembrane proteins initially identified as segment polarity genes in Drosophila and later characterized in vertebrates. Nakano et al., *Nature* 341: 508–513 (1989); Goodrich et al., *Genes Dev.* 10: 301–312 (1996); Marigo et al., *Develop.* 122: 1225–1233 (1996); van den Heuvel, M. & Ingham, P. W., *Nature* 382: 547–551 (1996); Alcedo, J. et al., *Cell* 86: 221–232 (1996); Stone, D. M. et al., *Nature* 384: 129–34 (1996). Upon binding of Hh to Ptch, the normal inhibitory effect of Ptch on Smo is relieved, allowing Smo to transduce the Hh signal across the plasma membrane. It remains to be established if the Ptch/Smo receptor complex mediates the action of all 3 mammalian hedgehogs or if specific components exist. Interestingly, a second murine Ptch gene, Ptch-2 was recently isolated [Motoyama, J. et al., *Nature Genetics* 18: 104–106 (1998)], but its function as a Hh receptor has not been established. In order to characterize Ptch-2 and compare it to Ptch with respect to the biological function of the various Hh family members, Applicants have isolated the human Ptch-2 gene. Biochemical analysis of Ptch and Ptch-2 show that both bind to all members of the Hh family with similar affinity and that both molecules can form a complex with Smo. However, the expression patterns of Ptch-2 and Ptch do not overlap. While Ptch is expressed throughout the mouse embryo, Ptch-2 is found mainly in spermatocytes which require Desert Hedgehog (Dhh) for proper development suggesting that Ptch-2 mediates Dhh's activity in the testis. Chromosomal localization of Ptch-2 places it on chromosome 1p33–34, a region deleted in some germ cell tumors, raising the possibility that Ptch-2 may be a tumor suppressor in Dhh target cells.

SUMMARY OF THE INVENTION

In one embodiment, the invention provides an isolated nucleic acid molecule having at least about 80% sequence identity to (a) a DNA molecule encoding a patched-2 polypeptide comprising the sequence of amino acids 1 to 1203 of FIG. 1, or (b) the complement of the DNA molecule of (a); and encoding a polypeptide having patched-2 biological activity. The sequence identity preferably is >91%, more preferably about 92%, most preferably about 95%. In one aspect, the isolated nucleic acid has at least >91%, preferably at least about 92%, and even more preferably at least about 95% sequence identity with a polypeptide having amino acid residues 1 to about 1203 of FIG. 1. In a further aspect, the isolated nucleic acid molecule comprises DNA encoding a human patched-2 polypeptide having amino acid residues 1 to about 1203 of FIG. 1. In yet another aspect, the invention provides for an isolated nucleic acid comprising DNA having at least a 95% sequence identity to (a) a DNA molecule encoding the same mature polypeptide encoded by the cDNA in ATCC Deposit No. 209778 (designation: pRK7.hptc2.Flag-1405), alternatively the coding sequence of clone pRK6.hptc2.Flag-1405, deposited under accession number ATCC 209778. In a still further aspect, the invention provides for a nucleic acid comprising human patched-2 encoding sequence of the cDNA in ATCC deposit No. 209778 (designation: pRK7.hptc2.Flag-1405) or a sequence which hybridizes thereto under stringent conditions.

In another embodiment, the invention provides a vector comprising DNA encoding a human patched-2 polypeptide. A host cell comprising such a vector is also provided. By way of example, the host cells may be mammalian cells, (e.g. CHO cells), prokaryotic cells (e.g., *E. coli*) or yeast cells (e.g., *Saccharomyces cerevisiae*). A process for producing patched-2 polypeptides is further provided and comprises culturing host cells under conditions suitable for expression of patched-2 and recovering the same from the cell culture.

In yet another embodiment, the invention provides an isolated patched-2 polypeptide. In particular, the invention provides isolated native sequence patched-2 polypeptide, which in one embodiment is a human patched-2 including an amino acid sequence comprising residues 1 to about 1203 of FIG. 1. Human patched-2 polypeptides with or without the initiating methionine are specifically included. Alternatively, the invention provides a human patched-2 polypeptide encoded by the nucleic acid deposited under accession number ATCC Deposit No. 209778.

In yet another embodiment, the invention provides chimeric molecules comprising a patched-2 polypeptide patched-2 to a heterologous polypeptide or amino acid sequence. An example of such a chimeric molecule comprises a patched-2 polypeptide patched-2 to an epitope tag sequence or a constant region of an immunoglobulin.

In yet another embodiment, the invention provides expressed sequence tag (EST) comprising the nucleotide sequences identified in FIG. 2A (905531) (SEQ ID NO:3) and FIG. 2B (1326258) (SEQ ID NO:5).

In yet another embodiment, the invention provides for alternatively spliced variants of human patched-2 having patched-2 biological activity.

In yet another embodiment, the invention provides for method of using patched-2 for the treatment of disorders which are mediated at least in part by Hedgehog (Hh), especially Desert hedgehog (Dhh). In particular, testicular cancer: In yet another embodiment, the invention provides a method of using antagonists or agonists of patched-2 for treating disorders or creating a desirable physiological condition effected by blocking Hh signaling, especially Dhh signaling. (E.g, contraception).

BRIEF DESCRIPTION OF THE DRAWINGS

FIGS. 1A–1E show the nucleotide (SEQ ID NO: 1) and derived amino acid (SEQ ID NO:2) sequence of a native sequence of human Ptch-2.

FIG. 2A shows EST 905531 (SEQ ID NO:3) and FIG. 2B shows EST 1326258 (SEQ ID NO:5) in alignment with human Ptch SEQ ID NO:18. These EST's were used in the cloning of human full-length Ptch-2 SEQ ID NO:1.

FIG. 3 shows a comparison between human Ptch (SEQ ID NO:4) and Ptch-2 (SEQ ID NO:2). Gaps introduced for optimal alignment are indicated by dashes. Identical amino acids are boxed. The 12 transmembrane domains are indicated by the gray boxes, all of which are conserved between the two sequences. Alignment results between the two sequences indicate 53% identity. The most significant difference is a shorter C-terminal intracellular domain in human Ptch-2 (SEQ ID NO:2) in comparison with human Ptch (SEQ ID NO:4).

FIG. 6(f) shows low magnification of testis section hybridized with FuRK SEQ ID NO:10 encoding a nucleic acid. Scale bar: a, b, c: 0.05 mm; d, e, f: 0.33 mm.

FIGS. 8A–D are a sequence comparison between human Ptch-2 (SEQ ID NO:2) and murine Ptch-2 (SEQ ID NO:7), which indicates that there is about 91% identity between the two sequences.

FIGS. 10A–D are a partial sequence representing clone 3A (SEQ ID NO:8), a partial patched-2 fragment which was initially isolated from a fetal brain library.

FIGS. 11A–B are a partial sequence representing clone 16.1 (SEQ ID NO:9), a partial patched-2 fragment which isolated from a testis library.

DETAILED DESCRIPTION OF THE PREFERRED EMBODIMENTS

I. Definitions

Figure 4:
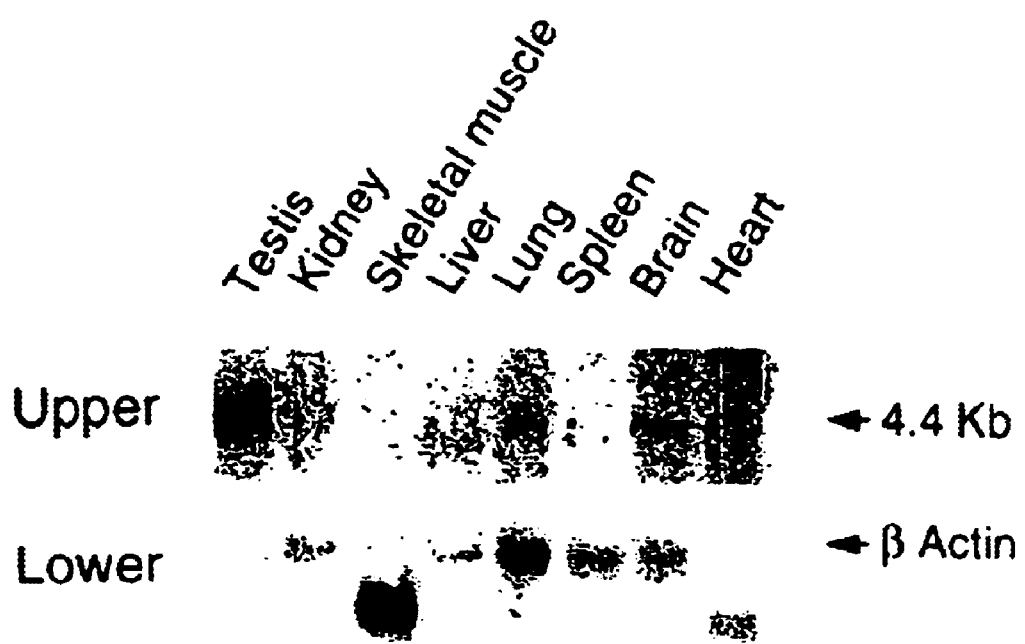
FIG. 4 shows a northern blot of Ptch-2 (SEQ ID NO:2) which indicates expression is limited to the testis. Multiple human fetal and adult tissue northern blots were probe fragments corresponding to the 3'-untranslated region of murine Ptch-2.

The terms "patched-2" and "patched-2 polypeptide" when used herein encompass native sequence patched-2 and patched-2 variants (which are further defined herein) having patched-2 biological activity. Patched-2 may be isolated from a variety of sources, such as from testes tissue types or from another source, or prepared by recombinant or synthetic methods.

Figure 1B:
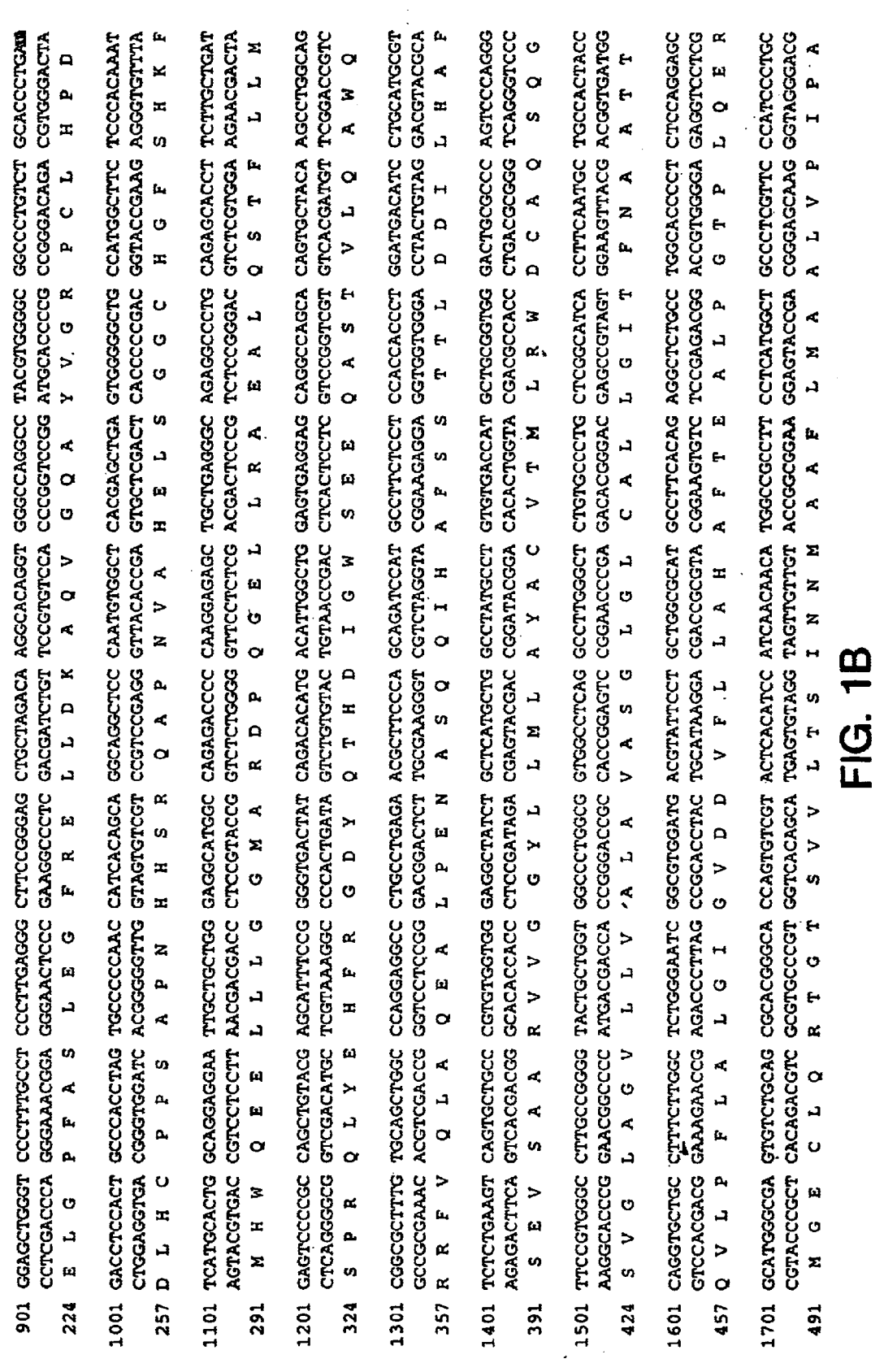

A "native sequence patched-2" comprises a polypeptide having the same amino acid sequence as a human patched-2 derived from nature. Such native sequence patched-2 can be isolated from nature or can be produced by recombinant and/or synthetic means. The term "native sequence vertebrate patched-2" specifically encompasses naturally occurring truncated forms of human patched-2, naturally occurring variant forms (e.g., alternatively spliced forms) and naturally-occurring allelic variants of human patched-2. Thus, one embodiment of the invention, the native sequence patched-2 is a mature or full-length native Ptch-2 comprising amino acids 1 to 1203 of FIG. 1 (SEQ ID NO:2) with or without the initiating methionine at position 1.

"Patched-2 variant" means an active human patched-2 as defined below having at least >91% amino acid sequence identity to (a) a DNA molecule encoding a patched-2 polypeptide, or (b) the complement of the DNA molecule of (a). In a particular embodiment, the patched-2 variant has at least >91% amino acid sequence homology with the human Ptch-2 (SEQ ID NO:2) having the deduced amino acid sequence shown in FIG. 1 for a full-length native sequence human patched-2. Such patched-2 variants include, without limitation, patched-2 polypeptides wherein one or more amino acid residues are added, or deleted, at the N- or C-terminus of the sequence of FIG. 1 (SEQ ID NO:2). Preferably, the nucleic acid or amino acid sequence identity is at least about 92%, more preferably at least about 93%, and even more preferably at least about 95%.

"Percent (%) amino acid sequence identity" with respect to the patched-2 sequences identified herein is defined as the percentage of amino acid residues in a candidate sequence that are identical with the amino acid residues in the patched-2 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST-2 software that are set to their default parameters. Those skilled in the art can determine appropriate parameters for measuring alignment, including any algorithms needed to achieve maximal alignment over the full length of the sequences being compared.

"Percent (%) nucleic acid sequence identity" with respect to the patched-2 sequences identified herein is defined as the percentage of nucleotides in a candidate sequence that are identical with the nucleotides in the patched-2 sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST-2 software that are set to their default parameters. Those skilled in the art can determine appropriate parameters for measuring alignment, including any algorithms needed to achieve maximal alignment over the full length of the sequences being compared.

The term "epitope tagged" when used herein refers to a chimeric polypeptide comprising patched-2 polypeptide, or a portion thereof, patched-2 to a "tag polypeptide". The tag polypeptide has enough residues to provide an epitope against which an antibody can be made, yet is short enough such that it does not interfere with activity of the patched-2 polypeptide. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

As used herein, the term "immunoadhesin" designates antibody-like molecules which combine the binding specificity of a heterologous protein (an "adhesin") with the effector functions of immunoglobulin constant domains. Structurally, the immunoadhesin comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesins may be obtained from any immunoglobulin, such as IgG-1, IgG-2, IgG-3 or IgG4 subtypes, IgA (including IgA-1 and IgA-2, IgE, IgD or IgM. Immunoadhesion reported in the literature include fusions of the T cell receptor* [Gascoigne et al., *Proc. Natl. Acad. Sci. USA* 84: 2936–2940 (1987)]; CD4* [Capron et al., *Nature* 337: 525–531 (1989); Traunecker et al., *Nature* 339: 68–70 (1989); Zettmeissl et al., *DNA Cell Biol. USA* 9: 347–353 (1990); Byrn et al., *Nature* 344, 667–670 (1990)]; L-selectin (homing receptor) [Watson et al., *J. Cell. Biol.* 110, 2221–2229 (1990); Watson et al., *Nature* 349, 164–167 (1991)]; CD44* [Aruffo et al., *Cell* 61, 1303–1313 (1990)]; CD28* and B7* [Linsley et al., *J. Exp. Med.* 173, 721–730 (1991)]; CTLA-4* [Lisley et al., *J. Exp. Med.* 174, 561–569 (1991)]; CD22* [Stamenkovic et al., *Cell* 66. 1133–1144 (1991)]; TNF receptor [Ashkenazi et al., *Proc. Natl. Acad. Sci. USA* 88, 10535–10539 (1991); Lesslauer et al., *Eur. J. Immunol.* 27, 2883–2886 (1991); Peppel et al., *J. Exp. Med.* 174, 1483–1489 (1991)]; NP receptors [Bennett et al., *J. Biol. Chem.* 266, 23060–23067 (1991)]; IgE receptor α-chain* [Ridgway and Gorman, *J. Cell. Biol.* 115, abstr. 1448 (1991)]; HGF receptor [Mark, M. R. et al., *J. Biol. Chem.*, 267(36): 26166–26171 (1992) ], where the asterisk (*) indicates that the receptor is a member of the immunoglobulin superfamily.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends upon the ability of denatured DNA to reanneal when complementary strands are present in an environment near but below their $T^m$ (melting temperature). The higher the degree of desired homology between the probe and hybridizable sequence, the higher the relative temperature which can be used. As a result, it follows that higher relative temperatures would tend to make the reaction conditions more stringent, while lower temperatures less so. Moreover, stringency is also inversely proportional to salt concentrations. For additional details and explanation of stringency of hybridization reactions, see Ausubel et al., *Current Protocols in Molecular Biology* (1995).

"Stringent conditions," as defined herein may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (vol/vol) formamide with 0.1% bovine serum albumin/0.1% Ficoll/ 0.1% polyvinylpyrrolidone/50 mM sodium phosphate buffer at pH 6.5 with 750 mM sodium chloride, 75 mM sodium citrate at 42° C.; (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the vertebrate patched-2 natural environment will not be present. Ordinarily, however, isolated polypeptide will be prepared by at least one purification step.

An "isolated" patched-2 nucleic acid molecule is a nucleic acid molecule that is identified and separated from at least one contaminant nucleic acid molecule with which it is ordinarily associated in the natural source of the patched-2 nucleic acid. An isolated patched-2 nucleic acid molecule is other than in the form or setting in which it is found in nature. Isolated patched-2 nucleic acid molecules therefore are distinguished from the corresponding native patched-2 nucleic acid molecule as it exists in natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$ and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods [see, e.g. U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity [U.S. Pat. No. 4,816,567; Cabilly et al.; Morrison et al., *Proc. Natl. Acad. Sci. USA* 81, 6851–6855 (1984)].

"Humanized" forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, corresponding non-human residues replace Fv framework residues of the human immunoglobulin. Furthermore, humanized antibody may comprise residues that are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature* 321, 522–525 (1986); Riechmann et al., *Nature* 332, 323–327 (1988); Presta, *Curr. Op. Struct. Biol.* 2 593–596 (1992) and U.S. Pat. No. 5,225,539 (Winter) issued Jul. 6, 1993.

"Active" or "activity" for the purposes herein refers to form(s) of patched-2 which retain the biologic and/or immunologic activities of native or naturally occurring patched-2. A preferred activity is the ability to bind to and affect, e.g., block or otherwise modulate, hedgehog (Hh), especially desert hedgehog (Dhh) signaling. For example, the regulation of the pathogenesis of testicular cancer, male spermatocyte formation and basal cell carcinoma.

The term "antagonist" is used herein in the broadest sense to include any molecule which blocks, prevents, inhibits, neutralizes the normal functioning of patched-2 in the hedgehog (Hh) signaling pathway. One particular form of antagonist includes a molecule that interferes with the interaction between Dhh and patched-2. Alternatively, an antagonist could also be a molecule which increases the levels of patched-2. In a similar manner, the term "agonist" is used herein to include any molecule which promotes, enhances or stimulates the binding of a Hh to patched-2 in the Hh signaling pathway or otherwise upregulates it (e.g., blocking binding of Ptch 2 (SEQ ID NO:2) to Smo (SEQ ID NO:17). Suitable molecules that affect the protein-protein interaction of Hh and patched-2 and its binding proteins include fragments of the latter or small bioorganic molecules, e.g., peptidomimetics, which will prevent or enhance, as the case may be, the binding of Hh to patched-2.

Non-limiting examples include proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Another preferred form of antagonist includes antisense oligonucleotides that inhibit proper transcription of wild type patched-2.

The term "modulation" or "modulating" means upregulation or downregulation of a signaling pathway. Cellular processes under the control of signal transduction may include, but are not limited to, transcription of specific genes; normal cellular functions, such as metabolism, proliferation, differentiation, adhesion, apoptosis and survival, as well as abnormal processes, such as transformation, blocking of differentiation and metastasis.

The techniques of "polymerase chain reaction," or "PCR", as used herein generally refers to a procedure wherein minute amounts of a specific piece of nucleic acid, RNA and/or DNA are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR sequences form total genomic DNA, and cDNA transcribed from total cellular RNA, bacteriophage, or plasmid sequences, etc. See generally Mullis et al., *Cold Spring Harbor Symp. Quant. Biol.* 51: 263 (1987); Erlich, Ed., PCR Technology, (Stockton Press, NY, 1989). As used herein, PCR is considered to be one, but not the only, example of a nucleic acid test sample comprising the use of a known nucleic acid as a primer and a nucleic acid polymerase to amplify or generate a specific piece of nucleic acid.

II. Compositions and Methods of the Invention
A. Full-length Patched-2

The present invention provides newly identified and isolated nucleotide sequences encoding polypeptides referred to in the present application as patched-2. In particular, Applicants have identified and isolated cDNA encoding a human patched-2 polypeptide, as disclosed in further detail in the Examples below. Using BLAST, BLAST-2 and FastA sequence alignment computer programs (set to the default parameters), Applicants found that a full-length native sequence human patched-2 (i.e., Ptch-2 in FIG. 3, SEQ ID NO:2) has 53% amino acid sequence identity with a human patched (i.e., Ptch, SEQ ID NO:4). Moreover a human full-length patched-2 (i.e., Ptch-2, SEQ ID NO:2) has about a 91% sequence identity with murine Ptch-2 (SEQ ID NO:7) (FIG. 8). Accordingly, it is presently believed that the human patched-2 (i.e., Ptch-2, SEQ ID NO:2) disclosed in the present application is a newly identified member of the mammalian hedgehog signaling cascade, specifically Desert hedgehog.

Figure 1D:
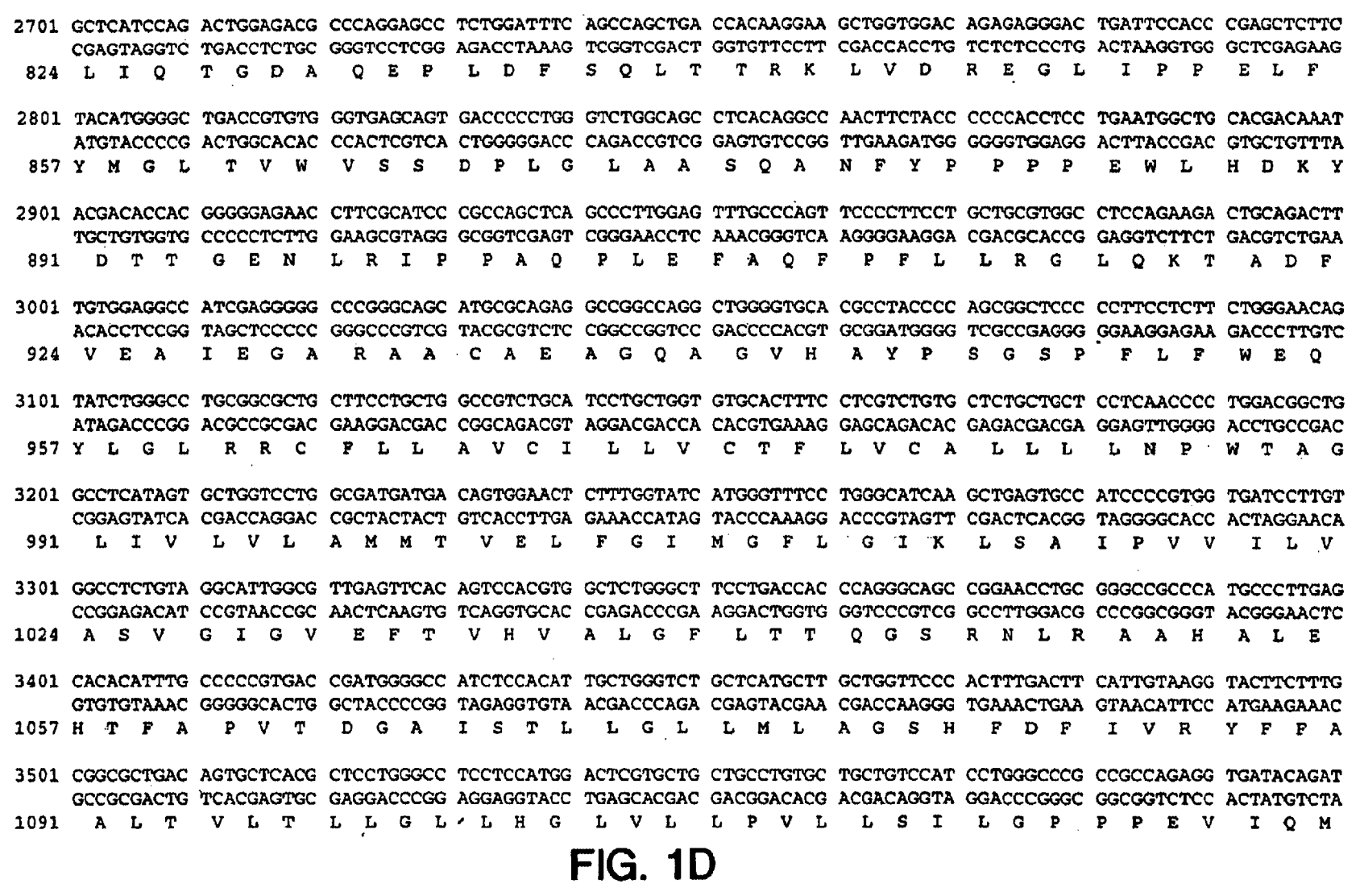

The full-length native sequence of human patched-2 gene, or portions thereof, may be used as hybridization probes for a cDNA library to isolate the full-length gene or to isolate still other vertebrate homolog genes (for instance, those encoding naturally-occurring variants of patched-2 or patched-2 from other species) which have a desired sequence identity to the human patched-2 sequence disclosed in FIG. 1 (SEQ ID NO:2). Optionally, the length of the probes will be about 20 to about 50 bases. The hybridization probes may be derived from the nucleotide sequence of FIG. 1 (SEQ ID NO:1) or from genomic sequences including promoters, enhancer elements and introns of native sequence vertebrate patched-2. By way of example, a screening method will comprise isolating the coding region of the vertebrate patched-2 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the vertebrate patched-2 gene of the present invention can be used to screen libraries of human cDNA, genomic DNA or mRNA to determine which members of such libraries the probe hybridizes to.

B. Patched-2 Variants

In addition to the full-length native sequence patched-2 described herein, it is contemplated that patched-2 variants can be prepared. Patched-2 variants can be prepared by introducing appropriate nucleotide changes into a known patched-2 DNA, or by synthesis of the desired patched-2 polypeptides. Those skilled in the art will appreciate that amino acid changes may alter post-translational processes of patched-2.

Variations in the native full-length sequence patched-2 or in various domains of the patched-2 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the patched-2 that results in a change in the amino acid sequence of patched-2 as compared with the native sequence patched-2. Optionally, the variation is by substitution of at least one amino acid with any other amino acid in one or more of the domains of patched-2. Guidance in determining which amino acid residue may be inserted, substituted or deleted without adversely affecting the desired activity may be found by comparing the sequence of the patched-2 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10: 6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the vertebrate patched-2 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

Figure 3C:
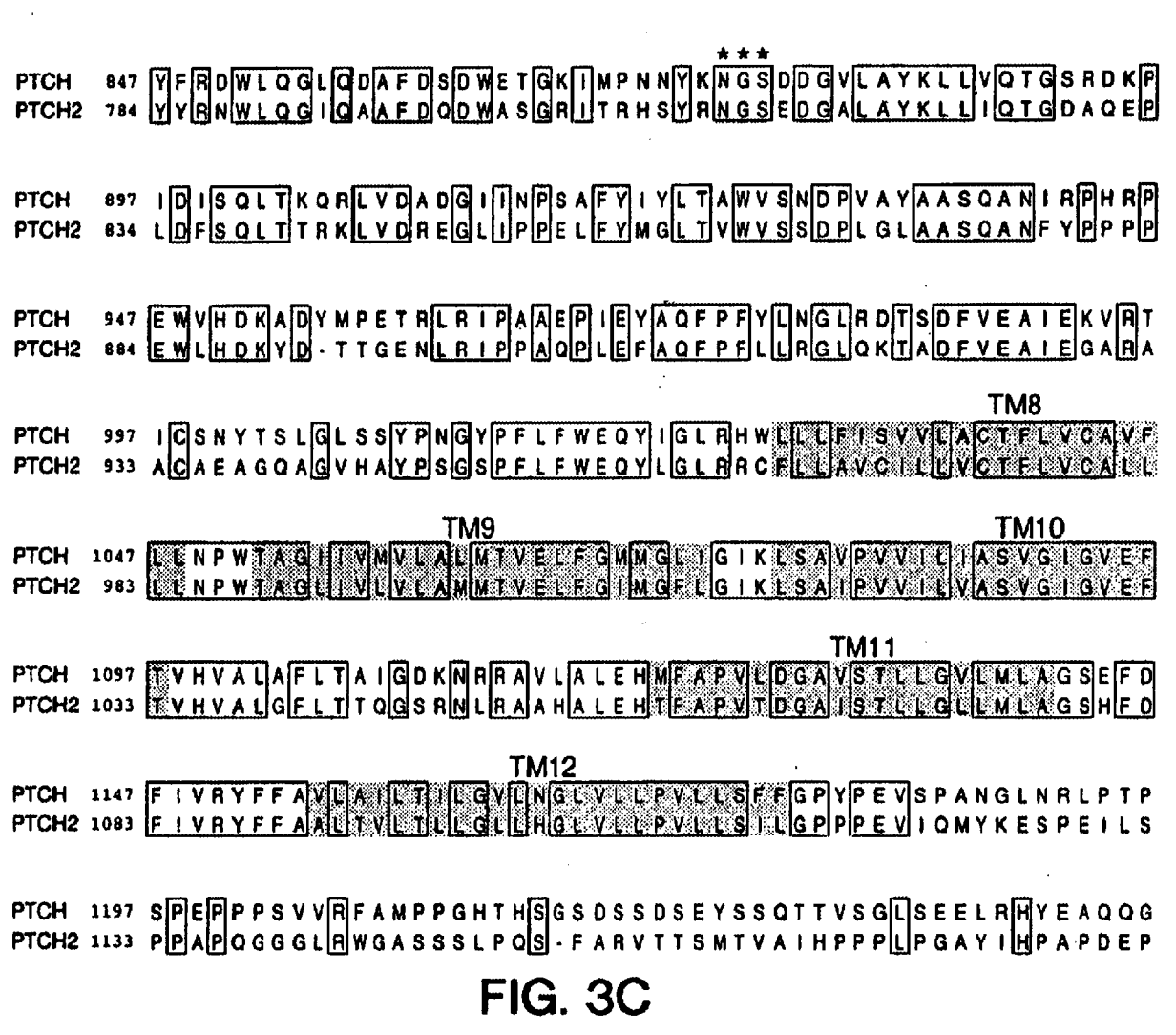

In the comparison between human patched and patched-2 sequences depicted in FIG. 3 (e.g., Ptch, SEQ ID NO:4 and Ptch-2, SEQ ID NO:2), the 12 transmembrane domains are identified in gray, while identical residues are boxed. Gaps are indicated by dashes (-) and are inserted to maximize the total identity score between the two sequences.

C. Modifications of patched-2

Covalent modifications of patched-2 are included within the scope of this invention. One type of covalent modification includes reacting targeted amino acid residues of patched-2 with an organic derivatizing agent that is capable of reacting with selected side chains or the N- or C-terminal residues of the patched-2.

Derivatization with bifunctional agents is useful, for instance, for crosslinking patched-2 to a water-insoluble support matrix or surface for use in the method for purifying anti-patched-2 antibodies, and vice-versa. Commonly used crosslinking agents include, e.g., 1,1-bis(diazo-acetyl)-2-phenylethane, glutaraldehyde, N-hydroxy-succinimide esters, for example, esters with 4-azido-salicylic acid, homo-bifunctional imidoesters, including disuccinimidyl esters such as 3,3'-dithiobis-(succinimidyl-propionate), bifunctional maleimides such as bis-N-maleimido-1,8-octane and agents such as methyl-3-[(p-azidophenyl)-dithio]proprioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the $\alpha$-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of patched-2 comprises linking the patched-2 polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337. Such modifications would be expected in increase the half-life of the molecules in circulation in a mammalian system; Extended half-life of patched-2 molecules might be useful under certain circumstances, such as where the patched-2 variant is administered as a therapeutic agent.

The patched-2 of the present invention may also be modified in a way to form a chimeric molecule comprising patched-2 bonded to another, heterologous polypeptide or amino acid sequence. In one embodiment, such a chimeric molecule comprises a fusion of patched-2 with a tag polypeptide, which provides an epitope to which an anti-tag antibody can selectively bind. The epitope tag is generally placed at the amino- or carboxyl-terminus of the patched-2. The presence of such epitope-tagged forms of the patched-2 can be detected using an antibody against the tag polypeptide. Also, provision of the epitope tag enables the patched-2 to be readily purified by affinity purification using an anti-tag antibody or another type of affinity matrix that binds to the epitope tag. In an alternative embodiment, the chimeric molecule may comprise a fusion of the patched-2 with an immunoglobulin or a particular region of an immunoglobulin. For a bivalent form of the chimeric molecule, such a fusion could be to the Fc region of an IgG molecule. Ordinarily, the C-terminus of a contiguous amino acid sequence of a patched-2 receptor is fused to the N-terminus of a contiguous amino acid sequence of an immunoglobulin constant region, in place of the variable region(s), however N-terminal fusions are also possible.

Typically, such fusions retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, immunoadhesins may be synthesized according to known methods.

The precise site at which the fusion is made is not critical; particular sites are well known and may be selected in order to optimize the biological activity, secretion or binding characteristics of the immunoadhesins.

In a preferred embodiment, the C-terminus of a contiguous amino acid sequence which comprises the binding site(s) of patched-2, at the N-terminal end, to the C-terminal portion of an antibody (in particular the Fc domain), containing the effector functions of an immunoglobulin, e.g. immunoglobulin $G_1$ (IgG-1). As herein above mentioned, it is possible to fuse the entire heavy chain constant region to the sequence containing the binding site(s). However, more preferably, a sequence beginning in the hinge region just upstream of the papain cleavage site (which defines IgG Fc chemically; residue 216, taking the first residue of heavy chain constant region to be 114 [Kobat et al., supra], or analogous sites of other immunoglobulins) is used in the fusion. Although it was earlier thought that in immunoadhesins the immunoglobulin light chain would be required for efficient secretion of the heterologous protein-heavy chain fusion proteins, it has been found that even the immunoadhesins containing the whole IgG1 heavy chain are efficiently secreted in the absence of light chain. Since the light chain is unnecessary, the immunoglobulin heavy chain constant domain sequence used in the construction of the immunoadhesins of the present invention may be devoid of a light chain binding site. This can be achieved by removing or sufficiently altering immunoglobulin heavy chain sequence elements to which the light chain is ordinarily linked so that such binding is no longer possible. Thus, the CH1 domain can be entirely removed in certain embodiments of the patched-2/immunoglobulin chimeras.

In a particularly preferred embodiment, the amino acid sequence containing the extracellular domain(s) of patched-2 is fused to the hinge region and CH2, CH3; or CH1, hinge, CH2 and CH3 domains of an IgG-1, IgG-2, IgG-3, or IgG-4 heavy chain.

In some embodiments, the patched-2/immunoglobulin molecules (immunoadhesins) are assembled as monomers, dimers or multimers, and particularly as dimers or tetramers. Generally, these assembled immunoadhesins will have known unit structures similar to those of the corresponding immunoglobulins. A basic four chain structural unit (a dimer of two immunoglobulin heavy chain-light chain pairs) is the form in which IgG, IgA and IgE exist. A four chain unit is repeated in the high molecular weight immunoglobulins; IgM generally exists as a pentamer of basic four-chain units held together by disulfide bonds. IgA globulin, and occasionally IgG globulin, may also exist in a multimeric form in serum. In the case of multimers, each four chain unit may be the same or different.

It is not necessary that the entire immunoglobulin portion of the patched-2/immunoglobulin chimeras be from the same immunoglobulin. Various portions of different immunoglobulins may be combined, and variants and derivatives of native immunoglobulins can be made as herein above described with respect to patched-2, in order to optimize the properties of the immunoadhesin molecules. For example, immunoadhesin constructs in which the hinge of IgG-1 was replaced with that of IgG-3 were found to be functional and showed pharmacokinetics comparable to those of immunoadhesins comprising the entire IgG-1 heavy chain.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8: 2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)]. A preferred tag is the influenza HA tag.

D. Preparation of Patched-2

The description below relates primarily to production of a particular patched-2 by culturing cells transformed or transfected with a vector containing patched-2 nucleic acid. It is, of course, contemplated that alternative methods, which are well known in the art, may be employed to prepare patched-2. For instance, the patched-2 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the vertebrate patched-2 may be chemically synthesized separately and combined using chemical or enzymatic methods to produce the full-length patched-2.

1. Isolation of DNA Encoding Vertebrate Patched-2

DNA encoding patched-2 may be obtained from a cDNA library prepared from tissue believed to possess the patched-2 mRNA and to express it at a detectable level. Accordingly, human patched-2 DNA can be conveniently obtained from a cDNA library prepared from human tissue, such as described in the Examples. The vertebrate patched-2-encoding gene may also be obtained from a genomic library or by oligonucleotide synthesis.

Libraries can be screened with probes (such as antibodies to the patched-2 or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding vertebrate patched-2 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as BLAST, BLAST-2, ALIGN, DNAstar, and INHERIT which employ various algorithms to measure homology.

Nucleic acid having protein coding sequence may be obtained by screening selected cDNA or genomic. libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for patched-2 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology* 52:456–457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for vertebrate patched-2-encoding vectors. *Saccharomyces cerevisiae* is a commonly used lower eukaryotic host microorganism.

Suitable host cells for the expression of vertebrate patched-2 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.* 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding patched-2 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques, which are known to the skilled artisan.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. A preferred replicable expression vector is the plasmid is pRK5. Holmes et al., *Science*, 253:1278–1280 (1991).

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the patched-2 nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the patched-2 nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)]. Promoters for use in bacterial systems also will contain a Shine-Dalgarno (S.D.) sequence operably linked to the DNA encoding patched-2.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Patched-2 transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Inserting an enhancer sequence into the vector may increase transcription of a DNA encoding the patched-2 by higher eukaryotes. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the patched-2 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding patched-2.

Still other methods, vectors, and host cells suitable for adaptation to the synthesis of patched-2 in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence patched-2 polypeptide or against a synthetic peptide based on the DNA sequences provided herein or against exogenous sequence to DNA and encoding a specific antibody epitope.

5. Purification of Polypeptide

Forms of patched-2 may be recovered from host cell lysates. Since patched-2 is membrane-bound, it can be released from the membrane using a suitable detergent solution (e.g. Triton-X 100) or by enzymatic cleavage. Cells employed in expression of patched-2 can be disrupted by various physical or chemical means, such as freeze-thaw cycling, sonication, mechanical disruption, or cell lysing agents.

It may be desired to purify patched-2 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the patched-2. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular patched-2 produced.

E. Uses for Patched-2

(1) Patched-2 is a Specific Receptor for Desert Hedgehog (Dhh)

The hedgehog (Hh) signaling pathway has been implicated in the formation of embryonic structures in mammals and invertebrates. The multi-pass transmembrane receptor patched, is a negative regulator of the Hh pathway, repressing the serpentine signaling molecule smoothened (Smo). Data have shown that loss of patched leads to deregulation of the Hh pathway leading to formation of aberrant structures in the embryos and carcinoma in the adult.

Applicants' newly identified second human patched gene, termed patched-2 (e.g., Ptch-2, SEQ ID NO:2), has a similar 12 transmembrane domain topology as does patched, and can bind to all the members of the Hh family and can complex with Smo (e.g., SEQ ID NO:17). However, the expression patterns of patched-2 and patched do not overlap. patched-2 is expressed mainly in the developing spermatocytes, which are supported directly by the desert hedgehog producing Sertoli cells, which suggests that patched-2 is a receptor for Desert hedgehog.

In the adult tubule, Sertoli cells, which are unusually large secretory cells, traverse the seminiferous tubule from the basal lamina to the luminal aspect, sending out cytoplasmic protrusions that engulf the germ cells. These contacts are particularly close during spermiogenesis, in which the haploid round spermatids undergo differentiation to produce the highly specialized, motile sperm. Tight junctions between adjacent Sertoli cells compartmentalize the tubule into a basal region, which contains mitotic spermatogonia and early spermtocytes, and an adluminal compartment, which contains meiotic spermatocytes and maturing spermatids. In fact, a Sertoli-derived cell line supports the meiotic progression of germ cells in culture, consistent with the view that factors derived from Sertoli cells contribute to germ cell maturation, Rassoulzadegan, M., et al., *Cell* 1993, 75: 997–1006. Loss of Dhh activity results in a recessive, sex-specific phentotype. Female mice homozygous for the mutation were fully viable and fertile, whereas male mice were viable but infertile. A gross examination indicated that, as early as 18.5 dpc, the testes of mutant males were noticeably smaller than those of heterozygous littermates. Bitgood et al., *Curr. Biol.*, 1996 6(3): 298–304. Thus, Sertoli cells likely independently regulate mitotic and meiotic stages of germ cell development during postnatal development. Therefore, since patched-2 appears to be the receptor Dhh (SEQ ID NO:13), molecules which modulate the binding of Dhh (SEQ ID NO:13) to patched-2 would affect the activation of Dhh signaling, and thereby would have utility in the treatment of conditions which are modulated by Dhh (SEQ ID NO:13). For example, testicular cancer). Alternatively, it is also provided that antagonists or agonists of patched-2 may be used for treating disorders or creating a desirable physiological condition effected by blocking Dhh signaling. (E.g, contraception, infertility treatment).

(2) General Uses for Patched-2

Nucleotide sequences (or their complement) encoding patched-2 have various applications in the art of molecular biology, including uses as hybridization probes, in chromosome and gene mapping and in the generation of anti-sense RNA and DNA. Patched-2 nucleic acid will also be useful for the preparation of patched-2 polypeptides by the recombinant techniques described herein.

The full-length native sequence patched-2 gene, or portions thereof, may be used as hybridization probes for a cDNA library to isolate the full-length gene or to isolate still other genes (for instance, those encoding naturally-occurring variants of patched-2) which have a desired sequence identity to the patched-2 sequence disclosed in FIG. 1 (SEQ ID NO:1). Optionally, the length of the probes will be about 20 to about 50 bases. The hybridization probes may be derived from the nucleotide sequence of FIG. 1 (SEQ ID NO:1) or from genomic sequences including promoters, enhancer elements and introns of native sequence patched-2. By way of example, a screening method will comprise isolating the coding region of the patched-2 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the patched-2 gene of the present invention can be used to screen libraries of human cDNA, genomic DNA or mRNA to determine to which members of such libraries the probe hybridizes. Hybridization techniques are described in further detail in the Examples below.

The probes may also be employed in PCR techniques to generate a pool of sequences for identification of closely related patched-2 sequences.

Nucleotide sequences encoding patched-2 can also be used to construct hybridization probes for mapping the gene, which encodes patched-2 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Patched-2 polypeptides can be used in assays to identify the other proteins or molecules involved in complexing with patched-2 which ultimately results in the modulation of hedgehog signaling. Alternatively, these molecules can modulate the binding of patched-2 to Dhh (SEQ ID NO:13). By such methods, inhibitors of the binding interaction can be identified. Proteins involved in such binding interactions can also be used to screen for peptide or small molecule inhibitors or agonists of the binding interaction. Also, the substrate of patched-2 can be used to isolate correlative complexing proteins. Screening assays can be designed to find lead compounds that mimic the biological activity of a native patched-2 or to find those that act as a substrate for patched-2. Such screening assays will include assays amenable to high-throughput screening of chemical libraries, making them particularly suitable for identifying small molecule drug candidates. Such small molecule inhibitors could block the enzymatic action of patched-2, and thereby inhibit hedgehog signaling. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode patched-2 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, was introduced into the animal or an ancestor of the animal at a prenatal, e.g., an embryonic stage. A transgene is a DNA sequence that is integrated into the genome of a cell from which a transgenic animal develops. In one embodiment, cDNA encoding patched-2 can be used to clone genomic DNA encoding patched-2 in accordance with established techniques and the genomic sequences used to generate transgenic animals that contain cells which express DNA encoding patched-2. Methods for generating transgenic animals, particularly animals such as mice or rats, have become conventional in the art and are described, for example, in U.S. Pat. Nos. 4,736,866 and 4,870,009. Typically, particular cells would be targeted for patched-2 transgene incorporation with tissue-specific enhancers. Transgenic animals that include a copy of a transgene encoding patched-2 introduced into the germ line of the animal at an embryonic stage can be used to examine the effect of increased expression of DNA encoding patched-2. Such animals can be used as tester animals for reagents thought to confer protection from, for example, pathological conditions associated with its overexpression.

Non-human homologues of vertebrate patched-2 can be used to construct a patched-2 "knock out" animal which has a defective or altered gene encoding patched-2 as a result of homologous recombination between the endogenous gene encoding patched-2 and altered genomic DNA encoding patched-2 introduced into an embryonic cell of the animal. For example, cDNA encoding patched-2 can be used to clone genomic DNA encoding patched-2 in accordance with established techniques. A portion of the genomic DNA encoding patched-2 can be deleted or replaced with another gene, such as a gene encoding a selectable marker that can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the patched-2 polypeptide.

Suppression or inhibition (antagonism) of Dhh signaling is also an objective of therapeutic strategies. Since patched-2 can combine with all members of the hedgehog family (i.e., Shh, Dhh, Ihh), antagonist molecules which prevent the binding of hedgehog molecules to ptch-2 (SEQ ID NO:2) have therapeutic utility. For example, SHh signaling is known to be activated in Basal Cell Carcinoma; Dhh (SEQ ID NO:13) is known to be involved in the regulation of spermatogenesis. Inhibitor or antagonist of Hh signaling would be effective therapeutics in the treatment of Basal Cell Carcinoma or male contraception, respectively.

The stimulation of Dhh signaling (agonism) is also an objective of therapeutic strategies. Since Ptch-2 (SEQ ID NO:2) also binds to the other members of the Hh family, Ihh and Shh, activating Dhh signaling would be useful in disease states or disorders characterized by inactive or insufficient Hh signaling. For example, degenerative disorders of the nervous system, e.g., Parkinson's disease, memory deficits, Alzheimer's disease, Lou Gehrig's disease, Huntington's disease, schizophrenia, stroke and drug addiction. Additionally, patched-2 agonists could be used to treat gut diseases, bone diseases, skin diseases, diseases of the testis (including infertility), ulcers, lung diseases, diseases of the pancreas, diabetes, osteoporosis.

F. Anti-patched-2 Antibodies

The present invention further provides anti-vertebrate patched-2 antibodies. Exemplary antibodies include polyclonal, monoclonal, humanized, bispecific, and heteroconjugate antibodies.

1. Polyclonal Antibodies

The anti-patched-2 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the patched-2 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-patched-2 antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the patched-2 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against patched-2. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide.

Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized Antibodies

The anti-patched-2 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)].

4. Bispecific Antibodies

Bispecific antibodies are monoclonal, preferably human or humanized, antibodies that have binding specificities for at least two different antigens. In the present case, one of the binding specificities is for the vertebrate patched-2, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for Anti-patched-2 Antibodies

The anti-patched-2 antibodies of the invention have various utilities. For example, anti-patched-2 antibodies may be used in diagnostic assays for patched-2, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144: 945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-patched-2 antibodies also are useful for the affinity purification of patched-2 from recombinant cell culture or natural sources. In this process, the antibodies against patched-2 are immobilized on a suitable support, such a Sephadex resin or filter paper, using methods well known in the art. The immobilized antibody then is contacted with a sample containing the patched-2 to be purified, and thereafter the support is washed with a suitable solvent that will remove substantially all the material in the sample except the patched-2, which is bound to the immobilized antibody. Finally, the support is washed with another suitable solvent that will release the patched-2 from the antibody.

Figure 9:
FIG. 9 is an in situ hybridization which demonstrates the accumulation of Ptch (SEQ ID NO:4) and Ptch-2 (SEQ ID NO:2) mRNA detected by in situ hybridization in basal cells of E18 transgenic mice overexpressing SMO-M2 (SEQ ID NO:16) (Xie et al., Nature 391: 90–92 (1998).

Basal cell carcinoma (BCC) is the most common human cancer. The Hh signaling pathway was found to be activated in all BCCs. Loss of patched function is thought to lead to unregulated Smo activity and is responsible for about half of all BCCs. Patched being a target of the Hh pathway itself, increases in patched mRNA levels have been detected in BCC [Gailani, et al., *Nature Genet.* 14: 78–81 (1996)] as well as in animal models of BCC. Oro et al., *Science* 276: 817–821 (1997); Xie et al., *Nature* 391: 90–92 (1998). Abnormal activation of Sh signaling as that which occurs in BCC, was examined to confirm whether patched-2 expression was increased. As shown in FIG. 9, an in situ hybridization for Ptch (SEQ ID NO:4) and Ptch-2 (SEQ ID NO:2) in Smo-M2 (SEQ ID NO:16) transgenic mice (Xie et al., supra), while low than Ptch (SEQ ID NO:4), was still high in tumor cells. This suggests that therapeutic antibodies directed toward Ptch-2 (SEQ ID NO:2) may be useful for the treatment of BCC.

Anti-patched-2 antibodies also have utilities similar to those articulated for under the previous section "E. Uses of Patched-2". Depending on whether anti-patched-2 antibodies will bind patched-2 receptors so as to either inhibit Hh signaling (antagonist) or inhibit patched-2 complexing with Smo (SEQ ID NO:17) and thereby remove the normal inhibitory effect of Smo (SEQ ID NO:17) on Hh signaling (agonist) the antibody will have utilities corresponding to those articulated previously for patched-2.

H. Patched-2 Antagonists

Several approaches may be suitably employed to create the patched-2 antagonist and agonist compounds of the present invention. Any approach where the antagonist molecule can be targeted to the interior of the cell, which interferes or prevents wild type patched-2 from normal operation is suitable. For example, competitive inhibitors, including mutant patched-2 receptors which prevent wild type patched-2 from properly binding with other proteins necessary for Dhh and Hh signaling. Additional properties of such antagonist or agonist molecules are readily determinable by one of ordinary skill, such as size, charge and hydrophobicity suitable for transmembrane transport.

Where mimics or other mammalian homologues of patched-2 are to be identified or evaluated, the cells are exposed to the test compound and compared to positive controls which are exposed only to human patched-2, and to negative controls which were not exposed to either the compound or the natural ligand. Where antagonists or agonists of patched-2 signal modulation are to be identified or evaluated, the cells are exposed to the compound of the invention in the presence of the natural ligand and compared to controls which are not exposed to the test compound.

Detection assays may by employed as a primary screen to evaluate the Hh signaling inhibition/enhancing activity of the antagonist/agonist compounds of the invention. The assays may also be used to assess the relative potency of a compound by testing a range of concentrations, in a range from 100 mM to 1 pM, for example, and computing the concentration at which the amount of phosphorylation or signal transduction is reduced or increased by 50% ($IC_{50}$) compared to controls.

Assays can be performed to identify compounds that affect Hh signaling of patched-2 substrates. Specifically, assays can be performed to identify compounds that increase the phosphorylation activity of patched-2 or assays can be performed to identify compounds that decrease the Hh signaling of patched-2 substrates. These assays can be performed either on whole cells themselves or on cell extracts. The assays can be performed in a variety of formats, including protein-protein binding assays, biochemical screening assays, immunoassays, cell based assays, etc. Such assay formats are well known in the art.

The screening assays of the present invention are amenable to high-throughput screening of chemical libraries, and are particularly suitable for identifying small molecule drug candidates.

(1) Antagonist and Agonist Molecules

To screen for antagonists and/or agonists of patched-2 signaling, the assay mixture is incubated under conditions whereby, but for the presence of the candidate pharmacological agent, patched-2 induces hedgehog signaling with a reference activity. The mixture components can be added in any order that provides for the requisite hedgehog activity. Incubation may be performed at any temperature that facilitates optimal binding, typically between about 4° and 40° C., more commonly between about 15° and 40° C. Incubation periods are likewise selected for optimal binding but also minimized to facilitate rapid, high-throughput screening, and are typically between about 0.1 and 10 hours, preferably less than 5 hours, more preferably less than 2 hours. After incubation, the effect of the candidate pharmacological agent on the patched-2 signaling is determined in any convenient way. For cell-free binding-type assays, a separation step is often used to separate bound and unbound components. Separation may, for example, be effected by precipitation (e.g. TCA precipitation, immunoprecipitation, etc.), immobilization (e.g. on a solid substrate), followed by washing. The bound protein is conveniently detected by taking advantage of a detectable label attached to it, e.g. by measuring radioactive emission, optical or electron density, or by indirect detection using, e.g. antibody conjugates.

For example, a method of screening for suitable patched-2 antagonists and/or agonists could involve the application of Dhh and other hedgehog ligands. Such a screening assay could compare in situ hybridization in the presence and absence of the candidate antagonist and/or agonist in a patched-2 expressing tissue as well as confirmation or absence of patched-2 modulated cellular development. Typically these methods involve exposing an immobilized patched-2 to a molecule suspected of binding thereto and determining the level of ligand binding downstream activation of reporter constructs and/or evaluating whether or not the molecule activates (or blocks activation of) patched-2. In order to identify such patched-2 binding ligands, patched-2 can be expressed on the surface of a cell and used to screen libraries of synthetic candidate compounds or naturally-occurring compounds (e.g., from endogenous sources such as serum or cells).

Suitable molecules that affect the protein-protein interaction of patched-2 and its binding proteins include fragments of the latter or small molecules, e.g., peptidomimetics, which will inhibit ligand-receptor interaction. Such small molecules, which are usually less than 10 K molecular weight, are preferable as therapeutics since they are more likely to be permeable to cells, are less susceptible to degradation by various cellular mechanisms, and are not as apt to elicit an immune response as proteins. Small molecules include but are not limited to synthetic organic or inorganic compounds. Many pharmaceutical companies have extensive libraries of such molecules, which can be conveniently screened by using the assays of the present invention. Non-limiting examples include proteins, peptides, glycoproteins, glycopeptides, glycolipids, polysaccharides, oligosacchardies, nucleic acids, bioorganic molecules, peptidomimetics, pharmacological agents and their metabolites, transcriptional and translation control sequences, and the like.

A preferred technique for identifying molecules which bind to patched-2 utilizes a chimeric substrate (e.g., epitope-tagged patched-2 or patched-2 immunoadhesin) attached to a solid phase, such as the well of an assay plate. The binding of the candidate molecules, which are optionally labeled (e.g., radiolabeled), to the immobilized receptor can be measured. Alternatively, competition for various Hh pathways, especially Dhh (SEQ ID NO:13) can be measured. In screening for antagonists and/or agonists, patched-2 can be exposed to a patched-2 substrate followed by the putative antagonist and/or agonist, or the patched-2 binding protein and antagonist and/or agonist can be added simultaneously, and the ability of the antagonist and/or agonist to block patched-2 activation can be evaluated.

(2) Detection Assays

The patched-2 polypeptides are useful in assays for identifying lead compounds for therapeutically active agents that modulate patched-2 receptor/ligand hedgehog signaling. Specifically, lead compounds that either prevent the formation of patched-2 signaling complexes or prevent or attenuate patched-2 modulated hedgehog signaling (e.g, binding to patched-2) can be conveniently identified.

Various procedures known in the art may be used for identifying, evaluating or assaying the inhibition of activity of the patched-2 proteins of the invention. As patched-2 is believed to be a receptor for Dhh (SEQ ID NO:13), but also binds Shh (SEQ ID NO:14) and Ihh (SEQ ID NO:29), techniques known for use with identifying ligand/receptor modulators may also be employed with the present invention. In general, such assays involve exposing target cells in culture to the compounds and a) biochemically analyzing cell lysates to assess the level and/or identity of binding; or (b) scoring phenotypic or functional changes in treated cells as compared to control cells that were not exposed to the test substance. Such screening assays are described in U.S. Pat. No. 5,602,171, U.S. Pat. No. 5,710,173, WO 96/35124 and WO 96/40276.

(a) Biochemical Detection Techniques

Biochemical analysis can be evaluated by a variety of techniques. One typical assay mixture which can be used with the present invention contains patched-2 and a ligand protein with which patched-2 is normally associated (e.g., Dhh (SEQ ID NO:13)) usually in an isolated, partially pure or pure form. One or both of these components may be patched-2 to another peptide or polypeptide, which may, for example, provide or enhance protein-protein binding, improve stability under assay conditions, etc. In addition, one of the components usually comprises or is coupled to a detectable label. The label may provide for direct detection by measuring radioactivity, luminescence, optical or electron density, etc., or indirect detection such as an epitope tag, an enzyme, etc. The assay mixture can additionally comprise a candidate pharmacological agent, and optionally a variety of other components, such as salts, buffers, carrier proteins, e.g. albumin, detergents, protease inhibitors, nuclease inhibitors, antimicrobial agents, etc., which facilitate binding, increase stability, reduce non-specific or background interactions, or otherwise improve the efficiency or sensitivity of the assay.

The following detection methods may also be used in a cell-free system wherein cell lysate containing the signal transducing substrate molecule and patched-2 is mixed with a compound of the invention. To assess the activity of the compound, the reaction mixture may be analyzed by the SDS-PAGE technique or it may be added to substrate-specific anchoring antibody bound to a solid support, and a detection procedure as described above is performed on the separated or captured substrate to assess the presence or absence of a patched-2 binding ligand. The results are compared to those obtained with reaction mixtures to which the compound is not added. The cell-free system does not require the natural ligand or knowledge of its identity. For example, Posner et al. (U.S. Pat. No. 5,155,031 describes the use of insulin receptor as a substrate and rat adipocytes as target cells to demonstrate the ability of pervanadate to inhibit PTP activity. Another example, Burke et al., *Biochem. Biophys. Res. Comm.* 204: 129–134 (1994) describes the use of autophosphorylated insulin receptor and recombinant PTP1B in assessing the inhibitory activity of a phosphotyrosyl mimetic.

(i) Whole Cell Detection

A common technique involves incubating cells with patched-2 and radiolabeled ligand, lysing the cells, separating cellular protein components of the lysate using an SDS-polyacrylamide gel (SDS-PAGE) technique, in either one or two dimensions, and detecting the presence of labeled proteins by exposing X-ray film. Detection can also be effected without using radioactive labeling. In such a technique, the protein components (e.g., separated by SDS-PAGE) are transferred to a nitrocellulose membrane where the presence of patched-ligand complexes is detected using an anti-ligand antibody.

Alternatively, the anti-patched-2 ligand antibody can be conjugated with an enzyme, such as horseradish peroxidase, and detected by subsequent addition of a colorimetric substrate for the enzyme. A further alternative involves detecting the anti-patched-2 ligand by reacting with a second antibody that recognizes anti-patched-2 ligand, this second antibody being labeled with either a radioactive moiety or an enzyme as previously described. Examples of these and similar techniques are described in Hansen et al., *Electrophoresis* 14: 112–126 (1993); Campbell et al., *J. Biol. Chem.* 268: 7427–7434 (1993); Donato et al., *Cell Growth Diff.* 3: 258–268 (1992); Katagiri et al., *J. Immunol.* 150: 585–593

(1993). Additionally, the anti-patched-2 ligand can be detected by labeling it with a radioactive substance, followed by scanning the labeled nitrocellulose to detect radioactivity or exposure of X-ray film.

Further detection methods may be developed which are preferred to those described above. Especially for use in connection with high-throughput screening, it is expected that such methods would exhibit good sensitivity and specificity, extended linear range, low background signal, minimal fluctuation, compatibility with other reagents, and compatibility with automated handling systems.

The in vivo efficacy of the treatment of the present invention can be studied against chemically induced tumors in various rodent models. Tumor cell lines propagated in in vitro cell cultures can be introduced in experimental rodents, e.g. mice by injection, for example by the subcutaneous route. Techniques for chemical inducement of tumors in experimental animals are well known in the art.

(ii) Kinase Assays

Because patched-2 is a negative regulator of Hh signaling, which when activated by Hh releases the normal inhibitory effect on Smo, the inhibition of patched-2 binding to Smo can be measured by activation of various kinase substrate associated with Hh signaling. When the screening methods of the present invention for patched-2 antagonists/agonists are carried out as an ex vivo assay, the target kinase (e.g. fused) can be a substantially purified polypeptide. The kinase substrate (e.g., MBP, Gli) is a substantially purified substrate, which in the assay is phosphorylated in a reaction with a substantially purified phosphate source that is catalyzed by the kinase. The extent of phosphorylation is determined by measuring the amount of substrate phosphorylated in the reaction. A variety of possible substrates may be used, including the kinase itself in which instance the phosphorylation reaction measured in the assay is autophosphorylation. Exogenous substrates may also be used, including standard protein substrates such as myelin basic protein (MBP); yeast protein substrates; synthetic peptide substrates, and polymer substrates. Of these, MBP and other standard protein substrates may be regarded as preferred. Other substrates may be identified, however, which are superior by way of affinity for the kinase, minimal perturbation of reaction kinetics, possession of single or homogenous reaction sites, ease of handling and post-reaction recover, potential for strong signal generation, and resistance or inertness to test compounds.

Measurement of the amount of substrate phosphorylated in the ex vivo assay of the invention may be carried out by means of immunoassay, radioassay or other well-known methods. In an immunoassay measurement, an antibody (such as a goat or mouse anti-phosphoserine/threonine antibody) may be used which is specific for phosphorylated moieties formed during the reaction. Using well-known ELISA techniques, the phosphoserine/threonine antibody complex would itself be detected by a further antibody linked to a label capable of developing a measurable signal (as for example a fluorescent or radioactive label). Additionally, ELISA-type assays in microtitre plates may be used to test purified substrates. Peraldi et al., *J. Biochem.* 285: 71–78 (1992); Schraag et al., *Anal. Biochem.* 211: 233–239 (1993); Cleavland, *Anal. Biochem.* 190: 249–253 (1990); Farley, *Anal. Biochem.* 203: 151–157 (1992) and Lozaro, *Anal. Biochem.* 192: 257–261 (1991).

For example, detection schemes can measure substrate depletion during the kinase reaction. Initially, the phosphate source may be radiolabeled with an isotope such as $^{32}P$ or $^{33}P$, and the amount of substrate phosphorylation may be measured by determining the amount of radiolabel incorporated into the substrate during the reaction. Detection may be accomplished by: (a) commercially available scintillant-containing plates and beads using a beta-counter, after adsorption to a filter or a microtitre well surface, or (b) photometric means after binding to a scintillation proximity assay bead or scintillant plate. Weernink and Kijken, *J. Biochem. Biophs. Methods* 31: 49, 1996; Braunwalder et al., *Anal. Biochem.* 234: 23 (1996); Kentrup et al., *J. Biol. Chem.* 271:.3488 (1996) and Rusken et al., *Meth. Enzymol.* 200: 98 (1991).

Preferably, the substrate is attached to a solid support surface by means of non-specific or, preferably, specific binding. Such attachment permits separation of the phosphorylated substrate from unincorporated, labeled phosphate source (such as adenosine triphosphate prior to signal detection. In one embodiment, the substrate may be physically immobilized prior to reaction, as through the use of Nunc™ high protein binding plate (Hanke et al., *J. Biol. Chem.* 271: 695 (1996)) or Wallac ScintiStrip™ plates (Braunwalder et al., *Anal. Biochem.* 234: 23 (1996). Substrate may also be immobilized after reaction by capture on, for example, P81 phophocellulose (for basic peptides), PEI/acidic molybdate resin or DEAE, or TCA precipitation onto Whatman™ 3MM paper, Tiganis et al., *Arch. Biochem. Biophys.* 325: 289 (1996); Morawetz et al., *Mol. Gen. Genet.* 250; 17 (1996); Budde et al., *Int J. Pharmacognosy* 33: 27 (1995) and Casnellie, *Meth. Enz.* 200: 115 (1991). Yet another possibility is the attachment of the substrate to the support surface, as by conjugation with binding partners such as glutathione and streptavidin (in the case of GST and biotin), respectively) which have been attached to the support, or via antibodies specific for the tags which are likewise attached to the support.

Further detection methods may be developed which are preferred to those described above. Especially for use in connection with high-throughput screening, it is expected that such methods would exhibit good sensitivity and specificity, extended linear range, low background signal, minimal fluctuation, compatibility with other reagents, and compatibility with automated handling systems.

The in vivo efficacy of the treatment of the present invention can be studied against chemically induced tumors in various rodent models. Tumor cell lines propagated in in vitro cell cultures can be introduced in experimental rodents, e.g. mice by injection, for example by the subcutaneous route. Techniques for chemical inducement of tumors in experimental animals are well known in the art.

(b) Biological Detection Techniques:

The ability of the antagonist/agonist compounds of the invention to modulate the activity of patched-2, which itself modulates hedgehog signaling, may also be measured by scoring for morphological or functional changes associated with ligand binding. Any qualitative or quantitative technique known in the art may be applied for observing and measuring cellular processes which comes under the control of patched-2. The activity of the compounds of the invention can also be assessed in animals using experimental models of disorders caused by or related to dysfunctional hedgehog signaling. For example, ineffective Dhh hedgehog signaling in mice leads to viable but sterile mice. Additionally, proper Shh signaling is critical to murine embryonic development at the notochord and floor plate, neural tube, distal limb structures, spinal column and ribs. Improper Shh signaling, is also correlative with cyclopia. Any of these phenotypic properties could be evaluated and quantified in a screening assay for patched-2 antagonists and/or agonist. Disease states associated with overexpression of hedgehog is associated with basal cell carcinoma while inactive Shh signaling leads to improper neural development.

The data obtained from these cell culture assays and animal studies can be used in formulating a range of dosages for use in humans. The dosage of the compounds of the invention should lie within a range of circulating concentrations with little or no toxicity. The dosage may vary within this range depending on the dosage form employed and the route of administration.

(2) Antisense Oligonucleotides

Another preferred class of antagonists involves the use of gene therapy techniques, include the administration of antisense oligonucleotides. Applicable gene therapy techniques include single or multiple administrations of therapeutically effective DNA or mRNA. Antisense RNAs and DNAs can be used as therapeutic agents for blocking the expression of certain genes in vivo. Reference short antisense oligonucleotides can be imported into cells where they act as inhibitors, despite their low intracellular concentrations caused by restricted uptake by the cell membrane, Zamecnik et al., *Proc. Natl. Acad. Sci. USA* 83: 4143–4146 (1986). The anti-sense oligonucleotides can be modified to enhance their uptake, e.g., by substituting their negatively charged phophodiester groups by uncharged groups.

There are a variety of techniques known for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection, Dzau et al., *Trends Biotech*. 11: 205–210 (1993). In some situations it is desirable to provide the nucleic acid source with an agent that targets the cells, such as an antibody specific for a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem*. 262: 44294432 (1987); Wagner et al., *Proc. Natl. Acad. Sci. USA* 87: 3410–3414 (1990). For a review of known gene targeting and gene therapy protocols, see Anderson et al., *Science* 256: 808–813 (1992).

In one embodiment of the invention, patched-2 expression may be reduced by providing patched-2-expressing cells with an amount of patched-2 antisense RNA or DNA effective to reduce expression of the patched-2 protein.

I. Diagnostic Uses

Another use of the compounds of the invention (e.g., patched-2, patched-2 and anti-patched-2 antibodies) described herein is to help diagnose whether a disorder is driven, to some extent, by patched-2 or hedgehog signaling. For example, basal cell carcinoma cells are associated with active hedgehog signaling, spermatocyte formation is associated with Dhh signaling, and defective patched and patched-2 suppression may be associated with testicular carcinomas.

A diagnostic assay to determine whether a particular disorder is driven by patched-2 modulated hedgehog signaling, can be carried out using the following steps: (1) culturing test cells or tissues; (2) administering a compound which can prevent patched-2 binding with Smo (SEQ ID NO:17), thereby activating the Hh signaling pathway; and (3) measuring the amount of Hh signaling. The steps can be carried out using standard techniques in light of the present disclosure. For example, standard techniques can be used to isolate cells or tissues and culturing or in vivo.

Compounds of varying degree of selectivity are useful for diagnosing the role of patched-2. For example, compounds which inhibit patched-2 in addition to another form of kinase can be used as an initial test compound to determine if one of several signaling ligands drive the disorder. The selective compounds can then be used to further eliminate the possible role of the other ligands in driving the disorder. Test compounds should be more potent in inhibiting ligand-patched-2 binding activity than in exerting a cytotoxic effect (e.g., an $IC_{50}/LD_{50}$ of greater than one). The $IC_{50}$ and $LD_{50}$ can be measured by standard techniques, such as an MTT assay, or by measuring the amount of LDH released. The degree of $IC_{50}/LD_{50}$ of a compound should be taken into account in evaluating the diagnostic assay. For example, the larger the $IC_{50}/LD_{50}$ ratio the more relative the information. Appropriate controls take into account the possible cytotoxic effect of a compound of a compound, such as treating cells not associated with a cell proliferative disorder (e.g., control cells) with a test compound, can also be used as part of the diagnostic assay. The diagnostic methods of the invention involve the screening for agents that modulate the effects of patched-2 upon hedgehog signaling. Exemplary detection techniques include radioactive labeling and immunoprecipitating (U.S. Pat. No. 5,385,915).

J. Pharmaceutical Compositions and Dosages

Therapeutic formulations of the compositions of the invention are prepared for storage as lyophilized formulations or aqueous solutions by mixing the patched-2 molecule, agonist and/or antagonist having the desired degree of purity with optional "pharmaceutically-acceptable" or "physiologically-acceptable" carriers, excipients or stabilizers typically employed in the art (all of which are termed "excipients"). For example, buffering agents, stabilizing agents, preservatives, isotonifiers, non-ionic detergents, antioxidants and other miscellaneous additives. (See Remington's Pharmaceutical Sciences, $16^{th}$ Ed., A. Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives are added to retard microbial growth, and are added in amounts ranging from 0.2%–1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonifiers sometimes known as "stabilizers" are present to ensure isotonicity of liquid compositions of the present invention and include polyhydric sugar alcohols, preferably trihydric or higher sugar alcohols, such as glycerin, erythritol, arabitol, xylitol, sorbitol and mannitol. Polyhydric alcohols can be present in an amount between 0.1% to 25% by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thiocitic acid, sodium thioglycolate, thioglycerol, α-monothioglycerol and sodium thio sulfate; low molecular weight polypeptides (i.e. <10 residues); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccacharides such as raffinose; polysaccharides such as dextran. Stabilizers can be present in the range from 0.1 to 10,000 weights per part of weight active protein.

Non-ionic surfactants or detergents (also known as "wetting agents") are present to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants are present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coascervation techniques or by interfacial polymerization, for example, hydroxymethylcellulose or gelatin-microcapsule and poly (methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences*, 16th edition, A. Osal, Ed. (1980).

The formulations to be used for in vivo administration must be sterile. This is readily accomplished, for example, by filtration through sterile filtration membranes.

Sustained-release preparations may be prepared. Suitable examples of sustained-release preparations include semipermeable matrices of solid hydrophobic polymers containing the compounds of the invention, which matrices are in the form of shaped articles, e.g., films, or microcapsules. Examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated compounds of the invention remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of therapeutic polypeptide, antibody or fragment thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans. However, based on common knowledge of the art, a pharmaceutical composition effective in modulating Dhh and Hh signaling may provide a local patched-2 protein concentration of between about 10 and 1000 ng/ml, preferably between 100 and 800 ng/ml and most preferably between about 200 ng/ml and 600 ng/ml of Ptch-2 (SEQ ID NO:2).

In a preferred embodiment, an aqueous solution of therapeutic polypeptide, antibody or fragment thereof is administered by subcutaneous injection. Each dose may range from about 0.5 μg to about 50 μg per kilogram of body weight, or more preferably, from about 3 μg to about 30 μg per kilogram body weight.

The dosing schedule for subcutaneous administration may vary from once a week to daily depending on a number of clinical factors, including the type of disease, severity of disease, and the subject's sensitivity to the therapeutic agent.

Patched-2 polypeptide may comprise an amino acid sequence or subsequence thereof as indicated in FIG. 1, active amino acid sequence derived therefrom, or functionally equivalent sequence as this subsequence is believed to comprise the functional portion of the patched-2 polypeptide.

If the subject manifests undesired side effects such as temperature elevation, cold or flu-like symptoms, fatigue, etc., it may be desirable to administer a lower dose at more frequent intervals. One or more additional drugs may be administered in combination with patched-2 to alleviate such undesired side effects, for example, an anti-pyretic, anti-inflammatory or analgesic agent.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Introduction:

At the cell surface, Hh function appears to be mediated by a multicomponent receptor complex involving Ptch and Smo (SEQ ID NO:17), two multi-transmembrane proteins initially identified as segment polarity genes in Drosophila and later characterized in vertebrates. Nakano, Y. et al., *Nature* 341: 508–513 (1989); Goodrich et al., *Gene Dev.* 10: 301–312 (1996); Marigo et al., *Develop.* 122: 1225–1233 (1996); van den Heuvel et al., *Nature* 382: 547–551 (1996); Alcedo et al., *Cell* 86: 221–232 (1996); Stone et al. *Nature* 384: 129–34 (1996). Both genetic and biochemical evidence support the existence of a receptor complex where Ptch (SEQ ID NO:4) is the ligand binding subunit, and where Smo (SEQ ID NO:17), a G-protein coupled receptor-like molecule, is the signaling component. Stone et al., *Nature* 384: 129–134 (1996), Marigo et al., *Nature* 384: 176–79 (1996), Chen et al., *Cell* 87: 553–63 (1996). Upon binding of Hh to Ptch (SEQ ID NO:4), the normal inhibitory effect of Ptch (SEQ ID NO:4) on Smo (SEQ ID NO:17) is relieved, allowing Smo (SEQ ID NO:17) to transduce the Hh signal across the plasma membrane.

Results:

It remains to be established if the PTCH/SMO receptor complex mediates the action of all 3 mammalian Hhs or if specific components exist. Recently, a second murine Patched gene, mPatched-2 (SEQ ID NO:7) was recently isolated [Motoyama et al., *Nature Genet.* 18: 104–106 (1998)] but its function as a Hh receptor has not been established. In order to characterize patched-2 (SEQ ID NO:2)and compare it to Patched (SEQ ID NO:4) with respect to the biological function of the various Hh family members, we have screened EST databases with the Patched (SEQ ID NO:4) protein and identified 2 EST candidates for a novel human patched gene. A full length cDNA encoding human Ptch-2 (SEQ ID NO:2) was cloned from a testis library. The initiation ATG defines a 3612 nucleotide open reading frame encoding a 1204 amino acid long protein with a predicted molecular weight of approximately 131 kDa. The overall identity between human Ptch (SEQ ID NO:4) and Ptch-2 (SEQ ID NO:2) is 54% (FIG. 1), while the identity between human PTCH-2 and the recently described mouse Ptch-2 (SEQ ID NO:7) is 90% (FIG. 8). The most obvious structural difference between the two human Patched proteins is a truncated C-terminal cytoplasmic domain in Ptch-2 (SEQ ID NO:2). In addition, only one of the two glycosylation sites present in Ptch (SEQ ID NO:4) is conserved in Ptch-2 (SEQ ID NO:2).

To determine if Patched-2 is a Hh receptor and if the two Patched molecules are capable of discriminating between the various Hh ligands through specific binding, Applicants transfected human 293 embryonic kidney cells with Ptch (SEQ ID NO:4) or Ptch-2 (SEQ ID NO:2) expression constructs and analyzed the cells for binding of Shh, Dhh and Ihh. As shown on FIG. 7A, binding of $^{125}$I-Shh can be competed with an excess of Shh, Dhh or Ihh (SEQ ID NOS:14, 13 and 29), respectively. Scatchard analysis of the displacement curves indicates that all Hhs have similar affinity for Ptch (SEQ ID NO:4) (Shh, 1.0 nM (SEQ ID NO:29); Dhh, 2.6 nM (SEQ ID NO:13); Ihh, 1.0 nM (SEQ ID NO:14)) and Ptch-2 (SEQ ID NO:2) (Shh, 1.8 nM; Dhh, 0.6 nM (SEQ ID NO:14); Ihh, 0.4 nM (SEQ ID NO:29)) indicating that both Ptch (SEQ ID NO:4) and Ptch-2 (SEQ ID NO:2) can serve as physiological receptors for the 3 mammalian Hh proteins.

Figure 7A:
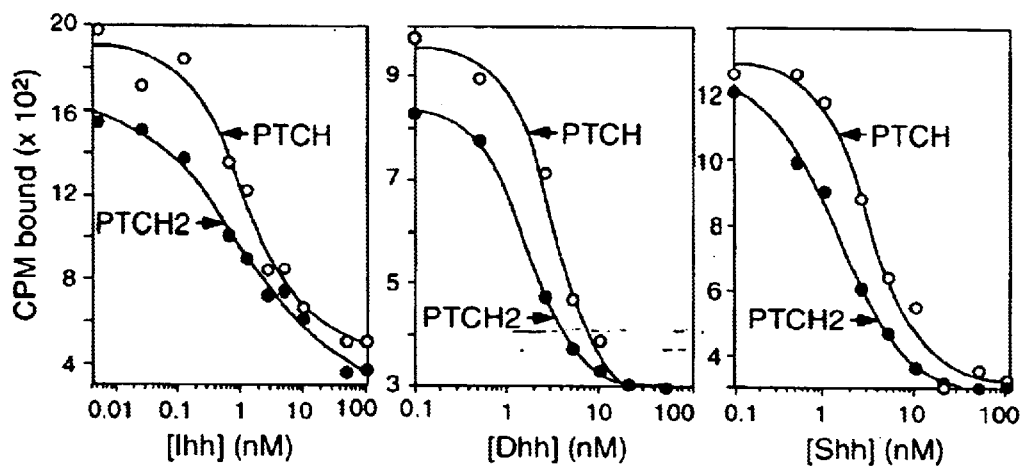
FIG. 7A is logarithmic plot comparing the binding Ptch-2 (SEQ ID NO:2) to Dhh (SEQ ID NO:13) and Shh (SEQ ID NO:14). Competitive binding of recombinant murine $^{125}$I-Shh to 293 cells overexpressing Ptch (SEQ ID NO:4) or Ptch-2 (SEQ ID NO:2). There was no detectable binding to mock transfected cells (data not shown).
Figure 7B:
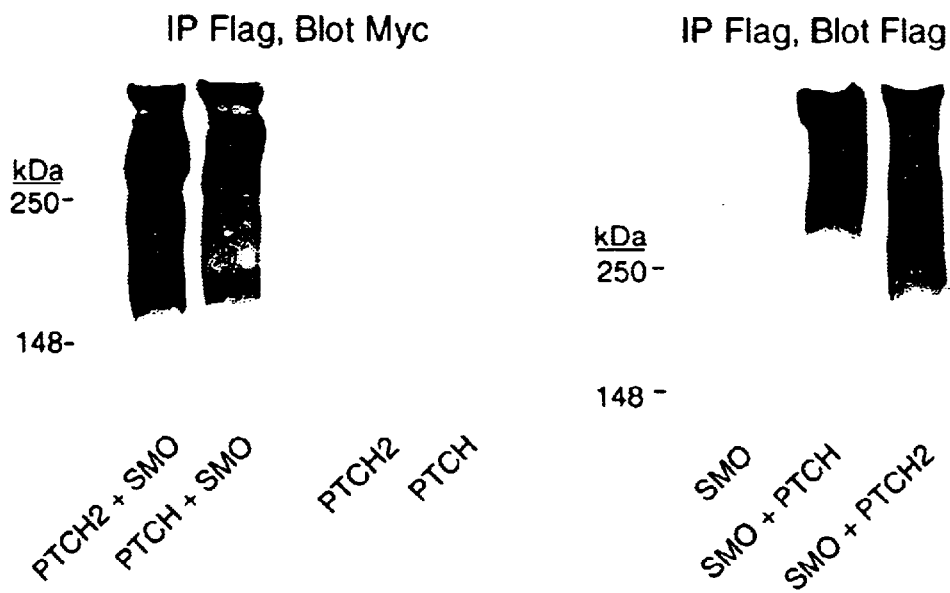
FIG. 7B is a western blot illustrating co-immunoprecipitation of epitope tagged Ptch (SEQ ID NO:4) or Ptch-2 (SEQ ID NO:2) with epitope tagged Smo (SEQ ID NO:15). Immunoprecipitation was performed with antibodies to the Flag tagged Ptch (SEQ ID NO:4) and analyzed on a 6% acrylanide gel with antibodies to the Myc tagged Smo (SEQ ID NO:15). Protein complexes can be detected for both Ptch (SEQ ID NO:4) and Ptch-2 (SEQ ID NO:2) with Smo (SEQ ID NO:15) Ptch (SEQ ID NO:4) and Ptch-2 (SEQ ID NO:2) express at similar levels as shown by immunoprecipitation using antibodies to the Flag-tag and western blot using the same anti-Flag antibody.

Applicants next determined whether, like Patched, Patched-2 forms a physical complex with Smo (SEQ ID NO:17). Expression constructs for Flag-tagged Ptch (SEQ ID NO:4) or Ptch-2 (SEQ ID NO:2) were transiently co-transfected in 293 cells with Myc-tagged Smo (SEQ ID NO:17). As described previously [Stone et al., *Nature* 384: 129–34 (1996)], in cells expressing Ptch (SEQ ID NO:4) and Smo (SEQ ID NO:15), Ptch (SEQ ID NO:4) can be immunoprecipitated with antibodies against the epitope-tagged Smo (SEQ ID NO:15) (FIG. 7B). Similarly, Patched-2 can be immunoprecipitated with antibodies against the epitope-tagged Smo (SEQ ID NO:15) when the two proteins are co-expressed in 293 cells. Together, these results suggest a model where Patched-2 forms a multicomponent Hh receptor complex with Smo (SEQ ID NO:17) similar to the one described for PTCH (Stone et al., supra). Interestingly, these results also demonstrate that the long C-terminal tail which is missing in Patched-2 is not required for the interaction with Smo (SEQ ID NO:17) as was already suggested by the analysis of truncated Patched (Stone et al., supra). However, it remains possible that the absence of a C-terminal domain affects the capacity of Patched-2 to block signaling by Smo (SEQ ID NO:17) or leads to difference in signaling by Patched compared to Patched-2.

Figure 6C:
FIGS. 6A–F is an in situ hybridization comparing Ptch (SEQ ID NO:4), Ptch-2 SEQ ID NO:2 and Fused (FuRK) (SEQ ID NO:10) expression. High magnification of mouse testis showing expression of (a) Ptch SEQ ID NO:4, Ptch-2 (SEQ ID NO:2) (b) and FuRK (SEQ ID NO:10) (c). Low magnification of testis section hybridized with Ptch-2 sense (SEQ ID NO:11) (d) and anti-sense probe (SEQ ID NO:12) (e) respectively.
Figure 6B:
Figure 6A:
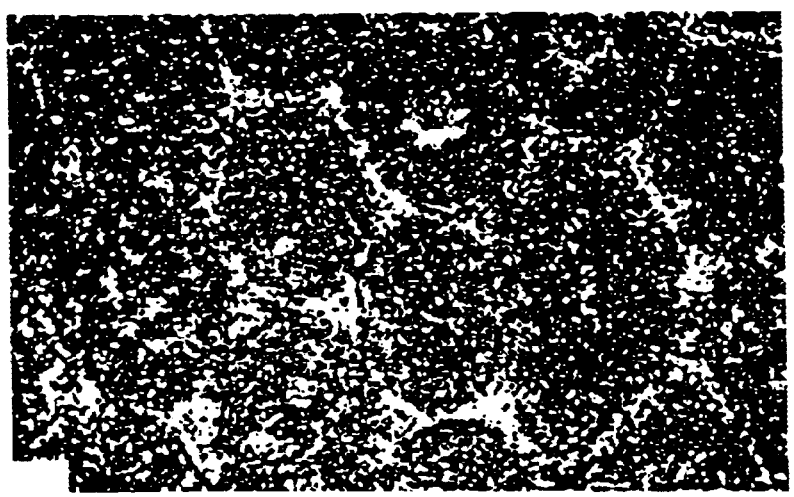
Figure 6F:
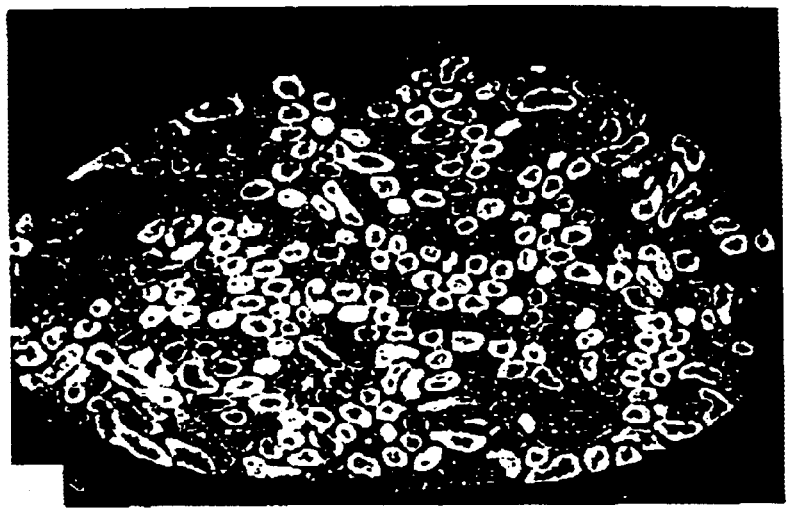
Figure 6E:
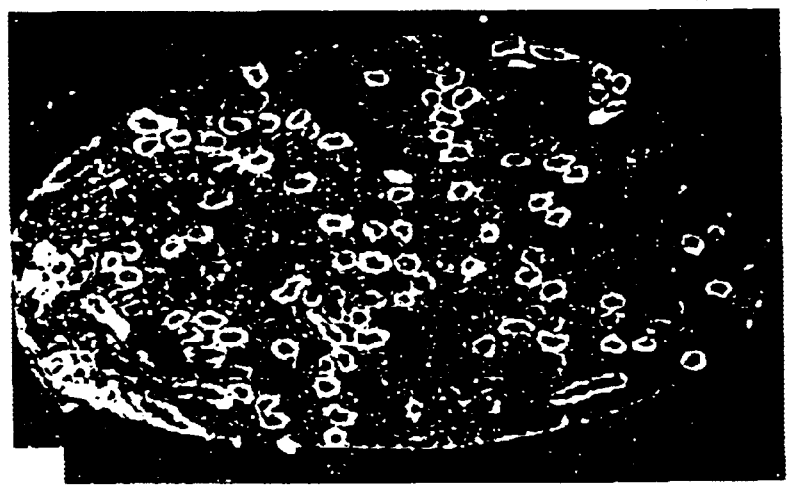
Figure 6D:
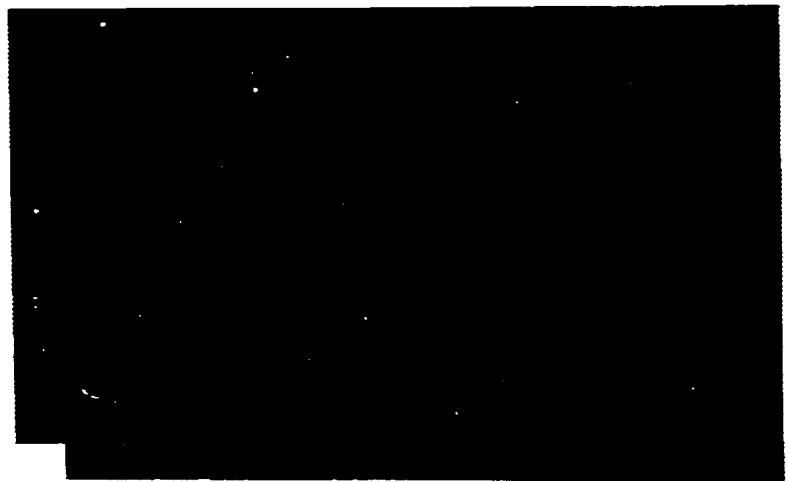

To further investigate whether Patched-2 could mediate the action of a specific Hh molecule based on its expression profile, Applicants have compared the expression pattern of Ptch (SEQ ID NO:4) and Ptch-2 (SEQ ID NO:2). First, Northern blot analysis using a probe specific for Ptch-2 (SEQ ID NO:1) revealed high levels of PTCH2 mRNA in the testis (FIG. 4). By this method, Ptch-2 (SEQ ID NO:1) expression was not detected in any other tissue analyzed including embryonic tissues (data not shown). This profile is very different from the one observed for Ptch (SEQ ID NO:18) which was not found in testis by Northern blot but in a large number of adult and embryonic tissues [Goodrich et al., *Genes Dev.* 10: 301–312 (1996)]. More detailed analysis of the expression pattern of Ptch (SEQ ID NO:18) and Ptch-2 (SEQ ID NO:1) was performed by in situ hybridization with particular attention to testis. As previously described (Motoyama et al., supra), low levels of Ptch-2 (SEQ ID NO:1) expression were detected in epithelial cells of the developing tooth and skin (data not shown). High levels of Ptch-2 (SEQ ID NO:2) encoding mRNA are expressed inside the seminiferous tubule, on the primary and secondary spermatocytes (FIGS. 6B, 6E) while only low levels of Ptch (SEQ ID NO:4) encoding mRNA can be detected on the Leydig cells located in the interstitium of the seminiferous tubules (FIG. 6A). The primary and secondary spermatocytes are in close contact with the supporting Sertoli cells, the source of Dhh (SEQ ID NO:13) in the testis [Bitgood et al., Curr. Biol. 6: 298–304 (1996)]. To determine which one of the 2 receptors is the most relevant mediator of Dhh (SEQ ID NO:13) activity in the testis, we have analyzed the expression profile of FuRK (SEQ ID NO:10), a Fused Related Kinase that was shown to be a component of the Hh signaling pathway (de Sauvage et al., submitted; copending U.S. Ser. No. 09/031,563, filed Feb. 26, 1998). Consistent with the idea that Patched-2 is the target of Dhh (SEQ ID NO:13) in the testis, we found that FuRK (SEQ ID NO:10) is expressed only in germ cells where it colocalizes with Ptch-2 (SEQ ID NO:2) (FIGS. 4c,f). Dhh (SEQ ID NO:13) is required for proper differentiation of germ cells since male Dhh-deficient mice are sterile due to lack of mature sperm (Bitgood et al., supra). Our data suggest that Dhh (SEQ ID NO:13) acts directly on germ cells through Ptch-2 (SEQ ID NO:2) while the function of Ptch (SEQ ID NO:4) expressed at low levels on testosterone producing Leydig cells is unclear.

Discussion:

Loss of heterozygosity (LOH) for Patched was reported to occur with high frequency in familial as well as sporadic basal cell carcinoma [Johnson et al., Science 272: 1668–71 (1996); Hahn et al., Cell 85: 841–51 (1996); Gailani et al., Nature Genetics 14: 78–81; Xie et al., Cancer Res. 57: 2369–72 (1997)], suggesting that it functions as a tumor suppressor. According to the receptor model described above, loss of Patched function may result in aberrant signaling by Smo (SEQ, ID NO:17), leading to hyperproliferation of the skin basal cell layer. If, as suggested above, Patched-2 mediates the function of Dhh, loss of Patched-2 may lead to tumor formation in tissues where Smo (SEQ ID NO:17) activity is controlled by Patched-2. The gene encoding Ptch-2 (SEQ ID NO:2) was mapped by fluorescence in situ hybridization and by PCR using a radiation hybrid panel to human chromosome 1p33–34 (data not shown). Interestingly, recent analysis of recurrent chromosomal abnormalities in testicular tumors, including seminomas, revealed a deletion of the region 1p32–36 [Summersgill et al., B. J. Cancer 77: 305–313 (1998)]. Loss of this region encompassing the Patched-2 locus was consistent in 36% of the germ cell tumor cases. These data raise the possibility that, like Patched in basal cell carcinoma and medulloblastoma, Patched-2 may be a tumor suppressor in Dhh (SEQ ID NO:13) target cells such as spermatocytes, further implicating Hh signaling in cancer.

In summary, our data demonstrate that both Patched and Patched-2 are genuine Hh receptors and that they are both capable of forming a complex with Smo (SEQ ID NO:17). Although binding data indicate that Patched and Patched-2 do not discriminate between the various Hh ligands through affinity differences, the distinct tissue distribution of these 2 receptors suggests that in vivo, Patched may be the primary receptor for Shh whereas Patched-2 will mediate mainly Dhh signaling. The function of Patched expression in Leydig cells in the absence of some of the Hh signaling components remain to be explained. Similarly, it will be of interest to determine if patched-2 Patched plays a role when expressed in Shh expressing cells present in the developing tooth and skin Motoyama et al, Nature Genet. 18: 104–106 (1998). Finally, the existence of Patched-2 raises the question of whether additional patched receptors exist, in particular one that mediates the function of Ihh (SEQ ID NO:29).

Material and Methods:

1. Isolation of Human Patched-2 cDNA Clones

An expressed sequence tag (EST) DNA database (LIFESEQ™, Incyte Pharmaceuticals, Palo Alto, Calif.) was searched for a human homologue of the Drosophila segment polarity gene patched-2. Two ESTs (Incyte #905531 and 1326258) (FIG. 2) were identified as a potential candidates. In order to identify human cDNA libraries containing human patched-2 clones, human cDNA libraries in pRK5 were first screened by PCR using the following primers:

5'-905531(A): 5'-AGGCGGGGGATCACAGCA-3' (SEQ ID NO:19)

3'-905531(A): 5'-ATACCAAAGAGTTCCACT-3' (SEQ ID NO:20)

A fetal lung library was selected and enriched for patched-2 cDNA clones by extension of single stranded DNA from plasmid libraries grown in dut⁻/ung⁻ host using the 3'-905531(A) primer in a reaction containing 10 µl of 10×PCR Buffer (Klentaq®), 1 µl dNTP (200 µM), 1 µl library DNA (200 ng), 0.5 µl primer, 86.5 µl H$_2$O and 1 µl of Klentaq® (Clontech) added after a hot start. The reaction was denatured for 1 min. at 95° C., annealed for 1 min. at 60° C. then extended for 20 min. at 72° C. DNA was extracted with phenol/CHCl$_3$, ethanol precipitated, then transformed by electroporation into DH10B (Gibco/BRL) host bacteria. Colonies from each transformation were replica plated on nylon membranes and screened with an overlapping oligo probe derived from the EST sequence (#905531) of the following sequence:

5'-ptch2 probe: 5'-CTGCGGCGCTGCTTCCTGCTG GCCGTCTGCATCCTGCTGGTGTGC-3 (SEQ ID NO:21)

3'-ptch2 probe: 5'-AGAGCACAGACGAGGAAAGTG CACACCAGCAGGATGCAGACGGCC-3' (SEQ ID NO:22)

The oligo probe was labeled with [γ-$^{32}$P]-ATP and T4 polynucleotide kinase. Filters were hybridized overnight at 42° C. in 50% formamide, 5×SSC, 10×Denhardt's, 0.05M sodium phosphate (pH 6.5), 0.1% sodium pyrophosphate, 50 µg/ml of sonicated salmon sperm DNA. The filters were then rinsed in 2×SSC and washed in 0.1×SSC, 0.1% SDS then exposed to Kodak® X Ray films.

Using this procedure, a partial clone was isolated from the fetal brain library (clone 3A—FIG. 10) (SEQ ID NO:8). In order to isolate the missing 5'-sequence, a testis library (see northern blot analysis, infra) was screened. The primer set used to amplify a 204 bp probe from clone 3A to probe the testis library was:

RACE 5: 5'-ACTCCTGACTTGTAGCAGATT-3' (SEQ ID NO. 23) and

RACE 6: 5'-AGGCTGCATACACCTCTCAGA-3' (SEQ ID NO:24).

The amplified probe was purified by excision from an agarose gel and labeled with a random primer labeling kit (Boehringer Mannheim). Several clones were isolated, including one (clone 16.1—FIG. 11) (SEQ ID NO:9) containing a potential initiation methionine. A full length cDNA encoding a Patched-2 was reconstructed by assembling several of these clones. The full length cDNA encoding human Ptch-2 (FIG. 1 (SEQ ID NO:1)) has a 3612 nucleotide long open reading frame encoding a 1204 amino acid protein with a 144 kDa predicted molecular weight. Alignment with human Ptch (SEQ ID NO:4) reveals a 53% identity between the 2 molecules at the amino acid level (FIG. 3). All 12 transmembrane domains are conserved. The most significant difference is a shorter C-terminal intercellular domain in Ptch-2 (SEQ ID NO:2) compared to Ptch (SEQ ID NO:4).

2. Northern Blot Analysis:

In order to determine the best tissue source for isolation of the complete full length Patched-2 cDNA as well as to determine its expression profile, we probed human multiple tissue northern blots (Clontech) with a 752 bp fragment amplified from the 3' untranslated region of Patched-2 using the following primers:

TM2: TM2 5-GCTTAGGCCCGAGGAGAT-3' (SEQ ID NO:25)

UTR2: 5'-AACTCACAACTTTCTCTCCA-3' (SEQ ID NO:26).

The resulting fragment was gel purified and labeled by random priming. The blots were hybridized in ExpressHyb® hybridization solution (Clontech) in the presence of 1×10$^6$ cpm/ml $^{32}$P-labeled probe at 42° C. overnight. The blots were washed in 2×SSC at room temperature for 10 minutes and washed in 0.1×SSC/0.1% SDS at 42° C. for 30 minutes then exposed to x-ray film overnight. FIG. 4 shows that Ptch-2 message is expressed at high levels in only the testis.

Figure 5:
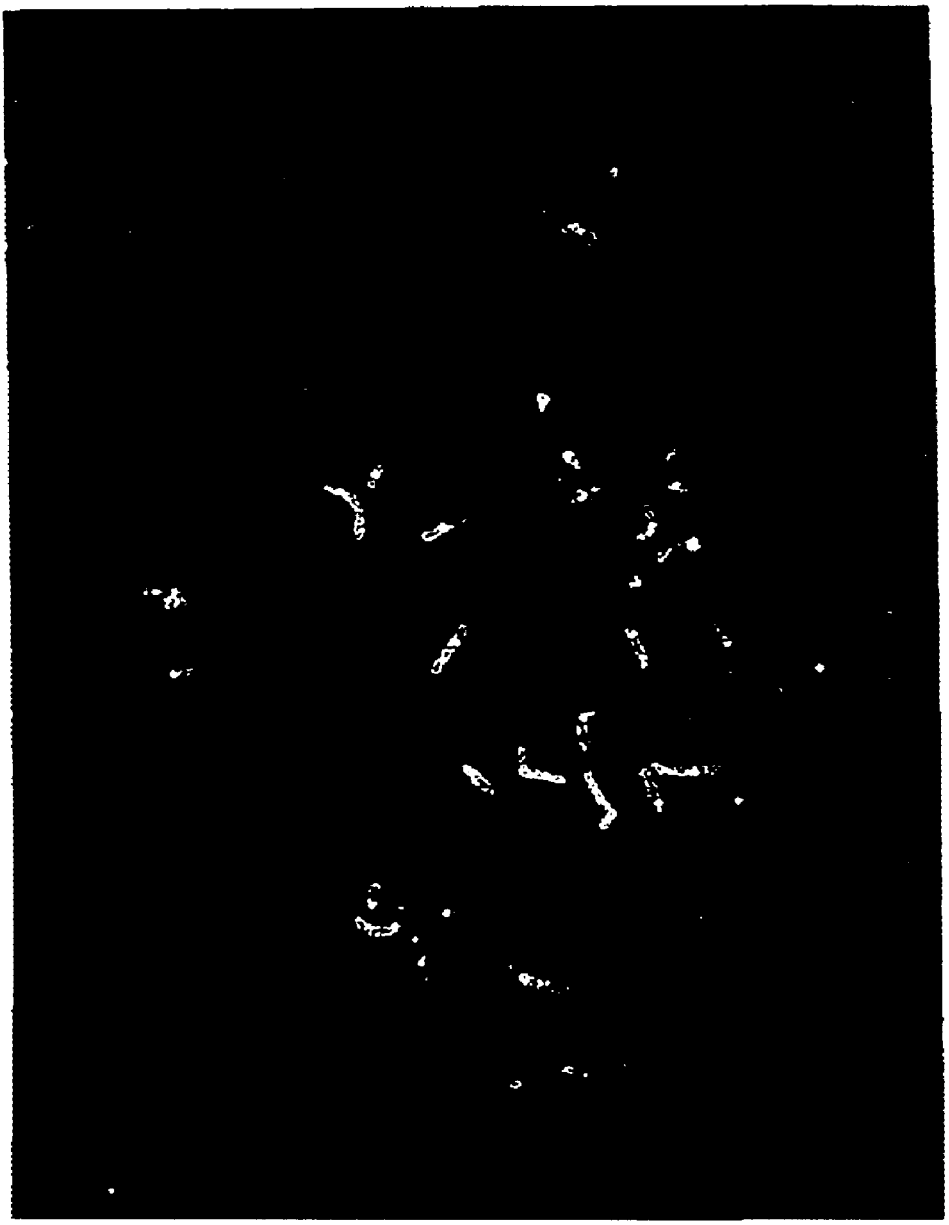
FIG. 5 shows a chromosomal localization of two BAC clones which were isolated by PCR screening with human patched-2 derived probes. Both probes were mapped by FISH to human chromosome 1p33–34.

3. Chromosomal Localization:

The primers TM2 (SEQ ID NO:25) and UTR2 (SEQ ID NO:26) described above were used to screen the Genome Systems (St. Louis, Mo.) BAC library. Two individual BAC clones were obtained from this library and chromosomal localization of both of the clones by FISH indicated that Ptch-2 (SEQ ID NO:2) maps to human chromosome 1p33–34 (FIG. 5). Loss of heterozygosity (LOH) for Patched was reported to occur with high frequency in basal cell carcinoma. Loss of Patched function is thought to lead to constitutive signaling by Smoothened (Smo) (SEQ ID NO:17), resulting in hyperproliferation of the basal layer of the dermis. A similar mechanism may lead to the formation of germ cell tumors. This model proposes that the first step in the progression of a germ cell tumor is an initial loss of DNA by a germ cell precursor, leading to a neoplastic germ cell which then forms a seminoma [De Jong et al., Cancer Genet. Cytogenet. 48: 143–167 (1990)]. From the invasive seminoma, all other forms of germ cell tumor types develop. Approximately 80% of all germ cell tumors correlate with an isochromosome 12p (i12p) and is found at a higher frequency in non-seminomas than seminomas [Rodriguez et al., Cancer Res. 52: 2285–2291 (1992)]. However, analysis of recurrent chromosomal abnormalities in testicular tumors including seminomas revealed a deletion of the region 1p32–36. Loss of this region was consistent in 36% of the germ cell tumor cases of in a recent study Summersgill et al., B. J. Cancer 57: 305–313 (1998)). A similar deletion of chromosome 1p32–36 has been reported at a frequency of 28% in oligodendrogliomas; Bello, et al., Int. J. Cancer 57: 172–175 (1994). While expression of Ptch-2 (SEQ ID NO:2) in the brain was not examined here in detail, Ptch-2 (SEQ ID NO:2) is thought to be the Dhh receptor (see below) and expression of Dhh by murine Schwann cells was previously reported [Bitgood et al., Develop. Biol. 172: 126–138 (1995)]. Since Ptch-2 (SEQ ID NO:2) localizes to chromosome 1p33–34 it is possible that Patched-2 regulates Smo (SEQ ID NO:17) signaling in Dhh target cells and that loss of Patched-2 function leads to abnormal Smo (SEQ ID NO:17) signaling in these cells and subsequent tumor formation.

4. In situ Hybridization:

Mouse testis sections were cut at 16 μm, and processed for in situ hybridization by the method described in Phillips et al., Science 250: 290–294 (1990). $^{33}$P-UTP labeled RNA probes were generated as described in Melton et al., Nucleic Acids Res. 12: 7035–7052 (1984). Sense and antisense probes were synthesized from the 3' noncoding region of the mouse Patched or Patched-2 and from a mouse FuRK cDNA fragment corresponding to the region encoding amino acid 317–486 of the human sequence using T3 and T7, respectively.

PTCH:
503 (Anti-sense)
  5'GGATTCTAATACGACTCACTATAGGGC-CCAATGGCCTAAACCGACTGC3' (SEQ ID NO:27)
503 (Sense)
  5'CTATGAAATTAACCCTCACTAAAGGGAC-CCACGGCCTCTCCTCACA3' (SEQ ID NO:28)
PTCH2:
504 (Anti-sense)
  5'GGATTCTAATACGACTCACTATAGGGC-CCCTAAACTCCGCTGCTCCAC3' (SEQ ID NO:12)
504 (Sense)
  5'CTATGAAATTAACCCTCACTAAAGG-GAGCTCCCGTGAGTCCCTATGTG3' (SEQ ID NO:11)

FuRK sense and antisense were synthesized from a mouse fused DNA fragment using T3 and T7, respectively, corresponding to the region encoding amino acid residues 317486 of the human sequence de Sauvage et al., submitted, 1998; copending U.S. Ser. No. 09/031,563, filed Feb. 26, 1998).

FIG. 6 illustrates that, although both Ptch (SEQ ID NO:4) and Ptch-2 (SEQ ID NO:2) are expressed in testis, their expression pattern does not overlap. Ptch (SEQ ID NO:4) is expressed in the Leydig cells of the interstitium while Ptch-2 (SEQ ID NO:2) is expressed in the primary and secondary spermatocytes.

The expression of Patched-2 specifically in the developing spermatogonia suggest that Patched-2 is the immediate target of Dhh (SEQ ID NO:13). Dhh (SEQ ID NO:13) is expressed by Sertoli cells and mice deficient in Dhh are sterile because of a defect in sperm production [Bitgood et al., Curr. Biol. 6: 298–304 (1996)]. Although this effect on germ cells was though to be indirect and mediated by Patched present on Leydig cells, our data suggest that Dhh directly acts on germ cells through Patched-2. This is further demonstrated by the localization of FuRK (SEQ ID NO:10), an intercellular kinase homologous to Drosophila Fused and involved in transducing the Hedgehog (Hh) signal. As shown in FIG. 6, FuRK (SEQ ID NO:10) is colocalizes with Ptch-2 (SEQ ID NO:2) in germ cells and not with Ptch (SEQ ID NO:4) in Leydig cells, suggesting that Patched-2 and not Patched will be able to transduce the Dhh signal. These results suggest that Patched-2 is a Dhh receptor.

Ptch-2 mRNA levels in Smo-M2 (SEQ ID NO:16) transgenic mice with a Smo mutation which results in autonomous phenotypes similar to BCC, Xie et al., Nature 391: 90–92 (1998)] can be increased upon abnormal activation of the Hh signaling pathway. As indicated in FIG. 9, Ptch-2 (SEQ ID NO:2) levels were high in tumor cells (although lower than Ptch (SEQ ID NO:4) levels). This suggests that antibodies directed toward Ptch-2 (SEQ ID NO:2) may be useful in the treatments of BCC.

5. Immunoprecipitation with Smo:

The binding of Patched-2 to Smo (SEQ ID NO:17) was assessed by cotransfection using a transient transfection system of a myc-epitope tagged Smo (SEQ ID NO:15) and a FLAG-epitope tagged Patched or Patched-2 expression construct in 293 cells using standard techniques (Gorman, C., *DNA Cloning: A Practical Approach*, Clover, D M ed., Vol. 11, pp. 143–190, IRL Press, Washington, D.C.). 36 hours after transfection, the cells were lysed in 1% NP-40 and immunoprecipitated overnight with the 9E10 anti-myc antibody or with the M2 anti-FLAG antibody (IBI-Kodak) followed by protein A Sepharose, and then separated on a denatured 6% polyacrylamide gel. Proteins were detected by transfer to nitrocellulose and probing with antibodies to Flag or Myc epitopes, using the ECL detection system (Amersham). FIG. 7B indicates that both Ptch (SEQ ID NO:4) or Ptch-2 (SEQ ID NO:2) are expressed at the same level (IP Flag, Blot Flag) and that like Ptch (SEQ ID NO:4), Ptch-2 (SEQ ID NO:2) forms a physical complex with Smo (SEQ ID NO:17). These results suggest that like Patched, Patched-2 controls Hh signaling through its interaction with Smo (SEQ ID NO:17).

6. Hh Binding:

To determine whether Patched-2 is able to bind to the various hedgehog ligands, 293 cells were transfected with Ptch (SEQ ID NO:4) or Ptch-2 (SEQ ID NO:2) using standard procedures. Cells were incubated with 100 pM $^{125}$I-Shh (19kD amino terminal fragment of murine Shh (SEQ ID NO:14)) in the presence or absence of excess unlabeled Shh (SEQ ID NO:14) or Dhh (SEQ ID NO:13) for 2 h at room temperature. After equilibrium was reached, the ligand bound cells were centrifuged through a continuous sucrose gradient to separate unincorporated and then counted in a scintillation counter. FIG. 7A shows that both Dhh (SEQ ID NO:13) and Shh (SEQ ID NO:14) bind to Ptch (SEQ ID NO:4) and Ptch-2 (SEQ ID NO:2). Varying concentrations of cold competitor indicate that the 2 ligands have similar affinity for Ptch (SEQ ID NO:4) and Ptch-2 (SEQ ID NO:2).

Example 2

Expression of Patched-2 in *E. coli*

The DNA sequence encoding human patched-2 is initially amplified using selected PCR primers. The primers should contain restriction enzyme sites that correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences that encode for an antibiotic resistance gene, a trp promoter, a polyhis leader (including the first six STII codons, polyhis sequence, and enterokinase cleavage site), the vertebrate patched-2 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized vertebrate patched-2 protein can then be purified using a metal chelating column under conditions that allow tight binding of the protein.

Example 3

Expression of Patched-2 in Mammalian Cells

The vector, pRK5 (see EP 307,247, published Mar. 15, 1989), is employed as the expression vector. Optionally, the vertebrate patched-2 DNA is ligated into pRK5 with selected restriction enzymes to allow insertion of the vertebrate patched-2 DNA using ligation methods such as described in Sambrook et al., supra. The resulting vector is called pRK5-patched-2.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-patched-2 DNA is mixed with about 1 μg DNA encoding the VA RNA gene [Thimmappaya et al., *Cell*, 31:543 (1982)] and dissolved in 500 μl of 1 mM Tris-HCl, 0.1 mM EDTA, 0.227 M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of vertebrate patched-2 polypeptide. The cultures containing transfected cells may undergo further incubation (in serum free medium) and the medium is tested in selected bioassays.

In an alternative technique, vertebrate patched-2 may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRKS-patched-2 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed vertebrate patched-2 can then be concentrated and purified by any selected method, such as dialysis and/or column chromatography.

In another embodiment, vertebrate patched-2 can be expressed in CHO cells. The pSVi-patched-2 can be transfected into CHO cells using known reagents such as CaPO$_4$ or DEAE-dextran. As described above, the cell cultures can be incubated, and the medium replaced with culture medium (alone) or medium containing a radiolabel such as $^{35}$S- methionine. After determining the presence of vertebrate patched-2 polypeptide, the culture medium may be replaced with serum free medium. Preferably, the cultures are incubated for about 6 days, and then the conditioned medium is harvested. The medium containing the expressed vertebrate patched-2 can then be concentrated and purified by any selected method.

Epitope-tagged vertebrate patched-2 may also be expressed in host CHO cells. The vertebrate patched-2 may be subcloned out of the pRK5 vector. The subclone insert can undergo PCR to fuse in frame with a selected epitope tag such as a poly-his tag into an expression vector. The poly-his tagged vertebrate patched-2 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged vertebrate patched-2 can then be concentrated and purified by any selected method, such as by $Ni^{2+}$-chelate affinity chromatography.

Example 4

Expression of Vertebrate Patched-2 in Yeast

The following method describes recombinant expression of vertebrate patched-2 in yeast.

First, yeast expression vectors are constructed for intracellular production or secretion of vertebrate patched-2 from the ADH2/GAPDH promoter. DNA encoding vertebrate patched-2, a selected signal peptide and the promoter is inserted into suitable restriction enzyme sites in the selected plasmid to direct intracellular expression of vertebrate patched-2. For secretion, DNA encoding vertebrate patched-2 can be cloned into the selected plasmid, together with DNA encoding the ADH2/GAPDH promoter, the yeast alpha-factor secretory signal/leader sequence, and linker sequences (if needed) for expression of vertebrate patched-2.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant vertebrate patched-2 can subsequently be isolated and purified by removing the yeast cells from the fermentation medium by centrifugation and then concentrating the medium using selected cartridge filters. The concentrate containing vertebrate patched-2 may further be purified using selected column chromatography resins.

Example 5

Expression of Vertebrate Patched-2 in Baculovirus-infected Insect Cells

The following method describes recombinant expression of vertebrate patched-2 in Baculovirus-infected insect cells.

The vertebrate patched-2 is patched-2 upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the vertebrate patched-2 or the desired portion of the vertebrate patched-2 (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged vertebrate patched-2 can then be purified, for example, by $Ni^{2+}$-chelate affinity chromatography as follows. Extracts are prepared from recombinant viris-infected Sf9 cells as described by Rupert et al., *Nature*, 362:175–179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged vertebrate patched-2 are pooled and dialyzed against loading buffer.

Alternatively, purification of the IgG tagged (or Fc tagged) vertebrate patched-2 can be performed using known chromatography techniques, including for instance, Protein A or protein G column chromatography.

Example 6

Preparation of Antibodies that Bind Vertebrate Patched-2

This example illustrates preparation of monoclonal antibodies, which can specifically bind vertebrate patched-2.

Techniques for producing the monoclonal antibodies are known in the art and are described, for instance, in Goding, supra. Immunogens that may be employed include purified vertebrate patched-2, fusion proteins containing vertebrate patched-2, and cells expressing recombinant vertebrate patched-2 on the cell surface. Selection of the immunogen can be made by the skilled artisan without undue experimentation.

Mice, such as Balb/c, are immunized with the vertebrate patched-2 immunogen (E.g., extracellular portions or cells expressed ptch-2) emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect vertebrate patched-2 antibodies.

After a suitable antibody titer has been detected, the animals "positive" for antibodies can be injected with a final intravenous injection of vertebrate patched-2. Three to four days later, the mice are sacrificed and the spleen cells are harvested. The spleen cells are then patched-2 (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-patched-2 cells, myeloma hybrids, and spleen cell hybrids.

The hybridoma cells will be screened in an ELISA for reactivity against vertebrate patched-2. Determination of "positive" hybridoma cells secreting the desired monoclonal antibodies against vertebrate patched-2 is within the skill in the art.

The positive hybridoma cells can be injected intraperitoneally into syngeneic Balb/c mice to produce ascites containing the anti-vertebrate patched-2 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 7

Gli Luciferase Assay

The following assay may be used to measure the activation of the transcription factor GLI, the mammalian homologue of the *Drosophila cubitus interruptus* (Ci). It has been shown that GLI is a transcription factor activated upon SHh stimulation of cells.

Nine (9) copies of a GLI binding site present in the HNF3β enhancer, (Sasaki et al., *Development* 124: 1313–1322 (1997)), are introduced in front of a thymidine kinase minimal promoter driving the luciferase reporter gene in the pGL3 plasmid (Promega). The sequence of the GLI binding sequence is: TCGACAAGCAGG GAACACCCAAGTAGAAGCTC (p9XGliLuc) (SEQ ID NO:31), while the negative control sequence is: TCGA-CAAGCAGGGAAGTGGGAAGTAGAAGCTC (p9XmGliLuc) (SEQ ID NO:32). These constructs are cotransfected with the full length Ptch-2 and Smo in C3H10T1/2 cells grown in F12, DMEM (50:50), 10% FCS heat inactivated. The day before transfection $1 \times 10^5$ cells per well was inoculated in 6 well plates, in 2 ml of media. The following day, 1 µg of each construct is cotransfected in duplicate with 0.025 mg ptkRenilla luciferase plasmid using lipofectamine (Gibco-BRL) in 100 µl OptiMem (with GlutaMAX) as per manufacturer's instructions for 3 hours at 37° C. Serum (20%, 1 ml) is then added to each well and the cells were incubated for more hours at 37° C. Cells are then washed twice with PBS, then incubated for 48 hours at 37° C. in 2 ml of Each well is then washed with PBS, and the cells lysed in 0.5 ml Passive Lysis Buffer (Promega) for 15 min. at room temperature on a shaker. The lysate is transferred in eppendorf tubes on ice, spun in a refrigerated centrifuge for 30 seconds and the supernatant saved on ice. For each measure, 20 µl of cell lysate is added to 100 µl of LARII (luciferase assay reagent, Promega) in a polypropylene tube and the luciferase light activity measured. The reaction is stopped by the addition of Stop and Glow buffer (Promega), mixed by pipetting up and down 3 to 5 times and Renilla luciferase lights activity is measured on the luminometer.

Deposit of Material

The following materials have been deposited with the American Type Culture Collection, 10801 University Boulevard, Manassas, Va., USA (ATCC):

| Designation: | ATCC Dep. No. | Deposit Date |
|---|---|---|
| pRK7.hptc2.Flag-1405 | 209778 | Apr. 14, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. Isolated nucleic acid comprising DNA having least a 95% sequence identity, as measured by BLAST-2 set to the default parameters to: (a) a DNA molecule encoding a patched-2 polypeptide comprising the sequence of amino acids 1 to about 1203 of FIG. 1 (SEQ ID NO:2) and encoding a polypeptide that binds hedgehog; or (b) the complement of (a).

2. A vector comprising the nucleic acid of claim 1.

3. The vector of claim 2 operably linked to control sequences recognized by a host cell transformed with the vector.

4. A host cell transformed with the vector of claim 2.

5. The host cell of claim 4 which is mammalian.

6. The host cell of claim 5 wherein said cell is a CHO cell.

7. The host cell of claim 4 which is prokaryotic.

8. The host cell of claim 7 wherein said cell is an *E. coli*.

9. The host cell of claim 4 wherein said cell is a yeast cell.

10. The host cell of claim 9 which is *Saccharomyces cerevisiae*.

11. A process for producing patched-2 polypeptides comprising culturing the host cells of claim 4 under conditions suitable for expression of patched-2 nucleic acid and recovering patched-2 polypeptide from the cell culture.

12. The nucleic acid of claim 1, comprising a DNA molecule encoding the sequence of amino acids 1 to about 1203 of FIG. 1 (SEQ ID NO:2).

13. The nucleic acid of claim 1, wherein the isolated nucleic acid is the DNA molecule encoding the sequence of amino acids 1 to about 1203 of FIG. 1 (SEQ ID NO:2).

14. An isolated nucleic acid comprising DNA having at least 3609 base pairs and having at least a 95% sequence identity, as measured by BLAST-2 set to the default parameters to: (a) a DNA molecule encoding the same mature polypeptide encoded by the cDNA in ATCC Deposit No. 209778 (designation: pRK7.hptc2.Flag-1405) and encoding a polypeptide that binds hedgehog; or (b) the complement of the DNA molecule of (a).

15. The isolated nucleic acid of claim 14 comprising human patched-2 encoding sequence of the cDNA in ATCC deposit No. 209778 (designation: pRK7.hptc2.Flag-1405), or a sequence which hybridizes thereto under stringent conditions.

16. The nucleic acid of claim 14, comprising a DNA molecule encoding the same mature polypeptide encoded by the cDNA in ATCC Deposit No. 209778.

17. The nucleic acid of claim 14, wherein the isolated nucleic acid is the DNA molecule encoding the same mature polypeptide encoded by the cDNA in ATCC Deposit No. 209778.

18. Isolated nucleic acid comprising DNA having at least 3609 base pairs and having at least a 95% sequence identity, as measured by BLAST-2 set to the default parameters to: (a) a DNA molecule encoding a patched-2 polypeptide comprising the sequence of amino acids 1 to about 1203 of FIG. 1 (SEQ ID NQ:2) and encoding a polypeptide that binds hedgehog; or (b) the complement of (a).

19. The nucleic acid of claim 18, comprising a DNA molecule encoding the patched-2 polypeptide of the amino acid sequence 1 to about 1203 of FIG. 1 (SEQ ID NO:2).

20. The nucleic acid of claim 18, wherein the isolated nucleic acid is the DNA molecule encoding the patched-2 polypeptide of the amino acid sequence 1 to about 1203 of FIG. 1 (SEQ ID NO:2).

21. An isolated nucleic acid comprising DNA having at least 95% sequence identity, as measured by BLAST-2 set to the default parameters, to a DNA molecule encoding the same mature polypeptide encoded by the cDNA in ATCC Deposit No. 209778 (designation: pRK7.hptc2.Flag-1405) and encoding a polypeptide that binds hedgehog.

22. The nucleic acid of claim 21, comprising a DNA molecule encoding the same mature polypeptide encoded by the cDNA in ATCC Deposit No. 209778.

23. The nucleic acid of claim 21, wherein the isolated nucleic acid is the DNA molecule encoding the same mature polypeptide encoded by the cDNA in ATCC Deposit No. 209778.

* * * * *

UNITED STATES PATENT AND TRADEMARK OFFICE
CERTIFICATE OF CORRECTION

PATENT NO. : 6,709,838 B1
DATED : March 23, 2004
INVENTOR(S) : de Sauvage et al.

It is certified that error appears in the above-identified patent and that said Letters Patent is hereby corrected as shown below:

Column 11,
Line 49, please replace "in" with -- to --.

Column 14,
Line 27, please replace "genomic. libraries" with -- genomic libraries --.

Column 18,
Line 27, please replace "patched-2" with -- Patched-2 --.
Line 47, please replace "phentotype" with -- phenotype --.
Line 60, please replace "13). For" with -- 13), for --.
Line 60, after "cancer" please delete ")".

Column 20,
Line 52, please replace ""knock out"" with -- "knockout" --.

Column 21,
Line 17, after "diabetes,", please insert -- and --.

Column 22,
Line 8, please replace "which substances prevent" with -- which are substances that prevent --.

Column 25,
Line 21, after "such", please replace "a" with -- as --.
Line 34, after "Patched" please insert -- , --.
Line 44, please replace "low" with -- lower --.

Column 28,
Line 36, after "5,155,031" please insert -- ) --.

Column 29,
Line 23, please replace "substrate" with -- substrates --.

Column 30,
Line 22, please replace "substrate" with -- substrates --.
Line 32, please replace "biotin)," with -- biotin, --.
Line 67, please replace "agonist" with -- agonists --.

UNITED STATES PATENT AND TRADEMARK OFFICE
CERTIFICATE OF CORRECTION

PATENT NO. : 6,709,838 B1
DATED : March 23, 2004
INVENTOR(S) : de Sauvage et al.

It is certified that error appears in the above-identified patent and that said Letters Patent is hereby corrected as shown below:

Column 31,
Line 13, please replace "include" with -- including --.

Column 32,
Line 24, please delete the second instance of "of a compound".
Line 32, please replace "concentration" with -- concentrations --.

Column 36,
Line 58, please replace "PTCH2" with -- Ptch-2 --.

Column 38,
Line 14, after "as" please delete "a".

Column 39,
Line 53, after "of" please delete "in" and after "study" insert -- . --.

Column 40,
Line 31, please delete ")" after "1998".
Line 33, please replace "testis" with -- testes --.
Line 44, please replace "though" with -- thought --.

Column 41,
Line 9, please replace "probing" with -- probed --.

Column 46,
Line 1, after "of", please insert -- media. --.

Lines 40 and 42, please replace "▯" with -- § --.

UNITED STATES PATENT AND TRADEMARK OFFICE
CERTIFICATE OF CORRECTION

PATENT NO. : 6,709,838 B1
DATED : March 23, 2004
INVENTOR(S) : de Sauvage et al.

It is certified that error appears in the above-identified patent and that said Letters Patent is hereby corrected as shown below:

Column 105,
Line 34, after "having" and before "least a", please insert -- at --.

Signed and Sealed this

Third Day of May, 2005

JON W. DUDAS
*Director of the United States Patent and Trademark Office*